United States Patent
Lim

(10) Patent No.: US 9,238,819 B2
(45) Date of Patent: Jan. 19, 2016

(54) METHOD FOR SPEEDING UP PLANT GROWTH AND IMPROVING YIELD BY ALTERING EXPRESSION LEVELS OF KINASES AND PHOSPHATASES

(75) Inventor: Boon Leong Lim, Hong Kong (CN)

(73) Assignee: Versitech Limited, Hong Kong (HK)

( * ) Notice: Subject to any disclaimer, the term of this patent is extended or adjusted under 35 U.S.C. 154(b) by 662 days.

(21) Appl. No.: 13/385,881

(22) Filed: Mar. 12, 2012

(65) Prior Publication Data

US 2012/0284874 A1    Nov. 8, 2012

Related U.S. Application Data

(60) Provisional application No. 61/482,467, filed on May 4, 2011.

(51) Int. Cl.
    *C12N 15/82* (2006.01)
    *C12N 9/12* (2006.01)
    *C12N 9/16* (2006.01)

(52) U.S. Cl.
    CPC .......... *C12N 15/8261* (2013.01); *C12N 9/1205* (2013.01); *C12N 9/16* (2013.01)

(58) Field of Classification Search
    None
    See application file for complete search history.

(56) References Cited

U.S. PATENT DOCUMENTS

| | | | |
|---|---|---|---|
| 2004/0009476 A9 | 1/2004 | Harper et al. | |
| 2004/0214272 A1 * | 10/2004 | La Rosa et al. | 435/69.1 |
| 2006/0048240 A1 | 3/2006 | Alexandrov et al. | |
| 2006/0150283 A1 | 7/2006 | Alexandrov et al. | |
| 2006/0183137 A1 | 8/2006 | Harper et al. | |
| 2007/0016976 A1 | 1/2007 | Katagiri et al. | |
| 2007/0214517 A1 | 9/2007 | Alexandrov et al. | |
| 2008/0160161 A1 | 7/2008 | Davies et al. | |
| 2009/0075829 A1 | 3/2009 | Bush et al. | |
| 2009/0215647 A1 | 8/2009 | Bush et al. | |
| 2009/0287008 A1 | 11/2009 | Davies et al. | |
| 2010/0037355 A1 | 2/2010 | Alexandrov et al. | |
| 2010/0043097 A1 | 2/2010 | Wang et al. | |
| 2010/0083407 A1 | 4/2010 | Feldmann et al. | |
| 2010/0159065 A1 | 6/2010 | Lim | |
| 2010/0287671 A1 | 11/2010 | Harper et al. | |

OTHER PUBLICATIONS

UniProtKB/TrEMBL Accession No. B8A2T3, Mar. 3, 2009.*
Kano-Murakami Y. et al. A rice homeotic gene, OSH1, causes unusual phenotypes in transgenic tobacco. FEBS Lett. Nov. 22, 1993;334(3):365-8.*
Whisstock J.C. et al. Prediction of protein function from protein sequence and structure. Q Rev Biophys. Aug. 2003;36(3):307-40. Review.*
Samis et al. Pyramiding Mn-superoxide dismutase transgenes to improve persistence and biomass production in alfalfa. J. Exp. Bot. May 2002;53(372):1343-50.*
Klabunde et al., Mechanism of Fe(III)—Zn(II) purple acid phosphatase based on crystal structures, *J Mol Biol.*,1996, vol. 259(4), pp. 737-748.
Li et al., Purple acid phosphatases of Arabidopsis thaliana. Comparative analysis and differential regulation by phosphate deprivation, *J Biol Chem.*, 2002, vol. 277(31), pp. 27772-27781.
Klabunde at al., The dimetal center in purple acid phosphatases, *Structure & Bonding*, 1997, vol. 89/1997, pp. 177-198.
Schenk et al., Binuclear metal centers in plant purple acid phosphatases; Fe—Mn in sweet potato and Fe—Zn in soybean, *Arch Biochem Biophys*, 1999, vol. 370(2), pp. 183-189.
Liu et al., Regulation of Arabidopsis thaliana Ku genes at different developmental stages under heat stress, *Biochim Biophys Acta*, 2008, vol. 1779, pp. 402-407.
Clough et al., "Floral dip: a simplified method for Agrobacterium-mediated transformation of Arabidopsis thaliana", *The Plant Journal*, 1998, vol. 16, pp. 735-743.

* cited by examiner

*Primary Examiner* — Cynthia Collins
(74) *Attorney, Agent, or Firm* — Dentons US LLP

(57) ABSTRACT

Transgenic plants having increased growth rate and increase yield are disclosed, and methods for making the same. In one embodiment, the method comprises: transforming a plant or plant cell with a nucleic acid molecule comprising a plant kinase and/or phosphatase gene selected from NG6, NG21, NG24, NG28, and NG32, and over-expressing said kinase and/or phosphatase gene in the plant or plant cell.

22 Claims, 5 Drawing Sheets

Fig4A. qRT-PCR of NG gene OE lines (Trial 1)     Fig4B. qRT-PCR of NG gene OE lines (Trial 2)

a          b

SEQUENCE LISTING

<160> NUMBER OF SEQ ID NOS: 102

<210> SEQ ID NO 1
<211> LENGTH: 648
<212> TYPE: DNA
<213> ORGANISM: Arabidopsis thaliana

<400> SEQUENCE: 1

```
atgaagcttg tggagaagac gactactaca gagcaggaca atggagaaga tttctgccgc     60
accatcatcg aggtttccga ggttaacaga aacgtgtttc aggctccggg cggtgaagct    120 gatcccttc gagttgtctc cggcgaagaa cttcacctaa ttccgccgct caacttctcc    180
atggtcgata acggtatatt ccggtctgga ttccctgatt cagctaactt ctcctttctc    240
```

```
cagactctcg gtctccgctc aatcatatac ttgtgcccgg agccctaccc agagagcaat      300
ctccagttcc ttaaatccaa tggaatcagg cttttccagt ttggtattga aggcaacaag      360
gagccatttg tgaatattcc agccataaaa tccgcatgg cactgaaagt gcttctagat       420
gagaaaaacc atcctgttct gattcattgt aagcgaggca agcatcggac cggttgtctt      480
gttggttgct tgaggaagct ccagaaatgg tgtttgacat cgatattcga cgagtaccaa     540
cgatttgcag cagcgaaagc tagagtttca gatcaaagat tcatggagat attcgatgtt     600
tccagcttca gtcatattcc aatgtcattc tcttgttcca tcaggtaa                 648

<210> SEQ ID NO 2
<211> LENGTH: 215
<212> TYPE: PRT
<213> ORGANISM: Arabidopsis thaliana

<400> SEQUENCE: 2

Met Lys Leu Val Glu Lys Thr Thr Thr Glu Gln Asp Asn Gly Glu
1               5                   10                  15

Asp Phe Cys Arg Thr Ile Ile Glu Val Ser Glu Val Asn Arg Asn Val
                20                  25                  30

Phe Gln Ala Pro Gly Gly Glu Ala Asp Pro Phe Arg Val Val Ser Gly
            35                  40                  45

Glu Glu Leu His Leu Ile Pro Pro Leu Asn Phe Ser Met Val Asp Asn
        50                  55                  60

Gly Ile Phe Arg Ser Gly Phe Pro Asp Ser Ala Asn Phe Ser Phe Leu
65                  70                  75                  80

Gln Thr Leu Gly Leu Arg Ser Ile Ile Tyr Leu Cys Pro Glu Pro Tyr
                85                  90                  95

Pro Glu Ser Asn Leu Gln Phe Leu Lys Ser Asn Gly Ile Arg Leu Phe
            100                 105                 110

Gln Phe Gly Ile Glu Gly Asn Lys Glu Pro Phe Val Asn Ile Pro Asp
        115                 120                 125

His Lys Ile Arg Met Ala Leu Lys Val Leu Leu Asp Glu Lys Asn His
    130                 135                 140

Pro Val Leu Ile His Cys Lys Arg Gly Lys His Arg Thr Gly Cys Leu
145                 150                 155                 160

Val Gly Cys Leu Arg Lys Leu Gln Lys Trp Cys Leu Thr Ser Ile Phe
                165                 170                 175

Asp Glu Tyr Gln Arg Phe Ala Ala Lys Ala Arg Val Ser Asp Gln
            180                 185                 190

Arg Phe Met Glu Ile Phe Asp Val Ser Ser Phe Ser His Ile Pro Met
        195                 200                 205

Ser Phe Ser Cys Ser Ile Arg
    210                 215

<210> SEQ ID NO 3
<211> LENGTH: 651
<212> TYPE: DNA
<213> ORGANISM: Zea mays

<400> SEQUENCE: 3
atgaagctgg aggtcatgcc caagcccaaa cagcgggtgc tggaggcgca gcagagggag      60
gaggccatgg agatgagcgg cctggacctg tggaagcacg agaagccgcc aaggatctgc    120
cccttgcccc gtcgctccc gccgccgccg ccagcgttcg acgaggcggc gctcgtgccg     180
ccgctcaact tcgccgtggt cgacgacggc atcttccgct ccggattccc agggaccgcc    240
```

```
aacttccggt tcctcaagtc cctcaacctc cgctccatcg tgtacctgtg cccggagccg    300
tacccgggga cgaacacgga gttcctagaa aagaatggga tcaggctcca ccagttcgga    360
atcgaggggc gcaaggaacc atttgtcaac atacccgacg acaaaataag ggaggcgctc    420
aaagttgtct tagacccaag aaaccaacct ctgcttatcc attgcaagag aggcaagcac    480
cgaactggct gtgtggtcgg atgcttgagg aagctgcagg aatggtgctt gtcttcagtc    540
ttggacgagt accatcgctt tgccgctgcg aaagcgagga tcactgacca gaggttcatg    600
gagctgttcg acgtttcaag cttgaagcac ctgacaccct cacactgtta a             651
```

<210> SEQ ID NO 4
<211> LENGTH: 216
<212> TYPE: PRT
<213> ORGANISM: Zea mays

<400> SEQUENCE: 4

```
Met Lys Leu Glu Val Met Pro Lys Pro Lys Gln Arg Val Leu Glu Ala
1               5                   10                  15

Gln Gln Arg Glu Glu Ala Met Glu Met Ser Gly Leu Asp Leu Trp Lys
            20                  25                  30

His Glu Lys Pro Pro Arg Ile Cys Pro Leu Pro Ser Leu Pro Pro
        35                  40                  45

Pro Pro Pro Ala Phe Asp Glu Ala Ala Leu Val Pro Pro Leu Asn Phe
    50                  55                  60

Ala Val Val Asp Asp Gly Ile Phe Arg Ser Gly Phe Pro Gly Thr Ala
65                  70                  75                  80

Asn Phe Arg Phe Leu Lys Ser Leu Asn Leu Arg Ser Ile Val Tyr Leu
                85                  90                  95

Cys Pro Glu Pro Tyr Pro Gly Thr Asn Thr Glu Phe Leu Glu Lys Asn
            100                 105                 110

Gly Ile Arg Leu His Gln Phe Gly Ile Glu Gly Arg Lys Glu Pro Phe
        115                 120                 125

Val Asn Ile Pro Asp Asp Lys Ile Arg Glu Ala Leu Lys Val Val Leu
    130                 135                 140

Asp Pro Arg Asn Gln Pro Leu Leu Ile His Cys Lys Arg Gly Lys His
145                 150                 155                 160

Arg Thr Gly Cys Val Val Gly Cys Leu Arg Lys Leu Gln Glu Trp Cys
                165                 170                 175

Leu Ser Ser Val Leu Asp Glu Tyr His Arg Phe Ala Ala Ala Lys Ala
            180                 185                 190

Arg Ile Thr Asp Gln Arg Phe Met Glu Leu Phe Asp Val Ser Ser Leu
        195                 200                 205

Lys His Leu Thr Pro Ser His Cys
    210                 215
```

<210> SEQ ID NO 5
<211> LENGTH: 627
<212> TYPE: DNA
<213> ORGANISM: glycine max

<400> SEQUENCE: 5

```
atgcaagtgg cggcagaact ccaacgcgcc catcaccacc accaaaggca caaacaagac     60
actcccatgt gccgccaaat ccagctcact atctccgatc acaccaccgc cggagacgac    120
gacggcgagg atctcttcat tccgcccctc aacttcgcca tggttgataa tggcatttc     180 cgctccggct tccccgaacc cgccaacttc tccttcctcc aaaccctcgg cctccgttcc    240
```

```
atcatatatc tgtgtcctga gccgtatccg gaggccaata tggagttcct caagtcaaat    300
gggatcaagc ttttcagtt tgggattgag ggtcataagg agccttttgt gaacatccca     360
gaggacacaa tccgtgaagc actaaaagtt gttcttgatg tcaggaacca cccagttata    420
attcactgta agcgtggaaa gcaccgaacg ggttgcttag taggatgcta tagaaaattg    480
caaaaatggt gcttgtcatc tgtctttgat gaataccaac gctttgcagc tgccaaagca    540
agagtttcag atcagaggtt tgtagagttg tttgatattt ccagcctgaa acattttcct    600
ataccttttt catgtttgaa gaggtga                                        627
```

<210> SEQ ID NO 6
<211> LENGTH: 208
<212> TYPE: PRT
<213> ORGANISM: glycine max

<400> SEQUENCE: 6

```
Met Gln Val Ala Ala Glu Leu Gln Arg Ala His His His Gln Arg
1               5                   10                  15

His Lys Gln Asp Thr Pro Met Cys Arg Gln Ile Gln Leu Thr Ile Ser
            20                  25                  30

Asp His Thr Thr Ala Gly Asp Asp Gly Glu Asp Leu Phe Ile Pro
        35                  40                  45

Pro Leu Asn Phe Ala Met Val Asp Asn Gly Ile Phe Arg Ser Gly Phe
    50                  55                  60

Pro Glu Pro Ala Asn Phe Ser Phe Leu Gln Thr Leu Gly Leu Arg Ser
65                  70                  75                  80

Ile Ile Tyr Leu Cys Pro Glu Pro Tyr Pro Glu Ala Asn Met Glu Phe
                85                  90                  95

Leu Lys Ser Asn Gly Ile Lys Leu Phe Gln Phe Gly Ile Glu Gly His
            100                 105                 110

Lys Glu Pro Phe Val Asn Ile Pro Glu Asp Thr Ile Arg Glu Ala Leu
        115                 120                 125

Lys Val Val Leu Asp Val Arg Asn His Pro Val Ile Ile His Cys Lys
    130                 135                 140

Arg Gly Lys His Arg Thr Gly Cys Leu Val Gly Cys Tyr Arg Lys Leu
145                 150                 155                 160

Gln Lys Trp Cys Leu Ser Ser Val Phe Asp Glu Tyr Gln Arg Phe Ala
                165                 170                 175

Ala Ala Lys Ala Arg Val Ser Asp Gln Arg Phe Val Glu Leu Phe Asp
            180                 185                 190

Ile Ser Ser Leu Lys His Phe Pro Ile Pro Phe Ser Cys Leu Lys Arg
        195                 200                 205
```

<210> SEQ ID NO 7
<211> LENGTH: 678
<212> TYPE: DNA
<213> ORGANISM: Oryza sativa

<400> SEQUENCE: 7

```
atgaagctgg aggtgatgcc gaagcagagg gccatggagg ccgagcagag ggaggaggcc    60
atggagatga gcgggctcga gctgtggaag cacgagaagc ccgcgtccat ggtggtgttc   120
ctcccgccgc cgccgccgcc gccgcttgtg ccggcggcgg cggccgcggc cgcggcggcg   180
tgtggtgagg aggcgacgct ggtgccaccg ctcaacttcg cgatggtcga cgacggcatc   240
ttccgctccg gcttccccgc ggccgccaac ttccggttcc tcaagtcgct caacctccgc   300
```

```
tccatcgtgt acctgtgccc ggagccgtac ccggagacga acgcggagtt cctcgccaag    360
aacgggatca agctccacca gttcggaatc gaggggcgca aggaaccatt cgtcaacatc    420
cctgacgaca aaattcgaga ggcgctcaaa gttgtcctag acgtaaaaaa ccaacctctg    480
cttattcact gcaagagagg caagcaccgc accggctgcg tcgtggggtg cttgaggaag    540
cttcagaaat ggtgcttgtc ttcagtgttc gacgagtacc agcgcttcgc cgctgcgaag    600
gcgaggagca ccgatcagag attcatggag ctgttcgaca tctcaagctt gaagcacctg    660
acagcttcac attgttaa                                                   678
```

<210> SEQ ID NO 8
<211> LENGTH: 225
<212> TYPE: PRT
<213> ORGANISM: oryza sativa

<400> SEQUENCE: 8

```
Met Lys Leu Glu Val Met Pro Lys Gln Arg Ala Met Glu Ala Glu Gln
1               5                   10                  15

Arg Glu Glu Ala Met Glu Met Ser Gly Leu Glu Leu Trp Lys His Glu
            20                  25                  30

Lys Pro Ala Ser Met Val Val Phe Leu Pro Pro Pro Pro Pro Pro Pro
        35                  40                  45

Leu Val Pro Ala Ala Ala Ala Ala Ala Ala Ala Cys Gly Glu Glu
    50                  55                  60

Ala Thr Leu Val Pro Pro Leu Asn Phe Ala Met Val Asp Asp Gly Ile
65                  70                  75                  80

Phe Arg Ser Gly Phe Pro Ala Ala Asn Phe Arg Phe Leu Lys Ser
                85                  90                  95

Leu Asn Leu Arg Ser Ile Val Tyr Leu Cys Pro Glu Pro Tyr Pro Glu
                100                 105                 110

Thr Asn Ala Glu Phe Leu Ala Lys Asn Gly Ile Lys Leu His Gln Phe
            115                 120                 125

Gly Ile Glu Gly Arg Lys Glu Pro Phe Val Asn Ile Pro Asp Asp Lys
    130                 135                 140

Ile Arg Glu Ala Leu Lys Val Val Leu Asp Val Lys Asn Gln Pro Leu
145                 150                 155                 160

Leu Ile His Cys Lys Arg Gly Lys His Arg Thr Gly Cys Val Val Gly
                165                 170                 175

Cys Leu Arg Lys Leu Gln Lys Trp Cys Leu Ser Ser Val Phe Asp Glu
            180                 185                 190

Tyr Gln Arg Phe Ala Ala Ala Lys Ala Arg Ser Thr Asp Gln Arg Phe
        195                 200                 205

Met Glu Leu Phe Asp Ile Ser Ser Leu Lys His Leu Thr Ala Ser His
    210                 215                 220

Cys
225
```

<210> SEQ ID NO 9
<211> LENGTH: 537
<212> TYPE: DNA
<213> ORGANISM: Gossypium hirsutum

<400> SEQUENCE: 9

```
atgtgcagaa ccatagaaga agatgccctc gccgttgacc accacgtcga catgtcgtcg    60
tcgacttcag atgacctcaa cttgattcct cctttgaact ttgctatagt tgacaatggc    120
```

| | | |
|---|---|---|
| atcttcaggt ctggtttccc tgattctgcc aacttctctt ttcttcaaac gcttaagctc | | 180 |
| acctccatca tatatctgtg tcctgaacca tacccagaag ccaacactga gttttaaag | | 240 |
| tccgatggaa tcaagctttt tcagtttgga attgaaagtt acaaggagcc atttgtaaat | | 300 |
| attccagagg atacgattcg tgaagcttta aggctcgtcc tcgatgttag gaatcaccca | | 360 |
| gttttaattc attgtaatcg agggaagcac cgaactggtc gtctggttgg atgcctgagg | | 420 |
| aagttgcaga gatggtgttt gtcatccgtg ttcgacgagt accaaaggct tgctgccgca | | 480 |
| aaagctagag tttcggatca gagcggagaa tgctcggtcc tgcataggat taattag | | 537 |

<210> SEQ ID NO 10
<211> LENGTH: 178
<212> TYPE: PRT
<213> ORGANISM: Gossypium hirsutum

<400> SEQUENCE: 10

```
Met Cys Arg Thr Ile Glu Glu Asp Ala Leu Ala Val Asp His His Val
1               5                   10                  15

Asp Met Ser Ser Thr Ser Asp Asp Leu Asn Leu Ile Pro Pro Leu
            20                  25                  30

Asn Phe Ala Ile Val Asp Asn Gly Ile Phe Arg Ser Gly Phe Pro Asp
        35                  40                  45

Ser Ala Asn Phe Ser Phe Leu Gln Thr Leu Lys Leu Thr Ser Ile Ile
    50                  55                  60

Tyr Leu Cys Pro Glu Pro Tyr Pro Glu Ala Asn Thr Glu Phe Leu Lys
65                  70                  75                  80

Ser Asp Gly Ile Lys Leu Phe Gln Phe Gly Ile Glu Ser Tyr Lys Glu
                85                  90                  95

Pro Phe Val Asn Ile Pro Glu Asp Thr Ile Arg Glu Ala Leu Arg Leu
            100                 105                 110

Val Leu Asp Val Arg Asn His Pro Val Leu Ile His Cys Asn Arg Gly
        115                 120                 125

Lys His Arg Thr Gly Arg Leu Val Gly Cys Leu Arg Lys Leu Gln Arg
    130                 135                 140

Trp Cys Leu Ser Ser Val Phe Asp Glu Tyr Gln Arg Leu Ala Ala Ala
145                 150                 155                 160

Lys Ala Arg Val Ser Asp Gln Ser Gly Glu Cys Ser Val Leu His Arg
                165                 170                 175

Ile Asn
```

<210> SEQ ID NO 11
<211> LENGTH: 2286
<212> TYPE: DNA
<213> ORGANISM: Arabidopsis thaliana

<400> SEQUENCE: 11

| | | |
|---|---|---|
| atggtgagtg acaagcatgt agaatcaaac caccgcaaac accgacggtc gttttcgccg | | 60 |
| tccgacgagg tcttttaaatc tccgaagcgg cacaagtccc gtcatcacca tcgcaggcat | | 120 |
| ggccaccgtc atcatcgtga tgaggaagtt caatataacg atgatgagaa tgttaacggt | | 180 |
| ggtgatcttg atatggaaga aggtgagata ttaggaaaag aagggattgg ggagacattg | | 240 |
| aagaagaaat tagagtccgt cgacgagttt ggggatataa atctggtca attccgggag | | 300 |
| aataatctgg ggaaaatca gcggagggaa agaatgtg agaaaagaaa agagatagag | | 360 |
| cctgaccgtg aaaggagaaa agagagggga agcgttgata gagatagcag gggagacagg | | 420 |

```
gaaaaagatt acctacggga tagagacaac gacagaggta ggagtagaga taaagccagg      480
tatagtagta gagagagggg gagggagaat gaaagagaga gacggagtga aaaagatagg      540
gataaaggac gagaattcca gagtgataga gagaagcata aaagtcttga tgatggatat      600
ggtgaagtga ggcataaaca ttctggacac tcaagacatg atgcggaaga tgacttagag      660
ttaagaagcc caacttctgt aaatggccat gatcctaaca gtggcgatgt caaagaaact      720
cggggaaatg ttgaaggac cagaattgat aatgatgata aggtgacgt tgttgtttgg       780 gaagttgaac aagaagatga agagctaaat ttaatcgagg aaagcaggag gagaacgcaa      840
gccataatgg agaaatataa gaaaagttg gagcagcaaa acggattttc ttctcatgat       900
cttgagctag caaacattcc caagcagtcc tctactgtgg cagatgttct ggaagtggt       960 actctggggc ctgttacttc tgcagttaat caagctaaag ctgggttgga tattgatgcc     1020
gtagatggtg aagtcgccaa gctttcatcg gcagttgggg aatcacctgc acagcttgta     1080
atttcagact cagataggac actagcttcc acagggcttg gggaaggcag cccaaaggat     1140
aaaatatcag atgacatgtt cactgatgat atctttgggg agtctccagc tgatagtcag     1200
aaaatgggct atctgcgagg gaaagggaat ggcattccta ttgtaaggag tggactcgac     1260
gataattggg atgatgcaga aggttattac agttatcaat taggggaact acttgatgat     1320
agatatgaaa tcatggctac tcatggaaaa ggtgtcttct ctaccgtggt gcgggcaaaa     1380
gacacaaaag ctgaactagg tgaacctgag gaagtggcta taaaaattat tcggaacaat     1440
gagacaatgc ataaggccgg ccagactgag attcagatat tgaagaagct agctggctct     1500
gacccagaga ataagcgcca ctgcgttcgt tttctttcaa cttttaagta taggaaccac     1560 cttttgcttgg tgtttgagtc tcttcatctg aatctccgtg agattgtgaa gaagtatggt     1620
cgcaacattg gtattcaact atctggtgtt agagtgtatg caacgcagtt attcatatcc     1680
cttaaacatc tcaagaactg tggggttctt cactgcgata taaagcctga caacatgctg     1740
gtgaatgagg gaagaaacac gttaaagctt tgtgactttg gtagtgcaat gttttgctggt     1800 acaaacgaag ttacaccata tcttgttagt cgcttctaca gagctccaga ataattctt     1860 ggacttcccct acgaccatcc gttagatata tggtcagttg gttgctgtct gtatgagctt     1920
tttagcggga aaattatgtt ccctggctcc acaaacaatg aaatgttacg cctgcatatg     1980
gaactgaaag gtgccttccc taaaaagatg cttcgcaagg gagcatttat cgatcagcac     2040
tttgataagg acttatgctt ctatgctaca gaggaggata gtgttactag aaagacaaca     2100
aagagaatga tggtaaacat aaagccaaaa gaatttggtt cagtaattaa acaacgttat     2160
aaggatgaag atagcaagtt gttggttcat ttcagggatc ttctagacag aattttcata     2220
cttgatcctc agaagagaat tacagtgtca caggcattag ctcacccatt catcacgggc     2280
aagtga                                                                2286
```

<210> SEQ ID NO 12
<211> LENGTH: 761
<212> TYPE: PRT
<213> ORGANISM: Arabidopsis thaliana

<400> SEQUENCE: 12

Met Val Ser Asp Lys His Val Glu Ser Asn His Arg Lys His Arg Arg
1               5                   10                  15

Ser Phe Ser Pro Ser Asp Glu Val Phe Lys Ser Pro Lys Arg His Lys
            20                  25                  30

```
Ser Arg His His Arg Arg His Gly His Arg His Arg Asp Glu
    35                  40                  45
Glu Val Gln Tyr Asn Asp Asp Glu Asn Val Asn Gly Gly Asp Leu Asp
50                      55                  60
Met Glu Glu Gly Glu Ile Leu Gly Lys Glu Gly Ile Gly Glu Thr Leu
65                  70                  75                  80
Lys Lys Lys Leu Glu Ser Val Asp Glu Phe Gly Asp Ile Lys Ser Gly
                85                  90                  95
Gln Phe Arg Glu Asn Asn Leu Gly Arg Asn Gln Arg Arg Glu Arg Glu
            100                 105                 110
Cys Glu Lys Arg Lys Glu Ile Glu Pro Asp Arg Glu Arg Arg Lys Glu
        115                 120                 125
Arg Gly Ser Val Asp Arg Asp Ser Arg Gly Asp Arg Glu Lys Asp Tyr
    130                 135                 140
Leu Arg Asp Arg Asp Asn Asp Arg Gly Arg Ser Arg Asp Lys Ala Arg
145                 150                 155                 160
Tyr Ser Ser Arg Glu Arg Gly Arg Glu Asn Glu Arg Glu Arg Arg Ser
                165                 170                 175
Glu Lys Asp Arg Asp Lys Gly Arg Glu Phe Gln Ser Asp Arg Glu Lys
            180                 185                 190
His Lys Ser Leu Asp Asp Gly Tyr Gly Glu Val Arg His Lys His Ser
        195                 200                 205
Gly His Ser Arg His Asp Ala Glu Asp Asp Leu Glu Leu Arg Ser Pro
    210                 215                 220
Thr Ser Val Asn Gly His Asp Pro Asn Ser Gly Asp Val Lys Glu Thr
225                 230                 235                 240
Arg Gly Asn Val Glu Arg Thr Arg Ile Asp Asn Asp Asp Lys Gly Asp
                245                 250                 255
Val Val Val Trp Glu Val Gln Glu Asp Glu Leu Asn Leu Ile
            260                 265                 270
Glu Glu Ser Arg Arg Arg Thr Gln Ala Ile Met Glu Lys Tyr Lys Lys
        275                 280                 285
Lys Leu Glu Gln Gln Asn Gly Phe Ser Ser His Asp Leu Glu Leu Ala
    290                 295                 300
Asn Ile Pro Lys Gln Ser Ser Thr Val Ala Asp Val Leu Gly Ser Gly
305                 310                 315                 320
Thr Leu Gly Pro Val Thr Ser Ala Val Asn Gln Ala Lys Ala Gly Leu
                325                 330                 335
Asp Ile Asp Ala Val Asp Gly Glu Val Ala Lys Leu Ser Ser Ala Val
            340                 345                 350
Gly Glu Ser Pro Ala Gln Leu Val Ile Ser Asp Ser Asp Arg Thr Leu
        355                 360                 365
Ala Ser Thr Gly Leu Gly Glu Gly Ser Pro Lys Asp Lys Ile Ser Asp
    370                 375                 380
Asp Met Phe Thr Asp Asp Ile Phe Gly Glu Ser Pro Ala Asp Ser Gln
385                 390                 395                 400
Lys Met Gly Tyr Leu Arg Gly Lys Gly Asn Gly Ile Pro Ile Val Arg
                405                 410                 415
Ser Gly Leu Asp Asp Asn Trp Asp Asp Ala Glu Gly Tyr Tyr Ser Tyr
            420                 425                 430
Gln Leu Gly Glu Leu Leu Asp Asp Arg Tyr Glu Ile Met Ala Thr His
        435                 440                 445
Gly Lys Gly Val Phe Ser Thr Val Val Arg Ala Lys Asp Thr Lys Ala
```

```
                450           455           460
Glu Leu Gly Glu Pro Glu Val Ala Ile Lys Ile Arg Asn Asn
465                 470                 475                 480

Glu Thr Met His Lys Ala Gly Gln Thr Glu Ile Gln Ile Leu Lys Lys
                485                 490                 495

Leu Ala Gly Ser Asp Pro Glu Asn Lys Arg His Cys Val Arg Phe Leu
            500                 505                 510

Ser Thr Phe Lys Tyr Arg Asn His Leu Cys Leu Val Phe Glu Ser Leu
        515                 520                 525

His Leu Asn Leu Arg Glu Ile Val Lys Lys Tyr Gly Arg Asn Ile Gly
    530                 535                 540

Ile Gln Leu Ser Gly Val Arg Val Tyr Ala Thr Gln Leu Phe Ile Ser
545                 550                 555                 560

Leu Lys His Leu Lys Asn Cys Gly Val Leu His Cys Asp Ile Lys Pro
                565                 570                 575

Asp Asn Met Leu Val Asn Glu Gly Arg Asn Thr Leu Lys Leu Cys Asp
            580                 585                 590

Phe Gly Ser Ala Met Phe Ala Gly Thr Asn Glu Val Thr Pro Tyr Leu
        595                 600                 605

Val Ser Arg Phe Tyr Arg Ala Pro Glu Ile Ile Leu Gly Leu Pro Tyr
    610                 615                 620

Asp His Pro Leu Asp Ile Trp Ser Val Gly Cys Cys Leu Tyr Glu Leu
625                 630                 635                 640

Phe Ser Gly Lys Ile Met Phe Pro Gly Ser Thr Asn Asn Glu Met Leu
                645                 650                 655

Arg Leu His Met Glu Leu Lys Gly Ala Phe Pro Lys Lys Met Leu Arg
            660                 665                 670

Lys Gly Ala Phe Ile Asp Gln His Phe Asp Lys Asp Leu Cys Phe Tyr
        675                 680                 685

Ala Thr Glu Glu Asp Ser Val Thr Arg Lys Thr Thr Lys Arg Met Met
    690                 695                 700

Val Asn Ile Lys Pro Lys Glu Phe Gly Ser Val Ile Lys Gln Arg Tyr
705                 710                 715                 720

Lys Asp Glu Asp Ser Lys Leu Leu Val His Phe Arg Asp Leu Leu Asp
                725                 730                 735

Arg Ile Phe Ile Leu Asp Pro Gln Lys Arg Ile Thr Val Ser Gln Ala
            740                 745                 750

Leu Ala His Pro Phe Ile Thr Gly Lys
        755                 760

<210> SEQ ID NO 13
<211> LENGTH: 2862
<212> TYPE: DNA
<213> ORGANISM: zea mays

<400> SEQUENCE: 13
atggctgccg gcggagagct ctccccctcc ccgtgccccc cgcatcccc catcaagcat      60 tctcgctcac ccgacgatgc ccagcccgac gcatccccga agcgtcgcaa gcgccaccat    120
caccgccgcc accaccacca ccgtcggcac cgtcacgccg attccccggt acccgtggca    180
gccgacgaag aggtagagga gggggagata ctcgaagatg ccaccgccgc ctctgccatg    240
gaggtcgatg ctgagtccgc cgccccagag gctttccttg ctccggagca ctttggtaat    300
ggtgctgata cagactcaaa cacagatgca accaagatgc aagctcctgc tctgcctacc    360
```

```
cttccatcct cagaagatgg aaggaggtca cttcatgatg cccctgagtc tgaaagagga    420
gatattcttt caagtgatgt tgaggacaac aaaggacatg aacgaaggca agacaaaac    480 cgttctaaat ctccaaagtc tagaagggag aaggaaagga ggcacaaaga tgaccatcac    540
acttcatctt caaaagatta tcattccaga aatcactcta gaacatctcc ttactcaagg    600
catcaaagtg aagctcattc gagagatctg tacttgagat atagagagaa aggtgattac    660
actaatggtt ctcgtgcaaa tcttagggat ggttctgatc atgagagcaa tgatcggaat    720
gggaagtctg gcagacatac gactaggacc cacgggagtg aaagagaaag gagcagcagc    780
catggtattc atgatagaca tggtgacagg tacagtgaca gacgtgccag ccaggaaagg    840
catagagacg ataggatata tagagacaaa atcgattcat tagaagctgc tcctaggcac    900
agagaaagaa gcaggagtca tagtagatcg gatccaaggg aaaatacacg tcttcgtgat    960
caaagcaggg agagggaaag acggagtggt agttcaaggc atagggatca tgacagcaag   1020
agggatacaa gtaaagatcg gcatagagaa tctgacaggg ttaacagtgc acatgaaagg   1080
gatagaggga gagaggctag ggacagggaa tggcataggg tcaagggaag tgaaactcat   1140
agagctaagg aaggacggga caaagttagc gataatgata ggcacaggga ttcaacacgc   1200
tcaaaatata gcgtgtctga tggttacaaa gagaggacaa gatctgggga aaaggtaga    1260 gatgctgacc ataaaaaccg gaagtttgaa gaaatgaagg aaaattctct caaggaggaa   1320
gatgaagagg agtaccaaga gaaaatagaa cagcagttag caatgcagga ggaagacgac   1380
cctgaaaaaa tcaaagagga agcaaggagg aggaaagaag ctatcatggc aaagtacagg   1440
cagcagcaat cgcagaaaga ggatatgaaa tctaaaccaa gtggcaatga tgaagaagta   1500
agagcaatgg atggaaacga agctatacat cagaaagatg atatcgatag cagctttatg   1560
ggcaatgtcg aagctgaaaa taagcatgat tcttcagagg tatttgatgg caagacaggc   1620
tttaatgtgg gaaggtctcc tgctcacaat tatgcttcaa ctagcacggg agcattcact   1680
gatgagagga caataggtgt ttcaggtctt ggagagggtt ctcccaagag tgagagatca   1740
gcagacatgt tttgtgatga catttttcgga gaatcaccca ccggaattag aaaattggga   1800
aaggatgatg gtttgcatat tgagagaaat gctcttcatg caactgggga tgatgcagat   1860
gggtactaca cttatcggtt cggagaattg ctggatggcc gttatgaaat catagcagca   1920
catgggaagg gtgtgttctc aacagttgtg cgggcaaaag atcttaaagc gagtaaggat   1980
gatcctgaag aagttgccat caaaattatt cgcaacaatg agacaatgta caaggctggt   2040
aagcaagagg tttcaatatt ggaaaaactt gcaagtgcgg accgtgagga caaacgccac   2100
tgcgtgcggt ttatttctag tttcatgtac cggaaccatc tttgcttagt ttttgaatct   2160
ctcaatatga tcttcgtgag gttttaaag aaatttggtc gtaatattgg gcttaaactg    2220
actgcggtga gggcatattc aaagcagctt ttcatcgccc tgaagcacct gaagaactgc   2280
aaagttttgc actgtgatat aaaaccagat aatatgctgg tgaatgaggc taagaatgtg   2340
ctcaaggtat gtgattttgg caacgctatg cttgctggta tgaatgaagt tacgccttat   2400
cttgtcagcc gtttctatcg ggcacctgag atcgttcttg gttagcccta tgatcaccct   2460
ttagacatgg ggtcagttgg ttgctgtcta tatgagcttt taccgggaa agtcttatttt   2520 cctggtccat caaacaatgc catgcttcgg cttcatatgg aattgaaggg tccattccct   2580
aagaagatgc ttcgaaaggg tgcctttact atgcaacact tcgatcaaga tctcaatttt   2640
catgctaccg aggaggatcc tgtgacaaaa acggctgtga aaggttaat tttgaacatt    2700 aaaccaaagg atgttggttc tttgtttccg aactttcctg gcgaggatcc aaaaatgcta   2760
```
tccagtttta aggatcttct tgataaaata tttacattag atccagaaaa gaggataact    2820
gtatcgcaag cacttagcca tccatttatc actggcaagt ga    2862

<210> SEQ ID NO 14
<211> LENGTH: 953
<212> TYPE: PRT
<213> ORGANISM: zea mays

<400> SEQUENCE: 14

Met Ala Ala Gly Gly Glu Leu Ser Pro Ser Pro Val Pro Pro Ala Ser
1               5                   10                  15

Pro Ile Lys His Ser Arg Ser Pro Asp Asp Ala Gln Pro Asp Ala Ser
            20                  25                  30

Pro Lys Arg Arg Lys Arg His His Arg Arg His His His His Arg
        35                  40                  45

Arg His Arg His Ala Asp Ser Pro Val Pro Val Ala Ala Asp Glu Glu
    50                  55                  60

Val Glu Glu Gly Glu Ile Leu Glu Asp Ala Thr Ala Ala Ser Ala Met
65                  70                  75                  80

Glu Val Asp Ala Glu Ser Ala Ala Pro Glu Ala Phe Leu Ala Pro Glu
                85                  90                  95

His Phe Gly Asn Gly Ala Asp Thr Asp Ser Asn Thr Asp Ala Thr Lys
            100                 105                 110

Met Gln Ala Pro Ala Leu Pro Thr Leu Pro Ser Ser Glu Asp Gly Arg
        115                 120                 125

Arg Ser Leu His Asp Ala Pro Glu Ser Glu Arg Gly Asp Ile Leu Ser
    130                 135                 140

Ser Asp Val Glu Asp Asn Lys Gly His Glu Arg Gln Arg Gln Asn
145                 150                 155                 160

Arg Ser Lys Ser Pro Lys Ser Arg Arg Glu Lys Glu Arg Arg His Lys
                165                 170                 175

Asp Asp His His Thr Ser Ser Ser Lys Asp Tyr His Ser Arg Asn His
            180                 185                 190

Ser Arg Thr Ser Pro Tyr Ser Arg His Gln Ser Glu Ala His Ser Arg
        195                 200                 205

Asp Leu Tyr Leu Arg Tyr Arg Glu Lys Gly Asp Tyr Thr Asn Gly Ser
    210                 215                 220

Arg Ala Asn Leu Arg Asp Gly Ser Asp His Glu Ser Asn Asp Arg Asn
225                 230                 235                 240

Gly Lys Ser Gly Arg His Thr Thr Arg Thr His Gly Ser Glu Arg Glu
                245                 250                 255

Arg Ser Ser His Gly Ile His Asp Arg His Gly Arg Tyr Ser
            260                 265                 270

Asp Arg Arg Ala Ser Gln Glu Arg His Arg Asp Asp Arg Ile Tyr Arg
        275                 280                 285

Asp Lys Ile Asp Ser Leu Glu Ala Ala Pro Arg His Arg Glu Arg Ser
    290                 295                 300

Arg Ser His Ser Arg Ser Asp Pro Arg Glu Asn Thr Arg Leu Arg Asp
305                 310                 315                 320

Gln Ser Arg Glu Arg Glu Arg Ser Gly Ser Ser Arg His Arg Asp
                325                 330                 335

His Asp Ser Lys Arg Asp Thr Ser Lys Asp Arg His Arg Glu Ser Asp
            340                 345                 350

-continued

Arg Val Asn Ser Ala His Glu Arg Asp Arg Gly Arg Glu Ala Arg Asp
        355                 360                 365

Arg Glu Trp His Arg Val Lys Gly Ser Glu Thr His Arg Ala Lys Glu
    370                 375                 380

Gly Arg Asp Lys Val Ser Asp Asn Asp Arg His Arg Asp Ser Thr Arg
385                 390                 395                 400

Ser Lys Tyr Ser Val Ser Asp Gly Tyr Lys Glu Arg Thr Arg Ser Gly
                405                 410                 415

Glu Lys Gly Arg Asp Ala Asp His Lys Asn Arg Lys Phe Glu Met
            420                 425                 430

Lys Glu Asn Ser Leu Lys Glu Glu Asp Glu Glu Tyr Gln Glu Lys
        435                 440                 445

Ile Glu Gln Gln Leu Ala Met Gln Glu Glu Asp Asp Pro Glu Lys Ile
    450                 455                 460

Lys Glu Glu Ala Arg Arg Lys Glu Ala Ile Met Ala Lys Tyr Arg
465                 470                 475                 480

Gln Gln Gln Ser Gln Lys Glu Asp Met Glu Ser Lys Pro Ser Gly Asn
                485                 490                 495

Asp Glu Glu Val Arg Ala Met Asp Gly Asn Glu Ala Ile His Gln Lys
            500                 505                 510

Asp Asp Ile Asp Ser Ser Phe Met Gly Asn Val Glu Ala Glu Asn Lys
        515                 520                 525

His Asp Ser Ser Glu Val Phe Asp Gly Lys Thr Gly Phe Asn Val Gly
    530                 535                 540

Arg Ser Pro Ala His Asn Tyr Ala Ser Thr Thr Gly Ala Phe Thr
545                 550                 555                 560

Asp Glu Arg Thr Ile Gly Val Ser Gly Leu Gly Glu Gly Ser Pro Lys
                565                 570                 575

Ser Glu Arg Ser Ala Asp Met Phe Cys Asp Asp Ile Phe Gly Glu Ser
            580                 585                 590

Pro Thr Gly Ile Arg Lys Leu Gly Lys Asp Asp Gly Leu His Ile Glu
        595                 600                 605

Arg Asn Ala Leu His Asp Asn Trp Asp Asp Ala Asp Gly Tyr Tyr Thr
    610                 615                 620

Tyr Arg Phe Gly Glu Leu Leu Asp Gly Arg Tyr Glu Ile Ile Ala Ala
625                 630                 635                 640

His Gly Lys Gly Val Phe Ser Thr Val Val Arg Ala Lys Asp Leu Lys
                645                 650                 655

Ala Ser Lys Asp Asp Pro Glu Glu Val Ala Ile Lys Ile Ile Arg Asn
            660                 665                 670

Asn Glu Thr Met Tyr Lys Ala Gly Lys Gln Glu Val Ser Ile Leu Glu
        675                 680                 685

Lys Leu Ala Ser Ala Asp Arg Glu Asp Lys Arg His Cys Val Arg Phe
    690                 695                 700

Ile Ser Ser Phe Met Tyr Arg Asn His Leu Cys Leu Val Phe Glu Ser
705                 710                 715                 720

Leu Asn Met Asn Leu Arg Glu Val Leu Lys Lys Phe Gly Arg Asn Ile
                725                 730                 735

Gly Leu Lys Leu Thr Ala Val Arg Ala Tyr Ser Lys Gln Leu Phe Ile
            740                 745                 750

Ala Leu Lys His Leu Lys Asn Cys Lys Val Leu His Cys Asp Ile Lys
        755                 760                 765

Pro Asp Asn Met Leu Val Asn Glu Ala Lys Asn Val Leu Lys Val Cys

```
                770               775               780
Asp Phe Gly Asn Ala Met Leu Ala Gly Met Asn Glu Val Thr Pro Tyr
785               790               795               800

Leu Val Ser Arg Phe Tyr Arg Ala Pro Glu Ile Val Leu Gly Leu Ala
              805               810               815

Tyr Asp His Pro Leu Asp Met Trp Ser Val Gly Cys Cys Leu Tyr Glu
              820               825               830

Leu Tyr Thr Gly Lys Val Leu Phe Pro Gly Pro Ser Asn Asn Ala Met
              835               840               845

Leu Arg Leu His Met Glu Leu Lys Gly Pro Phe Pro Lys Lys Met Leu
              850               855               860

Arg Lys Gly Ala Phe Thr Met Gln His Phe Asp Gln Asp Leu Asn Phe
865               870               875               880

His Ala Thr Glu Glu Asp Pro Val Thr Lys Thr Ala Val Arg Arg Leu
              885               890               895

Ile Leu Asn Ile Lys Pro Lys Asp Val Gly Ser Leu Phe Pro Asn Phe
              900               905               910

Pro Gly Glu Asp Pro Lys Met Leu Ser Ser Phe Lys Asp Leu Leu Asp
              915               920               925

Lys Ile Phe Thr Leu Asp Pro Glu Lys Arg Ile Thr Val Ser Gln Ala
              930               935               940

Leu Ser His Pro Phe Ile Thr Gly Lys
945               950

<210> SEQ ID NO 15
<211> LENGTH: 2784
<212> TYPE: DNA
<213> ORGANISM: glycine max

<400> SEQUENCE: 15
atggccaccg atgcccgtga ctcgcgtcgc aagcatcacc gatcttcctc tccagaggac      60
gtggacagat cctcgaagcg tcacaagcac cgccataaca gccatcgcca ccgccacggg     120
agcaaaaagc gcgacgaaga ggttgaattc gatgatcgaa caattgctgc ggttccttct     180
ccaacttcgc acagatatct ccatgacgac gatgtggagg agggagagat ccttgaagat     240
gaggctctcg acggtgaggt tggaaaaaag gagacggaat ctgatgttga acccggtgaa     300
atcaaggtga caggagatcg agatgttcga tctgataatc aaaattcgga ccccctcact     360
aaaatttcag aaactagaaa tgaagacatt agggatgata aatttattag tcctgcaatt     420
gatgcacaag atgatgtctc tcctaatcgt tcaagttctg agactcgaga tggaaagcat     480
gctcaagctc gtacagatgg tgtgggcaat ggttatttgg atcctaaatc ttccaaaggg     540
gataagtggc agaatgggga acttggacat tttaaagggg aaaagtatag aatgtcagga     600
agttctcctt ctcatggtag atatagaagt cgatcaagat caattggtca tactagagac     660
aggtctcgct ctcgtagtat catagacgaa tatcctcatt ctaagagaag gcgctttgac     720
tatgaccatg atgaggaaag agtgagggca cgtggaaggg agcatgaggc cagggataga     780
gatgtggata gagacttgca cggagaaaag aagcaagagg aaactagcag gggtaaagag     840
attgagagcc gtgataggta tagaagggat atagaaaaag ataggagcag ggagagggag     900
gaggataggg acaggagaca agaaaaggaa agagatagga gctgggatac agtgatggag     960
agggatagga gaagggaaaa ggaaagagat agaagtaggg acagaataag aggtggcaag    1020
agagataaag acccagagaa tgaaagggat gataagcatc gggcaagaga taatattaag    1080
```

-continued

| | |
|---|---|
| aagagggaaa gacatgatga taaatatagg cacaaagata gagacactgc taatgataga | 1140 |
| tatagaaaac attcaaggca tgaagaaaat gaatatcgtt gggaaagaaa aagaaattct | 1200 |
| gataatcctg taaaggttta tagctcaatg ggaagtactg cagaagtggg tgaaagcaaa | 1260 |
| ctaacaagca gtgaggttga accagatgac ttagaggagg atacattaca attacctgag | 1320 |
| caagaagagg aagatctcaa caggatcaaa gaagagagta gaagaagaag ggaagcaata | 1380 |
| atggagaaat acaagaagca gcatcagcaa gtagaagaag cggttggaaa tgaaggaaac | 1440 |
| ggtattattt tccccatttc attaacgatc tgtaattatt cttacaagaa ggcagccatt | 1500 |
| cctaatgaca tctctgaagc tcgtgatggt aaaaatgatg atgctgatta tttggagcca | 1560 |
| tcatttgctg ttgggaaatc tcctgaaaat gtgaatgttg cttctaagaa gatgtctcct | 1620 |
| gctggaggtc tgggagaggg tactccaaag agtgaaaggt cagaggacaa gttttgtgat | 1680 |
| gatatatttg gtgagacgcc aacgggagtt cggaaatcag gaaaaggaga tggtttactg | 1740 |
| attgagaggg ctggcctaca tgacaattgg gacgatgcag agggttatta tagctatcgt | 1800 |
| attggtgaaa tacttgatgg ccgatatgaa gtcactgctg cacatgggag gggtgtcttt | 1860 |
| tcaacagttg ttcgcggaaa gaatctaaag atgggaaatg gtgagccaga agaagtagcc | 1920 |
| ataaaaatta ttcgtagtaa tgacaccatg tacaaggctg gtatgatgga attggtcata | 1980 |
| ttgaagaaat tagtaggtgc agatccagat gataagcgtc attgtgttcg tttcctttca | 2040 |
| agttttagat acaggaatca tctttgttta gttttttgaat ctctaaatat gaatctgcga | 2100 |
| gaggttttaa agaagtttgg tcgcaatatt ggccttaggc taacagctgt gagagcatac | 2160 |
| gcaaaacagc ttttttattgc tctgaagcat ctccggaact gtggtgttct tcattgtgat | 2220 |
| ataaagccag ataatatgtt ggtaaatgag tctaaaaatg ttttgaagct ttgtgacttt | 2280 |
| ggcaatgcca tgtttgctgg taaaaatgaa gttacaccat atcttgtgag tcgttttttat | 2340 |
| cgtgccccgg aaataatact tggcttgcca tatgatcatc cattggatat ttggtctgta | 2400 |
| ggttgttgtt tgtatgagtt gtatataggg aaggttcttt tcccaggtct tacaaacaat | 2460 |
| gacatgctac ggcttcacat ggaactgaag ggtccttttc caaagaagat gctgcgtaag | 2520 |
| ggagcattta ctgaacagca ttttgatcag gatctgaatt ttcttgctac tgaggaggat | 2580 |
| cctgtaacaa aaaagaccat aaagcggctg atactcaaca ttaagccaaa agatattggg | 2640 |
| acactcatta ctggctctcc tggggaggat ccaaaaatgt tagccaactt taaggatctt | 2700 |
| ctggaaaaag ttttttgtctt ggatccagac aagaggctga cagtgtcaca agctctgaac | 2760 |
| cacccattca tcactggcaa gtga | 2784 |

<210> SEQ ID NO 16
<211> LENGTH: 927
<212> TYPE: PRT
<213> ORGANISM: glycine max

<400> SEQUENCE: 16

Met Ala Thr Asp Ala Arg Asp Ser Arg Arg Lys His His Arg Ser Ser
1               5                   10                  15

Ser Pro Glu Asp Val Asp Arg Ser Ser Lys Arg His Lys His Arg His
                20                  25                  30

Asn Ser His Arg His Arg His Gly Ser Lys Lys Arg Asp Glu Glu Val
            35                  40                  45

Glu Phe Asp Asp Arg Thr Ile Ala Ala Val Pro Ser Pro Thr Ser His
        50                  55                  60

Arg Tyr Leu His Asp Asp Asp Val Glu Glu Gly Glu Ile Leu Glu Asp

```
                65                  70                  75                  80
            Glu Ala Leu Asp Gly Glu Val Gly Lys Lys Glu Thr Glu Ser Asp Val
                                85                  90                  95

Glu Pro Gly Glu Ile Lys Val Thr Gly Asp Arg Asp Val Arg Ser Asp
                                100                 105                 110

Asn Gln Asn Ser Glu Pro Leu Thr Lys Ile Ser Glu Thr Arg Asn Glu
                                115                 120                 125

Asp Ile Arg Asp Lys Phe Ile Ser Pro Ala Ile Asp Ala Gln Asp
                130                 135                 140

Asp Val Ser Pro Asn Arg Ser Ser Glu Thr Arg Asp Gly Lys His
            145                 150                 155                 160

Ala Gln Ala Arg Thr Asp Gly Val Gly Asn Gly Tyr Leu Asp Pro Lys
                                165                 170                 175

Ser Ser Lys Gly Asp Lys Trp Gln Asn Gly Glu Leu Gly His Phe Lys
                                180                 185                 190

Gly Glu Lys Tyr Arg Met Ser Gly Ser Ser Pro Ser His Gly Arg Tyr
                                195                 200                 205

Arg Ser Arg Ser Arg Ser Ile Gly His Thr Arg Asp Arg Ser Arg Ser
                210                 215                 220

Arg Ser Ile Ile Asp Glu Tyr Pro His Ser Lys Arg Arg Phe Asp
            225                 230                 235                 240

Tyr Asp His Asp Glu Glu Arg Val Arg Ala Arg Gly Arg Glu His Glu
                                245                 250                 255

Ala Arg Asp Arg Asp Val Asp Arg Asp Leu His Gly Glu Lys Lys Gln
                                260                 265                 270

Glu Glu Thr Ser Arg Gly Lys Glu Ile Glu Ser Arg Asp Arg Tyr Arg
                                275                 280                 285

Arg Asp Ile Glu Lys Asp Arg Ser Arg Glu Arg Glu Asp Arg Asp
                290                 295                 300

Arg Arg Gln Glu Lys Glu Arg Asp Arg Ser Trp Asp Thr Val Met Glu
            305                 310                 315                 320

Arg Asp Arg Arg Arg Glu Lys Glu Arg Asp Arg Ser Arg Asp Arg Ile
                                325                 330                 335

Arg Gly Gly Lys Arg Asp Lys Asp Pro Glu Asn Glu Arg Asp Asp Lys
                                340                 345                 350

His Arg Ala Arg Asp Asn Ile Lys Lys Arg Glu Arg His Asp Asp Lys
                                355                 360                 365

Tyr Arg His Lys Asp Arg Asp Thr Ala Asn Asp Arg Tyr Arg Lys His
                370                 375                 380

Ser Arg His Glu Glu Asn Glu Tyr Arg Trp Glu Arg Lys Arg Asn Ser
            385                 390                 395                 400

Asp Asn Pro Val Lys Val Tyr Ser Ser Met Gly Ser Thr Ala Glu Val
                                405                 410                 415

Gly Glu Ser Lys Leu Thr Ser Ser Glu Val Glu Pro Asp Asp Leu Glu
                                420                 425                 430

Glu Asp Thr Leu Gln Leu Pro Glu Gln Glu Glu Asp Leu Asn Arg
                435                 440                 445

Ile Lys Glu Glu Ser Arg Arg Arg Glu Ala Ile Met Glu Lys Tyr
            450                 455                 460

Lys Lys Gln His Gln Gln Val Glu Glu Ala Val Gly Asn Glu Gly Asn
            465                 470                 475                 480

Gly Ile Ile Phe Pro Ile Ser Leu Thr Ile Cys Asn Tyr Ser Tyr Lys
                                485                 490                 495
```

-continued

```
Lys Ala Ala Ile Pro Asn Asp Ile Ser Glu Ala Arg Asp Gly Lys Asn
            500                 505                 510
Asp Asp Ala Asp Tyr Leu Glu Pro Ser Phe Ala Val Gly Lys Ser Pro
            515                 520                 525
Glu Asn Val Asn Val Ala Ser Lys Lys Met Ser Pro Ala Gly Gly Leu
            530                 535                 540
Gly Glu Gly Thr Pro Lys Ser Glu Arg Ser Glu Asp Lys Phe Cys Asp
545                 550                 555                 560
Asp Ile Phe Gly Glu Thr Pro Thr Gly Val Arg Lys Ser Gly Lys Gly
                565                 570                 575
Asp Gly Leu Leu Ile Glu Arg Ala Gly Leu His Asp Asn Trp Asp Asp
                580                 585                 590
Ala Glu Gly Tyr Tyr Ser Tyr Arg Ile Gly Glu Ile Leu Asp Gly Arg
                595                 600                 605
Tyr Glu Val Thr Ala Ala His Gly Arg Gly Val Phe Ser Thr Val Val
            610                 615                 620
Arg Gly Lys Asn Leu Lys Met Gly Asn Gly Glu Pro Glu Glu Val Ala
625                 630                 635                 640
Ile Lys Ile Ile Arg Ser Asn Asp Thr Met Tyr Lys Ala Gly Met Asp
                645                 650                 655
Glu Leu Val Ile Leu Lys Lys Leu Val Gly Ala Asp Pro Asp Asp Lys
                660                 665                 670
Arg His Cys Val Arg Phe Leu Ser Ser Phe Arg Tyr Arg Asn His Leu
            675                 680                 685
Cys Leu Val Phe Glu Ser Leu Asn Met Asn Leu Arg Glu Val Leu Lys
            690                 695                 700
Lys Phe Gly Arg Asn Ile Gly Leu Arg Leu Thr Ala Val Arg Ala Tyr
705                 710                 715                 720
Ala Lys Gln Leu Phe Ile Ala Leu Lys His Leu Arg Asn Cys Gly Val
                725                 730                 735
Leu His Cys Asp Ile Lys Pro Asp Asn Met Leu Val Asn Glu Ser Lys
                740                 745                 750
Asn Val Leu Lys Leu Cys Asp Phe Gly Asn Ala Met Phe Ala Gly Lys
            755                 760                 765
Asn Glu Val Thr Pro Tyr Leu Val Ser Arg Phe Tyr Arg Ala Pro Glu
            770                 775                 780
Ile Ile Leu Gly Leu Pro Tyr Asp His Pro Leu Asp Ile Trp Ser Val
785                 790                 795                 800
Gly Cys Cys Leu Tyr Glu Leu Tyr Ile Gly Lys Val Leu Phe Pro Gly
                805                 810                 815
Leu Thr Asn Asn Asp Met Leu Arg Leu His Met Glu Leu Lys Gly Pro
            820                 825                 830
Phe Pro Lys Lys Met Leu Arg Lys Gly Ala Phe Thr Glu Gln His Phe
            835                 840                 845
Asp Gln Asp Leu Asn Phe Leu Ala Thr Glu Glu Asp Pro Val Thr Lys
            850                 855                 860
Lys Thr Ile Lys Arg Leu Ile Leu Asn Ile Lys Pro Lys Asp Ile Gly
865                 870                 875                 880
Thr Leu Ile Thr Gly Ser Pro Gly Glu Asp Pro Lys Met Leu Ala Asn
                885                 890                 895
Phe Lys Asp Leu Leu Glu Lys Val Phe Val Leu Asp Pro Asp Lys Arg
                900                 905                 910
```

```
Leu Thr Val Ser Gln Ala Leu Asn His Pro Phe Ile Thr Gly Lys
    915                 920                 925
```

<210> SEQ ID NO 17
<211> LENGTH: 2597
<212> TYPE: DNA
<213> ORGANISM: oryza sativa

<400> SEQUENCE: 17

| | | | | | |
|---|---|---|---|---|---|
| atggctgagg | aaccctcccc | ctcccccctcc | tcctcctgcg | ccaagcacca | ccgctctccc | 60 |
| gaccccgccg | accccgccgc | ctctccatga | actcagatgc | tgatgcaacc | gtgctgcatg | 120 |
| cttctcgctt | gcctactcat | tcatcctcaa | gggacgaaac | caagtcaaat | cacaccgccc | 180 |
| atgagcctga | gagtggaggc | gatgcagatg | ataccaaagg | ggatagacaa | agtcaaaggg | 240 |
| tgccaaaatc | accactattg | acaagggaga | agaaaggaa | gcacaaagat | gagcaccgca | 300 |
| aatcgtatcc | taaagattca | cattccaaag | agcagtctag | aagatcccct | tcaaggcacc | 360 |
| atagcagtca | agatcatgcc | aggcatcact | caaggtctag | atactggt | gctgaagcta | 420 |
| atggttcgcg | ggcaagtaca | agggaagatt | ctgaccgtga | cagcaacggc | agaaatagta | 480 |
| agcatggtag | gcatgcaacc | aggagtcgag | ataatgagac | agaaaggagc | agcagctatg | 540 |
| ctgttcgtga | tgaggcgtat | gatgagcggg | aaagatataa | gcatgaaaga | aggcatagaa | 600 |
| gcaacccagt | tgatagagac | aaagtggatt | tgcatgaact | aactcacagg | atagagaaa | 660 |
| ggagcagcag | tcgcagtaga | tctgatcgta | gggagagtgc | acatcacatt | cgtgatgaaa | 720 |
| gcagggagag | tgaaaggcgg | agtagtagtt | caaggcataa | agataatgag | agaagggata | 780 |
| gaagtaagga | tcgctataaa | gaatctgaca | aggttgacag | tggacatgaa | agggacaaaa | 840 |
| caagagatga | tagagacagg | ggacgacata | aggatttgga | agtagaaag | cggagaaatg | 900 |
| gagaagcaaa | ggacagggat | gacaggcaca | aggattctac | acgctcaaaa | tacagtactt | 960 |
| ctgatagtca | taaacaccgc | tcaagatcca | gggagagagg | tagagatgct | gaacgtagag | 1020 |
| gccagagatc | tgaagagctg | aaggagaata | cttcaggga | ggaggatgaa | gaggagtacc | 1080 |
| aagagaaaat | tgaacagcag | ttagcaatgc | aggaagaaga | ggaccctgaa | aaaattaagg | 1140 |
| aggaagcaag | gaggaggaaa | gaagctatta | tggcaaaata | caggcagcaa | caattgcaga | 1200 |
| agcagcagct | ggaatcttta | cctagaagta | atgatgaaga | agaagtggaa | atgaacagag | 1260 |
| gtgataatgc | agatctgaaa | ggtgataacg | atagcagatt | tgtggctagc | gaggaagctg | 1320 |
| aaaataagca | tgattcttca | gatgcaattg | ttggtgaaac | agacttcact | gtgggaaagt | 1380 |
| ctcctgctca | caatgatggt | gcaggaactt | tgggtaatca | gagaacaact | ggtgtttcag | 1440 |
| gtcttggaga | gggcactcca | aagagtgaga | gatcggcgga | tatgttttgt | gatgacattt | 1500 |
| ttggagaatc | acctgctggc | atccggaaat | tgggcaagga | tgatggtttg | cgcatcgaga | 1560 |
| aaaatgctct | tcatgacaac | tgggatgatg | ccgaggggta | ctatacttac | cgttttgggg | 1620 |
| aattgctgga | tgggcgctat | gagattacag | cagcacatgg | aaagggagtg | ttttcaacag | 1680 |
| ttgtccgagc | aaaagatctt | aaagctggga | aggatgatcc | cgaagaggtt | gctattaaga | 1740 |
| ttattcgcaa | caatgagaca | atgtacaagg | ctggtaagca | agaggtttca | atattagaaa | 1800 |
| aactggcaag | tgcggatcgt | gaagacaggc | gccactgcgt | gcggtttatt | tctagtttca | 1860 |
| tgtataggaa | ccatctttgc | ttagttttg | aatctctaaa | tatgaatctt | cgtgaggtac | 1920 |
| taaagaaatt | tggtcgcaat | atcggactta | aactaactgc | tgtgagggca | tattcaaagc | 1980 |
| agcttttcat | cgccctgaag | catctgaaaa | actgcaaagt | gctgcactgt | gatataaagc | 2040 |

```
cagataatat gctggtgaat gaggctaaga atgtgctgaa gctctgtgat tttggcaatg    2100
caatgcttgc tggaatgaac gaggttacac cttatcttgt gagccgtttc tatcgtgcac    2160
ctgagataat tcttgggtta ccctacgacc acccattaga catgtggtca gttggctgct    2220
gtctatatga actttacacc ggaaaagtcc tatttccagg tccatcaaat aatgacatgc    2280
ttcggcttca tatggaactg aagggcccct tccccaagaa aatgcttcga aagggtgcct    2340
ttacgatgca acattttgac caagatctca actttcatgc cactgaggag gatcctgtga    2400
ctaaaaaggc tgtgacaagg atgattttga acattaagcc aaaggatatt ggttccttga    2460
tttcaaactt ccctggcgag gatccaaaaa tgctatccaa ctttaaagat cttcttgaaa    2520
aaatatttgt cttagatcca gaaaagagga taaccatatc acaagcactt agccatccat    2580
ttatcactgg caagtga                                                  2597
```

<210> SEQ ID NO 18
<211> LENGTH: 836
<212> TYPE: PRT
<213> ORGANISM: oryza sativa

<400> SEQUENCE: 18

```
Met Asn Ser Asp Ala Asp Ala Thr Val Leu His Ala Ser Arg Leu Pro
1               5                   10                  15

Thr His Ser Ser Ser Arg Asp Glu Thr Lys Ser Asn His Thr Ala His
            20                  25                  30

Glu Pro Glu Ser Gly Gly Asp Ala Asp Thr Lys Gly Asp Arg Gln
        35                  40                  45

Ser Gln Arg Val Pro Lys Ser Pro Leu Leu Thr Arg Glu Lys Glu Arg
    50                  55                  60

Lys His Lys Asp Glu His Arg Lys Ser Tyr Pro Lys Asp Ser His Ser
65                  70                  75                  80

Lys Glu Gln Ser Arg Arg Ser Pro Ser Arg His His Ser Ser Gln Asp
                85                  90                  95

His Ala Arg His His Ser Arg Ser Arg Asp Thr Gly Ala Glu Ala Asn
            100                 105                 110

Gly Ser Arg Ala Ser Thr Arg Glu Asp Ser Asp Arg Asp Ser Asn Gly
        115                 120                 125

Arg Asn Ser Lys His Gly Arg His Ala Thr Arg Ser Arg Asp Asn Glu
    130                 135                 140

Thr Glu Arg Ser Ser Ser Tyr Ala Val Arg Asp Glu Ala Tyr Asp Glu
145                 150                 155                 160

Arg Glu Arg Tyr Lys His Glu Arg Arg His Arg Ser Asn Pro Val Asp
                165                 170                 175

Arg Asp Lys Val Asp Leu His Glu Leu Thr His Arg Ser Arg Glu Arg
            180                 185                 190

Ser Ser Ser Arg Ser Arg Ser Asp Arg Arg Glu Ser Ala His His Ile
        195                 200                 205

Arg Asp Glu Ser Arg Glu Ser Glu Arg Arg Ser Ser Ser Arg His
    210                 215                 220

Lys Asp Asn Glu Arg Arg Asp Arg Ser Lys Asp Arg Tyr Lys Glu Ser
225                 230                 235                 240

Asp Lys Val Asp Ser Gly His Glu Arg Asp Lys Thr Arg Asp Asp Arg
                245                 250                 255

Asp Arg Gly Arg His Lys Asp Leu Glu Ser Arg Lys Arg Asn Gly
            260                 265                 270
```

```
Glu Ala Lys Asp Arg Asp Arg His Lys Asp Ser Thr Arg Ser Lys
            275                 280                 285

Tyr Ser Thr Ser Asp Ser His Lys His Arg Ser Arg Ser Arg Glu Arg
            290                 295                 300

Gly Arg Asp Ala Glu Arg Arg Gly Gln Arg Ser Glu Glu Leu Lys Glu
305                 310                 315                 320

Asn Thr Phe Arg Glu Glu Asp Glu Glu Tyr Gln Glu Lys Ile Glu
                325                 330                 335

Gln Gln Leu Ala Met Gln Glu Glu Asp Pro Glu Lys Ile Lys Glu
            340                 345                 350

Glu Ala Arg Arg Arg Lys Glu Ala Ile Met Ala Lys Tyr Arg Gln Gln
            355                 360                 365

Gln Leu Gln Lys Gln Gln Leu Glu Ser Leu Pro Arg Ser Asn Asp Glu
    370                 375                 380

Glu Glu Val Glu Met Asn Arg Gly Asp Asn Ala Asp Leu Lys Gly Asp
385                 390                 395                 400

Asn Asp Ser Arg Phe Val Ala Ser Glu Glu Ala Glu Asn Lys His Asp
                405                 410                 415

Ser Ser Asp Ala Ile Val Gly Glu Thr Asp Phe Thr Val Gly Lys Ser
            420                 425                 430

Pro Ala His Asn Asp Gly Ala Gly Thr Leu Gly Asn Gln Arg Thr Thr
            435                 440                 445

Gly Val Ser Gly Leu Gly Glu Gly Thr Pro Lys Ser Glu Arg Ser Ala
            450                 455                 460

Asp Met Phe Cys Asp Asp Ile Phe Gly Glu Ser Pro Ala Gly Ile Arg
465                 470                 475                 480

Lys Leu Gly Lys Asp Asp Gly Leu Arg Ile Glu Lys Asn Ala Leu His
                485                 490                 495

Asp Asn Trp Asp Asp Ala Glu Gly Tyr Tyr Thr Tyr Arg Phe Gly Glu
            500                 505                 510

Leu Leu Asp Gly Arg Tyr Glu Ile Thr Ala Ala His Gly Lys Gly Val
            515                 520                 525

Phe Ser Thr Val Val Arg Ala Lys Asp Leu Lys Ala Gly Lys Asp Asp
    530                 535                 540

Pro Glu Glu Val Ala Ile Lys Ile Ile Arg Asn Asn Glu Thr Met Tyr
545                 550                 555                 560

Lys Ala Gly Lys Gln Glu Val Ser Ile Leu Glu Lys Leu Ala Ser Ala
                565                 570                 575

Asp Arg Glu Asp Arg Arg His Cys Val Arg Phe Ile Ser Ser Phe Met
            580                 585                 590

Tyr Arg Asn His Leu Cys Leu Val Phe Glu Ser Leu Asn Met Asn Leu
            595                 600                 605

Arg Glu Val Leu Lys Lys Phe Gly Arg Asn Ile Gly Leu Lys Leu Thr
    610                 615                 620

Ala Val Arg Ala Tyr Ser Lys Gln Leu Phe Ile Ala Leu Lys His Leu
625                 630                 635                 640

Lys Asn Cys Lys Val Leu His Cys Asp Ile Lys Pro Asp Asn Met Leu
                645                 650                 655

Val Asn Glu Ala Lys Asn Val Leu Lys Leu Cys Asp Phe Gly Asn Ala
            660                 665                 670

Met Leu Ala Gly Met Asn Glu Val Thr Pro Tyr Leu Val Ser Arg Phe
            675                 680                 685

Tyr Arg Ala Pro Glu Ile Ile Leu Gly Leu Pro Tyr Asp His Pro Leu
```

```
                690             695             700
Asp Met Trp Ser Val Gly Cys Cys Leu Tyr Glu Leu Tyr Thr Gly Lys
705             710             715             720

Val Leu Phe Pro Gly Pro Ser Asn Asn Asp Met Leu Arg Leu His Met
            725             730             735

Glu Leu Lys Gly Pro Phe Pro Lys Met Leu Arg Lys Gly Ala Phe
            740             745             750

Thr Met Gln His Phe Asp Gln Asp Leu Asn Phe His Ala Thr Glu Glu
        755             760             765

Asp Pro Val Thr Lys Lys Ala Val Thr Arg Met Ile Leu Asn Ile Lys
        770             775             780

Pro Lys Asp Ile Gly Ser Leu Ile Ser Asn Phe Pro Gly Glu Asp Pro
785             790             795             800

Lys Met Leu Ser Asn Phe Lys Asp Leu Leu Glu Lys Ile Phe Val Leu
            805             810             815

Asp Pro Glu Lys Arg Ile Thr Ile Ser Gln Ala Leu Ser His Pro Phe
            820             825             830

Ile Thr Gly Lys
        835

<210> SEQ ID NO 19
<211> LENGTH: 1134
<212> TYPE: DNA
<213> ORGANISM: gossypium hirsutum

<400> SEQUENCE: 19
ggcacgaggc cggttataag gagtggtctt catgacaatt gggatgacgc tgaaggatat      60
tatagctatc gatttggtga atacttgat ggccgatatg aagtaactgc tgctcatgga      120
aaaggagttt tttcaacggt tgtacgtgcg aaggatctta aggctggtgc tactgggggg      180
gaagaagtag ctataaagat cattcgtaat aatgaaacga tgcacaaggc tggtcagctg      240
gaggttcaaa tattgaaaaa attagcaggt gcagatccag atgataagcg acattgtgtt      300
cgttttttgt caagtttcaa gtacaggaat catctttgtt tagttttga gtctcttcat      360 atgaatctgc gtgaagttct caagaagttt ggtcgcaata ttggtcttaa actaactgct      420
gtcagggctt atgctaagca acttttttatt gcgcttaagc atctaaaaaa ctgtggtgtt      480
cttcattgtg atataaagcc tgataacatg ctggtaaatg aggcaaaaaa tgtgctgaag      540
ctttgtgatt tggtaatgc catgtttgct ggtaaaaatg aaattacacc ataccttgtt      600
agccgctttt atcgtgcacc agaaattatt cttggtttgc cttacgatca tccaatggat      660
atctggtctg ttggttgctg tttgtatgag ctatatactg gaaaagttct tttccctggt      720
ccaacaaaca atgacatgct acgtcttcat atggaactca aggtcctttt ccaaagaag      780 atgttgcgta agggagcatt tacagaacaa cactttgatc aagatctgaa ttttcatgct      840
acagaagagg atcctgttac taaaaagagt ataagagga tgattcttaa cataaagcca      900
aaagatatca gttcaattat tgttggctct ccaggtgagg atccaaagat ggtagccaac      960
ttcaaagacc ttctagaaaa aattttttgtg cttgatccag agaagagaat gacagttact     1020
caggcattgg ctcatccatt catcacgggc aagtggaaac atgttgctga ttttatgtct     1080
ccagaaatgt gttgcgctag atatttgtac attatgaccc taactcatat ttag            1134

<210> SEQ ID NO 20
<211> LENGTH: 377
<212> TYPE: PRT
```

<213> ORGANISM: gossupium hirsutum

<400> SEQUENCE: 20

| | | | | | | | | | | | | | | |
|---|---|---|---|---|---|---|---|---|---|---|---|---|---|---|
| Gly | Thr | Arg | Pro | Val | Ile | Arg | Ser | Gly | Leu | His | Asp | Asn | Trp | Asp |
| 1 | | | | 5 | | | | | 10 | | | | | 15 |
| Ala | Glu | Gly | Tyr | Tyr | Ser | Tyr | Arg | Phe | Gly | Glu | Ile | Leu | Asp | Gly | Arg |
| | | | 20 | | | | | 25 | | | | | 30 | | |
| Tyr | Glu | Val | Thr | Ala | Ala | His | Gly | Lys | Gly | Val | Phe | Ser | Thr | Val | Val |
| | | 35 | | | | | 40 | | | | | 45 | | | |
| Arg | Ala | Lys | Asp | Leu | Lys | Ala | Gly | Ala | Thr | Gly | Gly | Glu | Val | Ala |
| 50 | | | | | 55 | | | | | 60 | | | | | |
| Ile | Lys | Ile | Ile | Arg | Asn | Asn | Glu | Thr | Met | His | Lys | Ala | Gly | Gln | Leu |
| 65 | | | | | 70 | | | | | 75 | | | | | 80 |
| Glu | Val | Gln | Ile | Leu | Lys | Lys | Leu | Ala | Gly | Ala | Asp | Pro | Asp | Lys |
| | | | | 85 | | | | | 90 | | | | | 95 |
| Arg | His | Cys | Val | Arg | Phe | Leu | Ser | Ser | Phe | Lys | Tyr | Arg | Asn | His | Leu |
| | | | 100 | | | | | 105 | | | | | 110 | | |
| Cys | Leu | Val | Phe | Glu | Ser | Leu | His | Met | Asn | Leu | Arg | Glu | Val | Leu | Lys |
| | | | 115 | | | | | 120 | | | | | 125 | | |
| Lys | Phe | Gly | Arg | Asn | Ile | Gly | Leu | Lys | Leu | Thr | Ala | Val | Arg | Ala | Tyr |
| 130 | | | | | 135 | | | | | 140 | | | | | |
| Ala | Lys | Gln | Leu | Phe | Ile | Ala | Leu | Lys | His | Leu | Lys | Asn | Cys | Gly | Val |
| 145 | | | | | 150 | | | | | 155 | | | | | 160 |
| Leu | His | Cys | Asp | Ile | Lys | Pro | Asp | Asn | Met | Leu | Val | Asn | Glu | Ala | Lys |
| | | | | 165 | | | | | 170 | | | | | 175 | |
| Asn | Val | Leu | Lys | Leu | Cys | Asp | Phe | Gly | Asn | Ala | Met | Phe | Ala | Gly | Lys |
| | | | 180 | | | | | 185 | | | | | 190 | | |
| Asn | Glu | Ile | Thr | Pro | Tyr | Leu | Val | Ser | Arg | Phe | Tyr | Arg | Ala | Pro | Glu |
| | | | 195 | | | | | 200 | | | | | 205 | | |
| Ile | Ile | Leu | Gly | Leu | Pro | Tyr | Asp | His | Pro | Met | Asp | Ile | Trp | Ser | Val |
| | 210 | | | | | 215 | | | | | 220 | | | | |
| Gly | Cys | Cys | Leu | Tyr | Glu | Leu | Tyr | Thr | Gly | Lys | Val | Leu | Phe | Pro | Gly |
| 225 | | | | | 230 | | | | | 235 | | | | | 240 |
| Pro | Thr | Asn | Asn | Asp | Met | Leu | Arg | Leu | His | Met | Glu | Leu | Lys | Gly | Pro |
| | | | | 245 | | | | | 250 | | | | | 255 | |
| Phe | Pro | Lys | Lys | Met | Leu | Arg | Lys | Gly | Ala | Phe | Thr | Glu | Gln | His | Phe |
| | | | 260 | | | | | 265 | | | | | 270 | | |
| Asp | Gln | Asp | Leu | Asn | Phe | His | Ala | Thr | Glu | Glu | Asp | Pro | Val | Thr | Lys |
| | | | 275 | | | | | 280 | | | | | 285 | | |
| Lys | Ser | Ile | Lys | Arg | Met | Ile | Leu | Asn | Ile | Lys | Pro | Lys | Asp | Ile | Ser |
| | 290 | | | | | 295 | | | | | 300 | | | | |
| Ser | Ile | Ile | Val | Gly | Ser | Pro | Gly | Glu | Asp | Pro | Lys | Met | Val | Ala | Asn |
| 305 | | | | | 310 | | | | | 315 | | | | | 320 |
| Phe | Lys | Asp | Leu | Leu | Glu | Lys | Ile | Phe | Val | Leu | Asp | Pro | Glu | Lys | Arg |
| | | | | 325 | | | | | 330 | | | | | 335 | |
| Met | Thr | Val | Thr | Gln | Ala | Leu | Ala | His | Pro | Phe | Ile | Thr | Gly | Lys | Trp |
| | | | 340 | | | | | 345 | | | | | 350 | | |
| Lys | His | Val | Ala | Asp | Phe | Met | Ser | Pro | Glu | Met | Cys | Cys | Ala | Arg | Tyr |
| | | | 355 | | | | | 360 | | | | | 365 | | |
| Leu | Tyr | Ile | Met | Thr | Leu | Thr | His | Ile |
| | 370 | | | | | 375 | | |

<210> SEQ ID NO 21
<211> LENGTH: 1413

```
<212> TYPE: DNA
<213> ORGANISM: Arabidopsis thaliana

<400> SEQUENCE: 21
atgggttatc tctcttgcaa cggcgaatcc gccgtcgcaa tctgcgatac ttataactgg     60
aatcctcgtc gacgatctaa agtaccggag aaacgtcatc ctcctaagct tcgggttttc    120
aactacgacg aactcgccgt cgctactaac ggcttctccg ccataacttt cctcggaaaa    180
ggaagtcacg gcagagttta caaagcagtt ctcgacgacg gaaagcttct cgccgccgtc    240
aagagaacaa caatcaccac taccgttggt aataacaata caacgtgagt caggtagac     300
aatgagatcg agattctttc acgggttcgt caccgttgga tggtcaactt aatcggttac    360
tgcgttgacc accggaggaa aacaaagctg ttagtcgtcg agtacatgcc taacggtacg    420
cttcacgatc agttacattc tcgtagttcg ttagattcac ggttaagtag ttggaatcgg    480
agaattaaac acgcgcttca gatcgcgatt gctgtccacg ctcttcacac cgcagagact    540
caagtgatcc accgtgacat taaatcgtgt aacgttttaa tagacggtga cggtaacgct    600
aggttagctg atttcggatt agcattgatc ggaaacgttg acgatgagcg tttgaaatat    660
actccgccgg cgggtacgtt gggatatttta gatccgtcgt acttagcacc ggcggacttg    720
acggctaaga gcgatgtttt cagctttggg atattgttgt tggagattat tagtggtaga    780
gaagccattg atttgaatta tagtccgtcg tgtatcgttg attgggcggt gccgcttatc    840
aaacgcggcg attacgacgc gatttgtgat ttgaagatta agaaccgtcc ttattacgcc    900
gtgattcgga agtggccgt tatggcggct aggtgtgtta gatcgacggc gaagaaacgt    960
ccagatatgt tagaggttgt tgagtgtttg aaaacggtga ggcagttatc tccggcgtgg   1020
aataaactgc ggcggaggag tgaagagaga tcggaaaatg tttggcggt tgaggaagag   1080
aaggaagaga ttcatgtgag gattgtgaga ggaggaagca ggaagaatcg gaaggtatcg   1140
aacgtgacga cgagtgtgga tgatgtttac gagagattag ttccggagga aacgctgccg   1200
tttcgtcgtc ggaattttgt gctgagatcg agatcagtag gagcgaaagt tggaccggat   1260
ccatacgacg ggtttggtga tgagacggtg gttacaatga gattacttat tgagaaagaa   1320
agaccggtga cgacggcagc gatgaggctg agtaagtcga ggtcggtggg gattgtacgt   1380
agtcataaaa cggcgtcgcg gaagagatac tga                                1413

<210> SEQ ID NO 22
<211> LENGTH: 470
<212> TYPE: PRT
<213> ORGANISM: Arabidopsis thaliana

<400> SEQUENCE: 22

Met Gly Tyr Leu Ser Cys Asn Gly Glu Ser Ala Val Ala Ile Cys Asp
1               5                   10                  15

Thr Tyr Asn Trp Asn Pro Arg Arg Ser Lys Val Pro Glu Lys Arg
            20                  25                  30

His Pro Pro Lys Leu Arg Val Phe Asn Tyr Asp Glu Leu Ala Val Ala
        35                  40                  45

Thr Asn Gly Phe Ser Ala Asn Asn Phe Leu Gly Lys Gly Ser His Gly
    50                  55                  60

Arg Val Tyr Lys Ala Val Leu Asp Asp Gly Lys Leu Leu Ala Ala Val
65                  70                  75                  80

Lys Arg Thr Thr Ile Thr Thr Thr Val Gly Asn Asn Asn Asn Asn Val
                85                  90                  95
```

Ser Gln Val Asp Asn Glu Ile Glu Ile Leu Ser Arg Val Arg His Arg
            100                 105                 110

Trp Met Val Asn Leu Ile Gly Tyr Cys Val Asp His Arg Arg Lys Thr
        115                 120                 125

Lys Leu Leu Val Val Glu Tyr Met Pro Asn Gly Thr Leu His Asp Gln
    130                 135                 140

Leu His Ser Arg Ser Ser Leu Asp Ser Arg Leu Ser Ser Trp Asn Arg
145                 150                 155                 160

Arg Ile Lys His Ala Leu Gln Ile Ala Ile Ala Val His Ala Leu His
                165                 170                 175

Thr Ala Glu Thr Gln Val Ile His Arg Asp Ile Lys Ser Cys Asn Val
            180                 185                 190

Leu Ile Asp Gly Asp Gly Asn Ala Arg Leu Ala Asp Phe Gly Leu Ala
        195                 200                 205

Leu Ile Gly Asn Val Asp Asp Glu Arg Leu Lys Tyr Thr Pro Pro Ala
    210                 215                 220

Gly Thr Leu Gly Tyr Leu Asp Pro Ser Tyr Leu Ala Pro Ala Asp Leu
225                 230                 235                 240

Thr Ala Lys Ser Asp Val Phe Ser Phe Gly Ile Leu Leu Leu Glu Ile
                245                 250                 255

Ile Ser Gly Arg Glu Ala Ile Asp Leu Asn Tyr Ser Pro Ser Cys Ile
            260                 265                 270

Val Asp Trp Ala Val Pro Leu Ile Lys Arg Gly Asp Tyr Asp Ala Ile
        275                 280                 285

Cys Asp Leu Lys Ile Lys Asn Arg Pro Tyr Tyr Ala Val Ile Arg Lys
    290                 295                 300

Leu Ala Val Met Ala Ala Arg Cys Val Arg Ser Thr Ala Lys Lys Arg
305                 310                 315                 320

Pro Asp Met Leu Glu Val Val Glu Cys Leu Lys Thr Val Arg Gln Leu
                325                 330                 335

Ser Pro Ala Trp Asn Lys Leu Arg Arg Arg Ser Glu Glu Arg Ser Glu
            340                 345                 350

Asn Val Leu Ala Val Glu Glu Glu Lys Glu Glu Ile His Val Arg Ile
        355                 360                 365

Val Arg Gly Gly Ser Arg Lys Asn Arg Lys Val Ser Asn Val Thr Thr
    370                 375                 380

Ser Val Asp Asp Val Tyr Glu Arg Leu Val Pro Glu Glu Thr Leu Pro
385                 390                 395                 400

Phe Arg Arg Arg Asn Phe Val Leu Arg Ser Arg Ser Val Gly Ala Lys
                405                 410                 415

Val Gly Pro Asp Pro Tyr Asp Gly Phe Gly Asp Glu Thr Val Val Thr
            420                 425                 430

Met Arg Leu Leu Ile Glu Lys Glu Arg Pro Val Thr Thr Ala Ala Met
        435                 440                 445

Arg Leu Ser Lys Ser Arg Ser Val Gly Ile Val Arg Ser His Lys Thr
    450                 455                 460

Ala Ser Arg Lys Arg Tyr
465                 470

<210> SEQ ID NO 23
<211> LENGTH: 1830
<212> TYPE: DNA
<213> ORGANISM: zea mays

<400> SEQUENCE: 23

-continued

```
atgggctacc tctcctgccg cgcggactcg tccgtggcga cgtgccgctc catcacggcc    60
atctcgccgc tcccactctc gcgccgctcg gggtcggggt cggggggcgg ctcgtccagg   120
cccccgctgc cgccggcgca ggcggccatc gagcgcttcg actacgcgga gctggaggcg   180
gccacgtccc acttcgcgga cgcggcgctg ctgggccggg cagccacgg ggccgtctac    240
aaggccgtgc tccccctcgg gccgcgccgt ccgtcaagc ccccctcccc gcgccgcccc    300
gaggtggaca cgagatccg catcctctcc tccgtccggg gcccgcggct cgtcaacctc    360
ctcggcttct ctgaccccgg ccccgccccg cgcctgctcg tcgtcgagta catgcccaac   420
ggcacgctct acgacctgct ccactccaac ccgcgcccgc cgggctggcc gcgccgcctg   480
cgcctcgcgc tccagacggc cagggccctg cgcgcgctcc acgacgccga cccgcccgtc   540
atccaccgcg acgtcaagtc cgccaacgtc ctgctcgacg ccaacctcgg cgcgcgcctc   600
ggcgacttcg gcctcgccct ccgcgtgccc aaggccaccg ccggcgccaa tgccgccgcc   660
gccgccgccc ccacgccgcc gccgccggcc acgtccggct acctcgaccc ggcctacgtc   720
acgcccgaga gcctcagcac caagacagac gtcttcagct tcgggatcct gctgctcgag   780
atcatgagcg gccgcaaggc catcgacgtc cagcactcgc cgccgtccgt cgtcgagtgg   840
gccgtcccgc tcttacggaa aggcaaggtc gcctcgctgt tcgacccgcg tgtggcgccg   900
ccacgagacc cggtcacccg caaggacctt gccgcgctgg ccgccagctg tgtgcgctcc   960
tgcagggagc ggcgcccgtc catggccgac atcgtccagc gtctcgtgct tctcagcaaa  1020
gccgtgtcgg ccaaggtgtg gaacgggctc gccgacgggc ttgccgtggt agggaaccct  1080
tgtgcggttg ttgatgttca agaccatc tccaagcgag gtgctgccag ccgcagggct    1140
gaatcagaga gggagtcgac ttcagcattg gtgtttgacg acgatgaaaa ggaggatgta  1200
gatgcagagg ccttggagga agatcaggtg ccatccaaca agtcaccacc ccgaccactg  1260
aagaacggga tagtgttttc cgaggcaggg gctcggagag ggagaaatct cttggacctg  1320
atggctcgga tcgatggtgt tgccggccaa agattcggca ttaccagagc aagaacagtg  1380
cgtgctaatg gtgagctcat cgaaaaggat gcagtgttgc tcctaaggag gaaccagacg  1440
gtaagagttg ttggatcaga ggcactgccg aagtctggaa ggatttctcg ctatgatgtg  1500
aagatcaaac acaaagcagg ggaagagcaa gaggagacag ggaaagccca agacaaagta  1560
gagaaaatcc aagttaatgc aagcgggatt caagaaagtt ccaaggaaat attaggcaag  1620
acagataaat tgttggatgc actggagcca aaccttgaca agaagagaa ggttcaagaa   1680
aaggaagagc aacacctcga tgaagtggat aatgttcaag agaatgaagg caaagtccaa  1740
tgcccggcag agaaaatcca ggaaggtgga gaagtccaat gccccggca gagaaaatcc    1800
aggaaagtcg aggattctga gacaaagtag                                    1830
```

<210> SEQ ID NO 24
<211> LENGTH: 609
<212> TYPE: PRT
<213> ORGANISM: zea mays

<400> SEQUENCE: 24

```
Met Gly Tyr Leu Ser Cys Arg Ala Asp Ser Val Ala Thr Cys Arg
1               5                  10                  15

Ser Ile Thr Ala Ile Ser Pro Leu Pro Leu Ser Arg Arg Ser Gly Ser
            20                  25                  30

Gly Ser Gly Gly Gly Ser Ser Arg Pro Pro Leu Pro Pro Ala Gln Ala
        35                  40                  45
```

```
Ala Ile Glu Arg Phe Asp Tyr Ala Glu Leu Glu Ala Ala Thr Ser His
 50                  55                  60

Phe Ala Asp Ala Ala Leu Leu Gly Arg Gly Ser His Gly Ala Val Tyr
 65                  70                  75                  80

Lys Ala Val Leu Pro Ser Gly Arg Ala Val Ala Val Lys Arg Pro Ser
                 85                  90                  95

Pro Arg Arg Pro Glu Val Asp Asn Glu Ile Arg Ile Leu Ser Ser Val
                100                 105                 110

Arg Gly Pro Arg Leu Val Asn Leu Leu Gly Phe Ser Asp Pro Gly Pro
            115                 120                 125

Ala Pro Arg Leu Leu Val Glu Tyr Met Pro Asn Gly Thr Leu Tyr
    130                 135                 140

Asp Leu Leu His Ser Asn Pro Arg Pro Gly Trp Pro Arg Arg Leu
145                 150                 155                 160

Arg Leu Ala Leu Gln Thr Ala Arg Ala Leu Arg Ala Leu His Asp Ala
                165                 170                 175

Asp Pro Pro Val Ile His Arg Asp Val Lys Ser Ala Asn Val Leu Leu
            180                 185                 190

Asp Ala Asn Leu Gly Ala Arg Leu Gly Asp Phe Gly Leu Ala Leu Arg
        195                 200                 205

Val Pro Lys Ala Thr Ala Gly Ala Asn Ala Ala Ala Ala Ala Ala Pro
210                 215                 220

Thr Pro Pro Ala Gly Thr Leu Gly Tyr Leu Asp Pro Ala Tyr Val
225                 230                 235                 240

Thr Pro Glu Ser Leu Ser Thr Lys Thr Asp Val Phe Ser Phe Gly Ile
                245                 250                 255

Leu Leu Leu Glu Ile Met Ser Gly Arg Lys Ala Ile Asp Val Gln His
            260                 265                 270

Ser Pro Pro Ser Val Val Glu Trp Ala Val Pro Leu Leu Arg Lys Gly
        275                 280                 285

Lys Val Ala Ser Leu Phe Asp Pro Arg Val Ala Pro Pro Arg Asp Pro
290                 295                 300

Val Thr Arg Lys Asp Leu Ala Ala Leu Ala Ala Ser Cys Val Arg Ser
305                 310                 315                 320

Cys Arg Glu Arg Arg Pro Ser Met Ala Asp Ile Val Gln Arg Leu Val
                325                 330                 335

Leu Leu Ser Lys Ala Val Ser Ala Lys Val Trp Asn Gly Leu Ala Asp
            340                 345                 350

Gly Leu Ala Val Val Gly Asn Pro Cys Ala Val Val Asp Val Gln Lys
        355                 360                 365

Thr Ile Ser Lys Arg Gly Ala Ala Ser Arg Ala Glu Ser Glu Arg
    370                 375                 380

Glu Ser Thr Ser Ala Leu Val Phe Asp Asp Glu Lys Glu Asp Val
385                 390                 395                 400

Asp Ala Glu Ala Leu Glu Glu Asp Gln Val Pro Ser Asn Lys Ser Pro
                405                 410                 415

Pro Arg Pro Leu Lys Asn Gly Ile Val Phe Ser Glu Ala Gly Ala Arg
            420                 425                 430

Glu Arg Arg Asn Leu Leu Asp Leu Met Ala Arg Ile Asp Gly Val Ala
        435                 440                 445

Gly Gln Arg Phe Gly Ile Thr Arg Ala Arg Thr Val Arg Ala Asn Gly
    450                 455                 460
```

| | | | | | | | | | | | |
|---|---|---|---|---|---|---|---|---|---|---|---|
| Glu | Leu | Ile | Glu | Lys | Asp | Ala | Val | Leu | Leu | Arg | Arg | Asn | Gln | Thr |
| 465 | | | | 470 | | | | | 475 | | | | | 480 |

Glu Leu Ile Glu Lys Asp Ala Val Leu Leu Arg Arg Asn Gln Thr
465                 470                 475                 480

Val Arg Val Val Gly Ser Glu Ala Leu Pro Lys Ser Gly Arg Ile Ser
            485                 490                 495

Arg Tyr Asp Val Lys Ile Lys His Lys Ala Gly Glu Glu Gln Glu Glu
        500                 505                 510

Thr Gly Lys Ala Gln Asp Lys Val Glu Lys Ile Gln Val Asn Ala Ser
        515                 520                 525

Gly Ile Gln Glu Ser Ser Lys Glu Ile Leu Gly Lys Thr Asp Lys Leu
    530                 535                 540

Leu Asp Ala Leu Glu Pro Asn Leu Asp Lys Glu Glu Lys Val Gln Glu
545                 550                 555                 560

Lys Glu Glu Gln His Leu Asp Glu Val Asp Asn Val Gln Glu Asn Glu
                565                 570                 575

Gly Lys Val Gln Cys Pro Ala Glu Lys Ile Gln Glu Gly Gly Glu Val
                580                 585                 590

Gln Cys Pro Arg Gln Arg Lys Ser Arg Lys Val Glu Asp Ser Glu Thr
            595                 600                 605

Lys

<210> SEQ ID NO 25
<211> LENGTH: 1287
<212> TYPE: DNA
<213> ORGANISM: glycine max
<220> FEATURE:
<221> NAME/KEY: misc_feature
<222> LOCATION: (747)..(747)
<223> OTHER INFORMATION: n is a, c, g, or t

<400> SEQUENCE: 25

```
atgccctacc tcacttgcaa cgccgagtcc gcaatagcca catgcgaccc tcactccctc      60
aagaagaaga aaaagcccaa agcccagcc caggcccagc ccgtgcgaca cttcgcctac     120
tccgacatcc tcgacgccac caacaacttc tctgccgaca ccttcctagg taaaggcagc     180
cacggcacag tctacaaggc cgccttccac ggcggcgctc tcgtcgccgc cgtcaaaata     240
accaaaccca aacctcaaa cgaaatcgaa attctctccc acctcaaaaa aaaccctcgt     300
cttgttaacc taattggctt ctgcaacgac caaacccaaa ctaacaacat taacaacaac     360
aaactcattg ttgtcgagta catgccaaac ggttcgctcc acgagcttct ccactcgact     420
aaaaaaccgg ttcgaccccc aagctggacc gcgcgagtcc ggtttgcggt tcaggtcgcg     480
aaagcggttc gccttttaca ctcttccgaa ccgccagtta ttcacaggga cataaaatcg     540
tccaatgtgt taatcgacga aaagtggaac gctagactcg gtgacttcgg gctcgcggtg     600
agggacacg tggcggattc tcgcgtgcca ccggcgggga cgttaggata cctcgacccg     660
tgctatcttg cgccgggaga tctaagttcc aagagcgatg tcttcagttt cggagttttg     720
ctgctcgaga tcgcgagtgg gaggcacgcg ctcgacgtga ggcacagtcc gccgtcggtg     780
ctggactggg cggtgccgct ggtccggcgc ggcgagttta aggagatttg tgacccgaga     840
attggagcac cgccggacat ggcggcgttc cggcggatgg cggtgctggc ggcgaggtgc     900
gtgaggagca ccccggagag aaggccgtcg atggtggagt gtttggagtg tctaacggcg     960
gtgagaaaat gttttcgcgc gccggtaatg tggaagagga ttaagaggcg cgtggagata    1020
gcgcgtgggg atttgtttca tgattgggac aggagtgagg aagttgtgag agtagttaag    1080
ttaggaagta gtagtagtag aaggaacggg aaagtatcta gtgtgtcggg tgtagagtat    1140
```

```
gagggtggac acgcgaatcc agcggtgaga tctagatcgg ttggttcggg ttcgggtttg    1200
gttgggtttg ggttcaagaa tagaaaaggg aaagtgaggc taaagagatc gaggtctatg    1260
gggagtccgg tgcctctccg gtggtga                                        1287
```

<210> SEQ ID NO 26
<211> LENGTH: 428
<212> TYPE: PRT
<213> ORGANISM: glycine max

<400> SEQUENCE: 26

```
Met Pro Tyr Leu Thr Cys Asn Ala Glu Ser Ala Ile Ala Thr Cys Asp
1               5                   10                  15

Pro His Ser Leu Lys Lys Lys Lys Pro Lys Ser Pro Ala Gln Ala
            20                  25                  30

Gln Pro Val Arg His Phe Ala Tyr Ser Asp Ile Leu Asp Ala Thr Asn
        35                  40                  45

Asn Phe Ser Ala Asp Thr Phe Leu Gly Lys Gly Ser His Gly Thr Val
    50                  55                  60

Tyr Lys Ala Ala Phe His Gly Gly Ala Leu Val Ala Ala Val Lys Ile
65                  70                  75                  80

Thr Lys Pro Lys Thr Ser Asn Glu Ile Glu Ile Leu Ser His Leu Lys
                85                  90                  95

Lys Asn Pro Arg Leu Val Asn Leu Ile Gly Phe Cys Asn Asp Gln Thr
            100                 105                 110

Gln Thr Asn Asn Ile Asn Asn Asn Lys Leu Ile Val Val Glu Tyr Met
        115                 120                 125

Pro Asn Gly Ser Leu His Glu Leu Leu His Ser Thr Lys Lys Pro Val
    130                 135                 140

Arg Pro Pro Ser Trp Thr Ala Arg Val Arg Phe Ala Val Gln Val Ala
145                 150                 155                 160

Lys Ala Val Arg Leu Leu His Ser Ser Glu Pro Val Ile His Arg
                165                 170                 175

Asp Ile Lys Ser Ser Asn Val Leu Ile Asp Glu Lys Trp Asn Ala Arg
            180                 185                 190

Leu Gly Asp Phe Gly Leu Ala Val Arg Gly His Val Ala Asp Ser Arg
        195                 200                 205

Val Pro Pro Ala Gly Thr Leu Gly Tyr Leu Asp Pro Cys Tyr Leu Ala
    210                 215                 220

Pro Gly Asp Leu Ser Ser Lys Ser Asp Val Phe Ser Phe Gly Val Leu
225                 230                 235                 240

Leu Leu Glu Ile Ala Ser Gly Arg His Ala Leu Asp Val Arg His Ser
                245                 250                 255

Pro Pro Ser Val Leu Asp Trp Ala Val Pro Leu Val Arg Arg Gly Glu
            260                 265                 270

Phe Lys Glu Ile Cys Asp Pro Arg Ile Gly Ala Pro Pro Asp Met Ala
        275                 280                 285

Ala Phe Arg Arg Met Ala Val Leu Ala Ala Arg Cys Val Arg Ser Thr
    290                 295                 300

Pro Glu Arg Arg Pro Ser Met Val Glu Val Leu Glu Cys Leu Thr Ala
305                 310                 315                 320

Val Arg Lys Cys Phe Arg Ala Pro Val Met Trp Lys Arg Ile Lys Arg
                325                 330                 335

Arg Val Glu Ile Ala Arg Gly Asp Leu Phe His Asp Trp Asp Arg Ser
            340                 345                 350
```

Glu Glu Val Val Arg Val Val Lys Leu Gly Ser Ser Ser Arg Arg
        355                 360                 365

Asn Gly Lys Val Ser Ser Val Ser Gly Val Glu Tyr Glu Gly Gly His
    370                 375                 380

Ala Asn Pro Ala Val Arg Ser Arg Ser Val Gly Ser Gly Ser Gly Leu
385                 390                 395                 400

Val Gly Phe Gly Phe Lys Asn Arg Lys Gly Lys Val Arg Leu Lys Arg
                405                 410                 415

Ser Arg Ser Met Gly Ser Pro Val Pro Leu Arg Trp
            420                 425

<210> SEQ ID NO 27
<211> LENGTH: 2040
<212> TYPE: DNA
<213> ORGANISM: oryza sativa

<400> SEQUENCE: 27

| | |
|---|---|
| atgggqtacc tctcctgccg cgcggactcg tcggtggcga cgtgccggtc catcaccgcc | 60 |
| atatcgccgc tgccgctgtc gcggcggtcg ggggtcggcg gcaggcggcg cgcgctgccg | 120 |
| gcggcggcga gggaggggga tggtggggag cgtcgtccg ccgccgccac catcgagcgg | 180 |
| ttcgcgtacg acgaactgga ggcggcgacc tcccacttcg cggacgcggc gctgctcggg | 240 |
| aggggcagcc acgggcggt gtacaaggcg gtgctcgcct ccggccgcgc cgtcgccgtc | 300 |
| aagcgcccct ccccgcgccg ccccgaggtg acaacgaga tccgcatcct ctcctccgtc | 360 |
| cgcggcccgc gcctcgtcaa cctcctcggc ttctccgact ccggcgccgg cgccggcgcc | 420 |
| gaccagcagc agcagcagca ccgcccgcgc ctgctcgtcg tcgagtacat gcccaacggc | 480 |
| acgtcctatg agctgctcca ttccaacccg cgcccgcccg gtggccgcg ccgcgtccgc | 540 |
| ctcgcgctcc agacggcgcg cgcgctccgc gcgctccacg acgccgatcc cccgtcatc | 600 |
| catcgcgacg tcaagtccgc caacgtcctg ctcgacgcca acctcgacgc gcgcctcggc | 660 |
| gacttcggcc tagccctccg cgtgcccaag cggctacccg cgacgccgc cgccaatgcc | 720 |
| gccgccacgc cggcgccggc gggcacgctc gggtacctcg acccggccta cgtcacgccg | 780 |
| gagagcctca gcaccaagac cgacgtcttc agcttcggga tcctgctgct cgagatcatg | 840 |
| agcgccgca aggccatcga cgtccagcac tcgccgccgt cggtggtgga gtgggcggtg | 900 |
| cccctgctgc ggaaggggaa ggtggcctcg ctgttcgacc cacgggtggc gccgccgcgt | 960 |
| gacccggtca cccggagaga cctagccgct ctggcggcga gctgcgtgcg gtcgtgcagg | 1020 |
| gagcggcggc cgtcgatggc cgacatagtt gatcggcttg tggttctcag caaggccgtg | 1080 |
| tcgggcaaaa tgtggaacgg actcgccgtg gttgggaacc cctgcgctgt cgtggatgtc | 1140 |
| cagaagacca tcgcgaagcg agctgctgct gctgctgcag gcgatagagc cgcgtcgcag | 1200 |
| cgggagctga cttcggcatt ggcatttgat gatgatgaga agaaagagga ggaggatgcg | 1260 |
| ccgaatgcag gtgcgttaga ggaggatgag gtgccattgg tgggtgcgaa gaaagcaccc | 1320 |
| cggccattga agaatgggaa gatgttctct gagccagggg caagggagag gaaaatctc | 1380 |
| ttggagctca tggctcggat tgatggtgtc gccggccaaa gatttggcat aactcgggca | 1440 |
| agaacagtgc gtgccgctag tgaatctatc gaaaagatg cggcggtgtt gctcctgagg | 1500 |
| agaaatcaaa ctgtgaaagt acttggatcg gaggccctt ctaaagctga tatcttttca | 1560 |
| agtttggatg caaaaatcaa gcatgaattg gggaaagagc agcaagagga ggcaggaaaa | 1620 |
| atcaagcatg aattggtgaa agagcagcaa gagaaggcag gaaatatcaa gcaggaattg | 1680 |

-continued

```
gtgaaagagc agcaagagaa ggcaggaaat atcaagcagg aatcagggga agagcaagag    1740
aaggcaggga aaaccaagca tgatgcaggg aaagggcatg ttgagaaggc agtgggaatc    1800
aatcttgaag cagggaagga gcaggagaaa gtagagaaaa accaagagaa agaaatgaaa    1860
atccaagaaa aacttgggga aatctttgat aaagcaatga aatctgaaga aaagacaggg    1920
caaaatcctg gcatagaaaa gaaaatccaa gacacggcag agaagaaaca agagcatgat    1980
gctagggtag tccaagacaa agtggagaag atccaagacg aagccaagaa aatccaatga    2040
```

<210> SEQ ID NO 28
<211> LENGTH: 679
<212> TYPE: PRT
<213> ORGANISM: oryza sativa

<400> SEQUENCE: 28

```
Met Gly Tyr Leu Ser Cys Arg Ala Asp Ser Val Ala Thr Cys Arg
1               5                   10                  15

Ser Ile Thr Ala Ile Ser Pro Leu Pro Leu Ser Arg Arg Ser Gly Val
                20                  25                  30

Gly Gly Arg Arg Arg Ala Leu Pro Ala Ala Ala Arg Glu Gly Asp Gly
            35                  40                  45

Gly Glu Ala Ser Ser Ala Ala Ala Thr Ile Glu Arg Phe Ala Tyr Asp
        50                  55                  60

Glu Leu Glu Ala Ala Thr Ser His Phe Ala Asp Ala Ala Leu Leu Gly
65                  70                  75                  80

Arg Gly Ser His Gly Ala Val Tyr Lys Ala Val Leu Ala Ser Gly Arg
                85                  90                  95

Ala Val Ala Val Lys Arg Pro Ser Pro Arg Pro Glu Val Asp Asn
            100                 105                 110

Glu Ile Arg Ile Leu Ser Ser Val Arg Gly Pro Arg Leu Val Asn Leu
        115                 120                 125

Leu Gly Phe Ser Asp Ser Gly Ala Gly Ala Gly Ala Asp Gln Gln Gln
    130                 135                 140

Gln Gln His Arg Pro Arg Leu Leu Val Val Glu Tyr Met Pro Asn Gly
145                 150                 155                 160

Thr Leu Tyr Glu Leu Leu His Ser Asn Pro Arg Pro Pro Gly Trp Pro
                165                 170                 175

Arg Arg Val Arg Leu Ala Leu Gln Thr Ala Arg Ala Leu Arg Ala Leu
            180                 185                 190

His Asp Ala Asp Pro Pro Val Ile His Arg Asp Val Lys Ser Ala Asn
        195                 200                 205

Val Leu Leu Asp Ala Asn Leu Asp Ala Arg Leu Gly Asp Phe Gly Leu
    210                 215                 220

Ala Leu Arg Val Pro Lys Arg Leu Pro Gly Asp Ala Ala Asn Ala
225                 230                 235                 240

Ala Ala Thr Pro Ala Pro Ala Gly Thr Leu Gly Tyr Leu Asp Pro Ala
                245                 250                 255

Tyr Val Thr Pro Glu Ser Leu Ser Thr Lys Thr Asp Val Phe Ser Phe
            260                 265                 270

Gly Ile Leu Leu Leu Glu Ile Met Ser Gly Arg Lys Ala Ile Asp Val
        275                 280                 285

Gln His Ser Pro Pro Ser Val Val Glu Trp Ala Val Pro Leu Leu Arg
    290                 295                 300

Lys Gly Lys Val Ala Ser Leu Phe Asp Pro Arg Val Ala Pro Pro Arg
```

```
                305                 310                 315                 320
Asp Pro Val Thr Arg Arg Asp Leu Ala Ala Leu Ala Ala Ser Cys Val
                    325                 330                 335

Arg Ser Cys Arg Glu Arg Pro Ser Met Ala Asp Ile Val Asp Arg
                340                 345                 350

Leu Val Val Leu Ser Lys Ala Val Ser Gly Lys Met Trp Asn Gly Leu
                    355                 360                 365

Ala Val Val Gly Asn Pro Cys Ala Val Val Asp Val Gln Lys Thr Ile
370                 375                 380

Ala Lys Arg Ala Ala Ala Ala Gly Asp Arg Ala Ala Ser Gln
385                 390                 395                 400

Arg Glu Leu Thr Ser Ala Leu Ala Phe Asp Asp Glu Lys Glu
                    405                 410                 415

Glu Glu Asp Ala Pro Asn Ala Gly Ala Leu Glu Glu Asp Glu Val Pro
                    420                 425                 430

Leu Val Gly Ala Lys Lys Ala Pro Arg Pro Leu Lys Asn Gly Lys Met
                    435                 440                 445

Phe Ser Glu Pro Gly Ala Arg Glu Arg Arg Asn Leu Leu Glu Leu Met
450                 455                 460

Ala Arg Ile Asp Gly Val Ala Gly Gln Arg Phe Gly Ile Thr Arg Ala
465                 470                 475                 480

Arg Thr Val Arg Ala Ala Ser Glu Ser Ile Glu Lys Asp Ala Ala Val
                    485                 490                 495

Leu Leu Leu Arg Arg Asn Gln Thr Val Lys Val Leu Gly Ser Glu Ala
                    500                 505                 510

Leu Ser Lys Ala Asp Ile Phe Ser Ser Leu Asp Ala Lys Ile Lys His
                515                 520                 525

Glu Leu Gly Lys Glu Gln Gln Glu Glu Ala Gly Lys Ile Lys His Glu
                530                 535                 540

Leu Val Lys Glu Gln Gln Glu Lys Ala Gly Asn Ile Lys Gln Glu Leu
545                 550                 555                 560

Val Lys Glu Gln Gln Glu Lys Ala Gly Asn Ile Lys Gln Glu Ser Gly
                    565                 570                 575

Glu Glu Gln Glu Lys Ala Gly Lys Thr Lys His Asp Ala Gly Lys Gly
                    580                 585                 590

His Val Glu Lys Ala Val Gly Ile Asn Leu Glu Ala Gly Lys Glu Gln
                595                 600                 605

Glu Lys Val Glu Lys Asn Gln Glu Lys Glu Met Lys Ile Gln Glu Lys
                    610                 615                 620

Leu Gly Glu Ile Phe Asp Lys Ala Met Lys Ser Glu Lys Thr Gly
625                 630                 635                 640

Gln Asn Pro Gly Ile Glu Lys Lys Ile Gln Asp Thr Ala Glu Lys Lys
                    645                 650                 655

Gln Glu His Asp Ala Arg Val Val Gln Asp Lys Val Leu Lys Ile Gln
                    660                 665                 670

Asp Glu Ala Lys Lys Ile Gln
                675

<210> SEQ ID NO 29
<211> LENGTH: 1235
<212> TYPE: DNA
<213> ORGANISM: gossypium hirsutum

<400> SEQUENCE: 29
```

-continued

| | |
|---|---|
| atgggttacc tctcttgcaa tgcagagtcc accattaaag tttgtgatcc tggcaactgg | 60 |
| gattattata gaaaaaaacc caagaaaaac aagcccagaa tccggcagtt tcgttacacc | 120 |
| gatcttctta ccgccaccaa tggcttctct tccgatagct tcctcggtaa aggtagtcac | 180 |
| ggttccgtct acaaagccgt acttgacgat ggcaagttaa tcaccgccgt taagaaaacg | 240 |
| tcaaagaact gtaacagtcc tgccgacaac gagatcgaga ttctttcccg agttgatcat | 300 |
| cctcgactcg ttaatctcat cggttactgc tccgattcgc tttgtaagaa taaattaatc | 360 |
| gtcgtggaat atatgcccaa cggttcattg tacgatcttt acattcttc ttcttgtaaa | 420 |
| ccgccgggtt ggtccagccg ggttcgattc gctttacagg tagcaaaagc ggttcaagct | 480 |
| ttacattcgg gtagcccgcc ggtgatccac agggatataa aatcgtccaa tgttttaatt | 540 |
| gatcaaaggt ggaacgctcg attgggtgat ttcgggcttg cattgatagg acacgtggag | 600 |
| gatgtacgga ttaagtgcac cccaccggcg gggacgttag gatatctcga cccgagttat | 660 |
| ttagccccga gtgacgtcag cacgaaaagt gacgtgttca gttacggcat tttgttattg | 720 |
| gagattatta gcgggaggca tgctattgat ttgaagtata gtccgccgtc agttgttgac | 780 |
| tgggcggttc cgttgataaa gaaagggaat attgttgctg tttatgatcc aaggatttta | 840 |
| cctcctaagg atcctatagt taggaagcaa ttggctgtca ttgcagctaa atgtgtgagg | 900 |
| tcttgtaggg agcgtcgccc tgcaatgaaa gaggtggtcg gttggttaac tgggttaagc | 960 |
| aaattggttc ctttacattc atggaatggt ttcagcaatc catgtatgat ggtggaaaca | 1020 |
| gtggggcgtc cggtcgattt tagaaatgcc caggagaact tggatgcagt gcatggtacg | 1080 |
| ttggctgcca aggactcgcg cagagcctat tctgatttag gctttaggag taacttgatg | 1140 |
| gaacttatgg gcatcaccag cattgatggg gaggccaaag cttcttctag ccatagattt | 1200 |
| ggtaacaaaa gctacggtaa cctttgtctc gtcct | 1235 |

<210> SEQ ID NO 30
<211> LENGTH: 411
<212> TYPE: PRT
<213> ORGANISM: gossypium hirsutum

<400> SEQUENCE: 30

Met Gly Tyr Leu Ser Cys Asn Ala Glu Ser Thr Ile Lys Val Cys Asp
1               5                   10                  15

Pro Gly Asn Trp Asp Tyr Tyr Arg Lys Lys Pro Lys Lys Asn Lys Pro
            20                  25                  30

Arg Ile Arg Gln Phe Arg Tyr Thr Asp Leu Leu Thr Ala Thr Asn Gly
        35                  40                  45

Phe Ser Ser Asp Ser Phe Leu Gly Lys Gly Ser His Gly Ser Val Tyr
    50                  55                  60

Lys Ala Val Leu Asp Asp Gly Lys Leu Ile Thr Ala Val Lys Lys Thr
65                  70                  75                  80

Ser Lys Asn Cys Asn Ser Pro Ala Asp Asn Glu Ile Glu Ile Leu Ser
                85                  90                  95

Arg Val Asp His Pro Arg Leu Val Asn Leu Ile Gly Tyr Cys Ser Asp
            100                 105                 110

Ser Leu Cys Lys Asn Lys Leu Ile Val Val Glu Tyr Met Pro Asn Gly
        115                 120                 125

Ser Leu Tyr Asp Leu Leu His Ser Ser Cys Lys Pro Pro Gly Trp
    130                 135                 140

Ser Ser Arg Val Arg Phe Ala Leu Gln Val Ala Lys Ala Val Gln Ala
145                 150                 155                 160

```
Leu His Ser Gly Ser Pro Val Ile His Arg Asp Ile Lys Ser Ser
            165                 170                 175

Asn Val Leu Ile Asp Gln Arg Trp Asn Ala Arg Leu Gly Asp Phe Gly
            180                 185                 190

Leu Ala Leu Ile Gly His Val Glu Asp Val Arg Ile Lys Cys Thr Pro
            195                 200                 205

Pro Ala Gly Thr Leu Gly Tyr Leu Asp Pro Ser Tyr Leu Ala Pro Ser
    210                 215                 220

Asp Val Ser Thr Lys Ser Asp Val Phe Ser Tyr Gly Ile Leu Leu Leu
225                 230                 235                 240

Glu Ile Ile Ser Gly Arg His Ala Ile Asp Leu Lys Tyr Ser Pro Pro
                245                 250                 255

Ser Val Val Asp Trp Ala Val Pro Leu Ile Lys Lys Gly Asn Ile Val
            260                 265                 270

Ala Val Tyr Asp Pro Arg Ile Leu Pro Pro Lys Asp Pro Ile Val Arg
            275                 280                 285

Lys Gln Leu Ala Val Ile Ala Ala Lys Cys Val Arg Ser Cys Arg Glu
    290                 295                 300

Arg Arg Pro Ala Met Lys Glu Val Val Gly Trp Leu Thr Gly Leu Ser
305                 310                 315                 320

Lys Leu Val Pro Leu His Ser Trp Asn Gly Phe Ser Asn Pro Cys Met
                325                 330                 335

Met Val Glu Thr Val Gly Arg Pro Val Asp Phe Arg Asn Ala Gln Glu
            340                 345                 350

Asn Leu Asp Ala Val His Gly Thr Leu Ala Ala Lys Asp Ser Arg Arg
            355                 360                 365

Ala Tyr Ser Asp Leu Gly Phe Arg Ser Asn Leu Met Glu Leu Met Gly
    370                 375                 380

Ile Thr Ser Ile Asp Gly Glu Ala Lys Ala Ser Ser Ser His Arg Phe
385                 390                 395                 400

Gly Asn Lys Ser Tyr Gly Asn Leu Cys Leu Val
                405                 410

<210> SEQ ID NO 31
<211> LENGTH: 2025
<212> TYPE: DNA
<213> ORGANISM: Arabidopsis thaliana

<400> SEQUENCE: 31
atgggcatgg aagctttgag atttcttcat gttatcttct tctttgtgct aattcttcac      60
tgtcattgtg aacatctctc tctggttct tctgatgtga agcttctttt aggaaaaatc     120
aagtcttcac tacaaggaaa cagtgagagc ttactgttgt cttcttggaa ctcctctgtt     180
cctgtttgtc aatggagagg tgtaaaatgg gtattttcaa atgggtctcc tcttcaatgt     240
agtgacctct cttcaccaca atggactaat acctctctgt tcaacgactc ttctcttcac     300
cttctctctc ttcagcttcc ttctgctaat ctcactggtt cactccctag agagattggt     360
gagttctcta tgcttcaaag tgtgttcctc aacatcaatt cattaagtgg gtcaatccct     420
cttgagcttg ttacacttc ttctctctct gatgttgatt tgagtggtaa tgccttagct     480
ggggttttgc ctccatcgat ttggaaccte tgtgataagc ttgtctcttt caagattcat     540
ggtaataact tgtctggggt tttgcctgag cctgctttgc caaattcgac ttgtggtaat     600
ctccaagttc ttgatttggg tggtaataag ttctcaggtg agtttcctga gtttataact     660
```

```
aggtttaaag gtgtgaagtc acttgatctt tcaagtaatg tctttgaagg tcttgttcct    720
gagggtttag gtgtattaga gctagaaagt ctcaatcttt ctcataataa cttcagtggg    780
atgttgccag attttggtga gtcaaagttt ggagcagaat ctttcgaagg aacagtcct     840
agcctttgtg gtttgccttt gaagccttgt ctaggctcct ctaggttaag tccaggtgct    900
gttgctggtc tggtgattgg tttaatgtct ggagctgttg ttgtggcctc gttgttaata    960
gggtatttgc agaacaagaa agaaagagt agtatagaga gtgaagatga tttggaagaa    1020
ggtgatgaag aagatgaaat cggtgagaaa gaaggcggtg aaggaaagtt agttgtgttt    1080
caaggtggtg agaatctgac gttggatgat gttttgaatg ctactgggca agttatggag    1140
aagactagct atggtactgt ctataaagct aagcttagtg atggagggaa tattgcattg    1200
aggctattga gagaaggtac ttgcaaggat agaagttctt gtctgcctgt tataaggcag    1260
ttaggacgca ttcggcatga gaatttggtt cccttgagag cttttctatca agggaagaga    1320
ggagaaaagc ttctcatcta tgactatctt cccaacataa gcttacatga tttgttgcat    1380
gaaagtaaac ctcgaaagcc agctttgaat tgggctagga cacaagat tgcacttgga    1440
atagcgaggg gacttgctta tcttcatact ggacaagaag ttcctatcat ccatggaaat    1500
attagatcaa agaacgtgct tgtggacgac ttttcttgg caaggctaac tgagtttggg    1560
cttgacaaga taatggtaca ggcagtagca gatgagattg tctcgcaggc gaaatccgac    1620
gggtacaaag cacctgaact ccacaagatg aagaaatgca atccaaggag tgatgtttac    1680
gcctttggga tccttctctt ggagatattg atgggtaaga aaccaggaaa gagtggaagg    1740
aacggtaatg agtttgtgga cttgccttct ttggttaaag ctgcggtgtt ggaagagacg    1800
acaatggagg ttttcgactt ggaggcaatg aaagggatta ggagcccaat ggaagaaggt    1860
ttggttcatg cattgaagct agcgatggga tgttgtgctc ctgttacaac agttagaccc    1920
agcatggaag aggttgtgaa gcagttggaa gagaacagac cgaggaatag atccgcattg    1980
tacagcccaa ccgaaaccag gagcgacgcc gaaactccat tttga              2025
```

<210> SEQ ID NO 32
<211> LENGTH: 674
<212> TYPE: PRT
<213> ORGANISM: Arabidopsis thaliana

<400> SEQUENCE: 32

```
Met Gly Met Glu Ala Leu Arg Phe Leu His Val Ile Phe Phe Val
1               5                   10                  15

Leu Ile Leu His Cys His Cys Gly Thr Ser Leu Ser Gly Ser Ser Asp
            20                  25                  30

Val Lys Leu Leu Leu Gly Lys Ile Lys Ser Ser Leu Gln Gly Asn Ser
        35                  40                  45

Glu Ser Leu Leu Leu Ser Ser Trp Asn Ser Ser Val Pro Val Cys Gln
    50                  55                  60

Trp Arg Gly Val Lys Trp Val Phe Ser Asn Gly Ser Pro Leu Gln Cys
65                  70                  75                  80

Ser Asp Leu Ser Ser Pro Gln Trp Thr Asn Thr Ser Leu Phe Asn Asp
                85                  90                  95

Ser Ser Leu His Leu Leu Ser Leu Gln Leu Pro Ser Ala Asn Leu Thr
            100                 105                 110

Gly Ser Leu Pro Arg Glu Ile Gly Glu Phe Ser Met Leu Gln Ser Val
        115                 120                 125

Phe Leu Asn Ile Asn Ser Leu Ser Gly Ser Ile Pro Leu Glu Leu Gly
```

```
            130                 135                 140
Tyr Thr Ser Ser Leu Ser Asp Val Asp Leu Ser Gly Asn Ala Leu Ala
145                 150                 155                 160

Gly Val Leu Pro Pro Ser Ile Trp Asn Leu Cys Asp Lys Leu Val Ser
                165                 170                 175

Phe Lys Ile His Gly Asn Asn Leu Ser Gly Val Leu Pro Glu Pro Ala
                180                 185                 190

Leu Pro Asn Ser Thr Cys Gly Asn Leu Gln Val Leu Asp Leu Gly Gly
            195                 200                 205

Asn Lys Phe Ser Gly Glu Phe Pro Glu Phe Ile Thr Arg Phe Lys Gly
        210                 215                 220

Val Lys Ser Leu Asp Leu Ser Ser Asn Val Phe Glu Gly Leu Val Pro
225                 230                 235                 240

Glu Gly Leu Gly Val Leu Glu Leu Glu Ser Leu Asn Leu Ser His Asn
                245                 250                 255

Asn Phe Ser Gly Met Leu Pro Asp Phe Gly Glu Ser Lys Phe Gly Ala
                260                 265                 270

Glu Ser Phe Glu Gly Asn Ser Pro Ser Leu Cys Gly Leu Pro Leu Lys
            275                 280                 285

Pro Cys Leu Gly Ser Ser Arg Leu Ser Pro Gly Ala Val Ala Gly Leu
    290                 295                 300

Val Ile Gly Leu Met Ser Gly Ala Val Val Ala Ser Leu Leu Ile
305                 310                 315                 320

Gly Tyr Leu Gln Asn Lys Lys Arg Lys Ser Ser Ile Glu Ser Glu Asp
                325                 330                 335

Asp Leu Glu Glu Gly Asp Glu Asp Glu Ile Gly Glu Lys Glu Gly
            340                 345                 350

Gly Glu Gly Lys Leu Val Val Phe Gln Gly Gly Glu Asn Leu Thr Leu
        355                 360                 365

Asp Asp Val Leu Asn Ala Thr Gly Gln Val Met Glu Lys Thr Ser Tyr
    370                 375                 380

Gly Thr Val Tyr Lys Ala Lys Leu Ser Asp Gly Gly Asn Ile Ala Leu
385                 390                 395                 400

Arg Leu Leu Arg Glu Gly Thr Cys Lys Asp Arg Ser Cys Leu Pro
                405                 410                 415

Val Ile Arg Gln Leu Gly Arg Ile Arg His Glu Asn Leu Val Pro Leu
            420                 425                 430

Arg Ala Phe Tyr Gln Gly Lys Arg Gly Glu Lys Leu Leu Ile Tyr Asp
        435                 440                 445

Tyr Leu Pro Asn Ile Ser Leu His Asp Leu Leu His Glu Ser Lys Pro
    450                 455                 460

Arg Lys Pro Ala Leu Asn Trp Ala Arg His Lys Ile Ala Leu Gly
465                 470                 475                 480

Ile Ala Arg Gly Leu Ala Tyr Leu His Thr Gly Gln Glu Val Pro Ile
                485                 490                 495

Ile His Gly Asn Ile Arg Ser Lys Asn Val Leu Val Asp Asp Phe Phe
            500                 505                 510

Phe Ala Arg Leu Thr Glu Phe Gly Leu Asp Lys Ile Met Val Gln Ala
        515                 520                 525

Val Ala Asp Glu Ile Val Ser Gln Ala Lys Ser Asp Gly Tyr Lys Ala
    530                 535                 540

Pro Glu Leu His Lys Met Lys Lys Cys Asn Pro Arg Ser Asp Val Tyr
545                 550                 555                 560
```

Ala Phe Gly Ile Leu Leu Leu Glu Ile Leu Met Gly Lys Lys Pro Gly
            565                 570                 575

Lys Ser Gly Arg Asn Gly Asn Glu Phe Val Asp Leu Pro Ser Leu Val
        580                 585                 590

Lys Ala Ala Val Leu Glu Glu Thr Thr Met Glu Val Phe Asp Leu Glu
    595                 600                 605

Ala Met Lys Gly Ile Arg Ser Pro Met Glu Glu Gly Leu Val His Ala
610                 615                 620

Leu Lys Leu Ala Met Gly Cys Cys Ala Pro Val Thr Thr Val Arg Pro
625                 630                 635                 640

Ser Met Glu Glu Val Val Lys Gln Leu Glu Glu Asn Arg Pro Arg Asn
            645                 650                 655

Arg Ser Ala Leu Tyr Ser Pro Thr Glu Thr Arg Ser Asp Ala Glu Thr
            660                 665                 670

Pro Phe

<210> SEQ ID NO 33
<211> LENGTH: 2037
<212> TYPE: DNA
<213> ORGANISM: zea mays

<400> SEQUENCE: 33

| | | | | | |
|---|---|---|---|---|---|
| atgcatcctt | gcatgctctt | cctcctctgc | ctggccgcgc | tgccgctggc | ctcgcattcc | 60 |
| tcctccaacc | ccgacgtcgc | gctgctcctc | gccaaggtga | agccggcgct | gcagggcgag | 120 |
| cgcgccaacg | cgcagctcgc | cacctggaac | gcctccacgc | cgctctgcct | ctggcgcggc | 180 |
| ctccgctggg | cgacgcccga | cggccggccc | ctccgctgcg | acgccgccgc | cacgcgcgcc | 240 |
| aacctgtcgc | tcgcctccga | ccccgccctc | ctcctcctct | ccgtccgcct | cccgcgtcc | 300 |
| gccctcgccg | gccgcctccc | gccggacctc | ggcgccttct | ccgcgctcga | ctccgtctac | 360 |
| ctcgccgcca | actcgctctc | gggccccgtc | ccgctcgagc | tcggcaacgc | gcccgcgctc | 420 |
| tccgcgctcg | acctcgccgg | caaccgcctc | tcggggggacc | tgcccgcctc | catctggaac | 480 |
| ctctgcgacc | gcgccaccga | gctccgcctc | acggcaacg | cgctcaccgg | ggccgtgccc | 540 |
| gagccggccg | gccccaacac | cacctgcgac | cgcctccgcg | tcctcgacct | cggcgccaac | 600 |
| cgcttctccg | gcgccttccc | cgccttcgtc | accgcgttcc | gtggcctcca | gcgcctcgac | 660 |
| ctgggcgcca | accgctggga | gggccccatc | ccggaggccc | tcgctgggat | ggcggcgacc | 720 |
| cagcagctcc | aggcgctcaa | cgtctcctac | aacaacttct | ccggccagct | gccccgtcc | 780 |
| ttcgcggcct | cccgcttcac | ggcggactcg | ttcgtaggca | acgaaccagc | gctgtgcggc | 840 |
| ccgccgctgc | gccagtgcgt | gacagcctcg | ggcctcagct | cccgcggcgt | cgccgggatg | 900 |
| gtcatcggga | tcatggccgg | cgccgtcgtg | ctcgcgtccg | tgtccatcgg | ctgggcgcag | 960 |
| gggaggtgga | ggcggagcgg | caggatcccg | gagcaggacg | agatgctgga | gtcggccgac | 1020 |
| gacgcccagg | acgcgtcgtc | agagggcagg | ctcgtggtct | tcgagggcgg | cgagcacctc | 1080 |
| acgctggagg | aggtgctcaa | cgcgaccggc | caggtggtgg | acaaggccag | ctactgcacg | 1140 |
| gtgtacaagg | cgaagctggc | gagcggcggc | agcagcatcg | agctgcgcct | gctgcgggaa | 1200 |
| ggcagctgca | aggacgccgc | gtcgtgcgcg | cccgttgtgc | ggcgcatcgg | ccgcgcgcgc | 1260 |
| cacgagaacc | tggtcccgct | tagggccttc | taccagggga | ggcgcggcga | gaagctgctg | 1320 |
| gtgtacgact | acttccgcg | cagccggacg | ctgcaggagc | tgctgcacgg | tggcagcgag | 1380 |
| cccgcggcgg | ggcggccggc | gctcaccctgg | gggcggcggc | acaagatcgc | gctgggcgcg | 1440 |

-continued

```
gcgcgcgcgc tggcgtatct gcacgcgggc cagggcgagg cgcacgggaa cgtgcgctcg    1500
tccatcgtgg tggtggacga cctcttcgtg ccgcgcctgg cagagtacgc ggtggaccgg    1560
ctgctggtgc cggcggcggc ggaggcggtg ctggcggcgg ccaaggcgga cgggtacaag    1620
gcgccggagc tgcactccat gaagaagtgc agcgcgcgca cggacgtgta cgcgttcggg    1680
atcctgctgc tggagctgct catggggagg aagccgtcgg cctctgcagg tggagctgca    1740
agggcgatgg acctgccgtc ggtggtgaag gtggcggtgc tggaggagac ggcgctggag    1800
gaggtgctgg acgcggaggt ggtcaaggga ctgcgggtga gtccggcgga ggagggctg     1860 gtgcaggcgc tgaagctggc gatgggctgc tgcgcgccgg tgccagcggc gaggccgagc    1920
atggcggagg tggtgcggca gctggaggag agccggccca agaacgtcca cccgcggtct    1980
gcgctgtaca gccctacgga gagcaggagc gacgccggca cgccgaccac cgcctag      2037
```

<210> SEQ ID NO 34
<211> LENGTH: 678
<212> TYPE: PRT
<213> ORGANISM: zea mays

<400> SEQUENCE: 34

```
Met His Pro Cys Met Leu Phe Leu Leu Cys Leu Ala Ala Leu Pro Leu
1               5                   10                  15

Ala Ser His Ser Ser Asn Pro Asp Val Ala Leu Leu Ala Lys
            20                  25                  30

Val Lys Pro Ala Leu Gln Gly Glu Arg Ala Asn Ala Gln Leu Ala Thr
        35                  40                  45

Trp Asn Ala Ser Thr Pro Leu Cys Leu Trp Arg Gly Leu Arg Trp Ala
    50                  55                  60

Thr Pro Asp Gly Arg Pro Leu Arg Cys Asp Ala Ala Thr Arg Ala
65                  70                  75                  80

Asn Leu Ser Leu Ala Ser Asp Pro Ala Leu Leu Leu Ser Val Arg
                85                  90                  95

Leu Pro Ala Ser Ala Leu Ala Gly Arg Leu Pro Pro Asp Leu Gly Ala
            100                 105                 110

Phe Ser Ala Leu Asp Ser Val Tyr Leu Ala Ala Asn Ser Leu Ser Gly
        115                 120                 125

Pro Val Pro Leu Glu Leu Gly Asn Ala Pro Ala Leu Ser Ala Leu Asp
    130                 135                 140

Leu Ala Gly Asn Arg Leu Ser Gly Asp Leu Pro Ala Ser Ile Trp Asn
145                 150                 155                 160

Leu Cys Asp Arg Ala Thr Glu Leu Arg Leu His Gly Asn Ala Leu Thr
                165                 170                 175

Gly Ala Val Pro Glu Pro Ala Gly Pro Asn Thr Thr Cys Asp Arg Leu
            180                 185                 190

Arg Val Leu Asp Leu Gly Ala Asn Arg Phe Ser Gly Ala Phe Pro Ala
        195                 200                 205

Phe Val Thr Ala Phe Arg Gly Leu Gln Arg Leu Asp Leu Gly Ala Asn
    210                 215                 220

Arg Leu Glu Gly Pro Ile Pro Glu Ala Leu Ala Gly Met Ala Ala Thr
225                 230                 235                 240

Gln Gln Leu Gln Ala Leu Asn Val Ser Tyr Asn Asn Phe Ser Gly Gln
                245                 250                 255

Leu Pro Pro Ser Phe Ala Ala Ser Arg Phe Thr Ala Asp Ser Phe Val
            260                 265                 270
```

```
Gly Asn Glu Pro Ala Leu Cys Gly Pro Pro Leu Arg Gln Cys Val Thr
            275                 280                 285

Ala Ser Gly Leu Ser Ser Arg Gly Val Ala Gly Met Val Ile Gly Ile
290                 295                 300

Met Ala Gly Ala Val Val Leu Ala Ser Val Ser Ile Gly Trp Ala Gln
305                 310                 315                 320

Gly Arg Trp Arg Arg Ser Gly Arg Ile Pro Glu Gln Asp Glu Met Leu
            325                 330                 335

Glu Ser Ala Asp Asp Ala Gln Asp Ala Ser Ser Glu Gly Arg Leu Val
            340                 345                 350

Val Phe Glu Gly Gly Glu His Leu Thr Leu Glu Val Leu Asn Ala
            355                 360                 365

Thr Gly Gln Val Val Asp Lys Ala Ser Tyr Cys Thr Val Tyr Lys Ala
        370                 375                 380

Lys Leu Ala Ser Gly Gly Ser Ser Ile Glu Leu Arg Leu Leu Arg Glu
385                 390                 395                 400

Gly Ser Cys Lys Asp Ala Ala Ser Cys Ala Pro Val Val Arg Arg Ile
                405                 410                 415

Gly Arg Ala Arg His Glu Asn Leu Val Pro Leu Arg Ala Phe Tyr Gln
            420                 425                 430

Gly Arg Arg Gly Glu Lys Leu Leu Val Tyr Asp Tyr Phe Pro Arg Ser
        435                 440                 445

Arg Thr Leu Gln Glu Leu Leu His Gly Gly Ser Glu Pro Ala Ala Gly
    450                 455                 460

Arg Pro Ala Leu Thr Trp Gly Arg Arg His Lys Ile Ala Leu Gly Ala
465                 470                 475                 480

Ala Arg Ala Leu Ala Tyr Leu His Ala Gly Gln Gly Glu Ala His Gly
                485                 490                 495

Asn Val Arg Ser Ser Ile Val Val Asp Asp Leu Phe Val Pro Arg
            500                 505                 510

Leu Ala Glu Tyr Ala Val Asp Arg Leu Leu Val Pro Ala Ala Ala Glu
        515                 520                 525

Ala Val Leu Ala Ala Ala Lys Ala Asp Gly Tyr Lys Ala Pro Glu Leu
    530                 535                 540

His Ser Met Lys Lys Cys Ser Ala Arg Thr Asp Val Tyr Ala Phe Gly
545                 550                 555                 560

Ile Leu Leu Leu Glu Leu Leu Met Gly Arg Lys Pro Ser Ala Ser Ala
                565                 570                 575

Gly Gly Ala Ala Arg Ala Met Asp Leu Pro Ser Val Val Lys Val Ala
            580                 585                 590

Val Leu Glu Glu Thr Ala Leu Glu Glu Val Leu Asp Ala Glu Val Val
        595                 600                 605

Lys Gly Leu Arg Val Ser Pro Ala Glu Glu Gly Leu Val Gln Ala Leu
    610                 615                 620

Lys Leu Ala Met Gly Cys Cys Ala Pro Val Pro Ala Ala Arg Pro Ser
625                 630                 635                 640

Met Ala Glu Val Val Arg Gln Leu Glu Glu Ser Arg Pro Lys Asn Val
                645                 650                 655

His Pro Arg Ser Ala Leu Tyr Ser Pro Thr Glu Ser Arg Ser Asp Ala
            660                 665                 670

Gly Thr Pro Thr Thr Ala
        675
```

<210> SEQ ID NO 35
<211> LENGTH: 2100
<212> TYPE: DNA
<213> ORGANISM: glycine max

<400> SEQUENCE: 35

| | | | | | |
|---|---|---|---|---|---|
| atggcgtttc | tgaacccttt | ctctctccac | attcccatgt | ccttgttgtt | cttcttcctc | 60 |
| ttcttttttt | gcttctgcaa | agccagtagt | actaccacct | ccaccacaaa | gtcactgtcc | 120 |
| cccccttctt | caccctccac | tacttcctcc | tctgacgttg | agcttctctt | gggaaagatc | 180 |
| aaagcttcac | tgcaaggtag | taactctgac | aaccttgttt | tgtcttcatg | gaactcctcc | 240 |
| accccacttt | gtcagtggaa | aggcctcata | tgggtcttct | ccaatggcac | tcctctctca | 300 |
| tgcactgact | tgtcctctcc | tcaatggacc | aatctcacac | tcctcaaaga | cccttctctt | 360 |
| cacttgtttt | ccctccggct | cccttctgca | aacctctctg | gttccctccc | tagagagctt | 420 |
| ggagggttcc | ctatgctcca | aagtctctac | cttaacatta | actcattgga | gggtaccatc | 480 |
| cctcttgagc | ttggttatag | ctcctctctc | tctgagattg | atttgggtga | caatatgcta | 540 |
| ggtggggttc | ttccaccttc | tatttggaac | ttgtgtgaga | ggcttgtttc | ccttaggctc | 600 |
| cacggtaatt | ctttatctgg | gttagtttct | gagcctgcat | tgcctaactc | ttcttgcaag | 660 |
| aatctgcagg | tgcttgattt | gggtggcaac | aagttctctg | ggagtttccc | tgagttcatc | 720 |
| acaaagtttg | gtgcctaaa | gcagcttgac | ttggggaata | catgttat | gggtgcaatt | 780 |
| cctcaaggcc | tagctgggct | tagtcttgaa | aaattgaatc | tttcacacaa | taactttagt | 840 |
| ggggttttgc | ctttgtttgg | aggagaatcc | aagtttggtg | tggatgcttt | tgaggggaat | 900 |
| agccctagcc | tgtgtggacc | acctctggga | agctgtgcta | ggacctctac | actgagttct | 960 |
| ggtgctgttg | ctggcattgt | tattagtctg | atgacaggag | ctgtggtttt | ggcttctttg | 1020 |
| ctgatagggt | atatgcagaa | caagaagaag | aaggggagtg | gggagagtga | ggatgagttg | 1080 |
| aatgatgaag | aggaagatga | tgaagagaat | ggtggtaatg | ctattggtgg | agctggtgag | 1140 |
| gggaagctca | tgttatttgc | tggaggtgag | aatttgacat | tggatgatgt | gttgaatgca | 1200 |
| actgggcagg | ttttggagaa | gacttgttat | gggacggctt | ataaggctaa | gcttgctgat | 1260 |
| ggaggcacca | ttgctttgag | gctgttgaga | gaaggtagct | gcaaagacaa | ggcttcttgc | 1320 |
| ttgtctgtta | taaagcaatt | ggggaaaatt | cgccacgaga | atttgattcc | tttgagagct | 1380 |
| ttctatcagg | ggaagagagg | ggagaagctc | cttatttatg | actacctgcc | tctcagaacc | 1440 |
| cttcatgatc | ttttacatgg | agctaaagct | ggaaaaccag | tgttgaactg | gctaggcga | 1500 |
| cacaagattg | cgctgggcat | agcgagaggt | ctagcttatc | ttcacacagg | acttgaagtt | 1560 |
| cctgtcaccc | atgcaaacgt | aaggtccaag | aatgtgcttg | tggatgactt | ctttacagcc | 1620 |
| aggctcaccg | attttggtct | tgacaagctg | atgattcctt | ccatagccga | cgaaatggta | 1680 |
| gcgcttgcta | agacgacgg | ctacaaggct | cctgagcttc | aaagaatgaa | gaaatgcaac | 1740 |
| tccaggactg | atgtttatgc | attcggcata | ctgctgcttg | aaatcttgat | gggaagaag | 1800 |
| cctgggaaga | atggaagaaa | tggcgagtat | gtggacttgc | cttcgatggt | gaaagtggcg | 1860 |
| gttttggagg | agacgacgat | ggaagtgttt | gatgtgagc | ttttgaaagg | gataagaagc | 1920 |
| cctatggaag | atgggttggt | gcaggcgctg | aagctggcaa | tggggtgctg | tgcaccagtg | 1980 |
| gcatctgtta | ggccaagcat | ggatgaagtt | gtgaggcagt | tggaggagaa | tagaccaagg | 2040 |
| aacaggtctg | cattatacag | ccctacagaa | acaagaagtg | gaagtgttac | cccatttga | 2100 |

```
<210> SEQ ID NO 36
<211> LENGTH: 699
<212> TYPE: PRT
<213> ORGANISM: glycine max

<400> SEQUENCE: 36

Met Ala Phe Leu Asn Pro Phe Ser Leu His Ile Pro Met Ser Leu Leu
1               5                   10                  15

Phe Phe Phe Leu Phe Phe Phe Cys Phe Cys Lys Ala Ser Ser Thr Thr
            20                  25                  30

Thr Ser Thr Thr Lys Ser Leu Ser Pro Pro Ser Ser Pro Ser Thr Thr
        35                  40                  45

Ser Ser Ser Asp Val Glu Leu Leu Gly Lys Ile Lys Ala Ser Leu
    50                  55                  60

Gln Gly Ser Asn Ser Asp Asn Leu Val Leu Ser Ser Trp Asn Ser Ser
65                  70                  75                  80

Thr Pro Leu Cys Gln Trp Lys Gly Leu Ile Trp Val Phe Ser Asn Gly
                85                  90                  95

Thr Pro Leu Ser Cys Thr Asp Leu Ser Ser Pro Gln Trp Thr Asn Leu
            100                 105                 110

Thr Leu Leu Lys Asp Pro Ser Leu His Leu Phe Ser Leu Arg Leu Pro
        115                 120                 125

Ser Ala Asn Leu Ser Gly Ser Leu Pro Arg Glu Leu Gly Gly Phe Pro
    130                 135                 140

Met Leu Gln Ser Leu Tyr Leu Asn Ile Asn Ser Leu Glu Gly Thr Ile
145                 150                 155                 160

Pro Leu Glu Leu Gly Tyr Ser Ser Ser Leu Ser Glu Ile Asp Leu Gly
                165                 170                 175

Asp Asn Met Leu Gly Gly Val Leu Pro Pro Ser Ile Trp Asn Leu Cys
            180                 185                 190

Glu Arg Leu Val Ser Leu Arg Leu His Gly Asn Ser Leu Ser Gly Leu
        195                 200                 205

Val Ser Glu Pro Ala Leu Pro Asn Ser Ser Cys Lys Asn Leu Gln Val
    210                 215                 220

Leu Asp Leu Gly Gly Asn Lys Phe Ser Gly Ser Phe Pro Glu Phe Ile
225                 230                 235                 240

Thr Lys Phe Gly Gly Leu Lys Gln Leu Asp Leu Gly Asn Asn Met Phe
                245                 250                 255

Met Gly Ala Ile Pro Gln Gly Leu Ala Gly Leu Ser Leu Glu Lys Leu
            260                 265                 270

Asn Leu Ser His Asn Asn Phe Ser Gly Val Leu Pro Leu Phe Gly Gly
        275                 280                 285

Glu Ser Lys Phe Gly Val Asp Ala Phe Glu Gly Asn Ser Pro Ser Leu
    290                 295                 300

Cys Gly Pro Pro Leu Gly Ser Cys Ala Arg Thr Ser Thr Leu Ser Ser
305                 310                 315                 320

Gly Ala Val Ala Gly Ile Val Ile Ser Leu Met Thr Gly Ala Val Val
                325                 330                 335

Leu Ala Ser Leu Leu Ile Gly Tyr Met Gln Asn Lys Lys Lys Lys Gly
            340                 345                 350

Ser Gly Glu Ser Glu Asp Glu Leu Asn Asp Glu Glu Asp Asp Glu
        355                 360                 365

Glu Asn Gly Gly Asn Ala Ile Gly Gly Ala Gly Glu Gly Lys Leu Met
370                 375                 380
```

Leu Phe Ala Gly Gly Glu Asn Leu Thr Leu Asp Asp Val Leu Asn Ala
385                 390                 395                 400

Thr Gly Gln Val Leu Glu Lys Thr Cys Tyr Gly Thr Ala Tyr Lys Ala
            405                 410                 415

Lys Leu Ala Asp Gly Gly Thr Ile Ala Leu Arg Leu Leu Arg Glu Gly
        420                 425                 430

Ser Cys Lys Asp Lys Ala Ser Cys Leu Ser Val Ile Lys Gln Leu Gly
        435                 440                 445

Lys Ile Arg His Glu Asn Leu Ile Pro Leu Arg Ala Phe Tyr Gln Gly
    450                 455                 460

Lys Arg Gly Glu Lys Leu Leu Ile Tyr Asp Tyr Leu Pro Leu Arg Thr
465                 470                 475                 480

Leu His Asp Leu Leu His Gly Ala Lys Ala Gly Lys Pro Val Leu Asn
                485                 490                 495

Trp Ala Arg Arg His Lys Ile Ala Leu Gly Ile Ala Arg Gly Leu Ala
                500                 505                 510

Tyr Leu His Thr Gly Leu Glu Val Pro Val Thr His Ala Asn Val Arg
            515                 520                 525

Ser Lys Asn Val Leu Val Asp Asp Phe Phe Thr Ala Arg Leu Thr Asp
        530                 535                 540

Phe Gly Leu Asp Lys Leu Met Ile Pro Ser Ile Ala Asp Glu Met Val
545                 550                 555                 560

Ala Leu Ala Lys Thr Asp Gly Tyr Lys Ala Pro Glu Leu Gln Arg Met
                565                 570                 575

Lys Lys Cys Asn Ser Arg Thr Asp Val Tyr Ala Phe Gly Ile Leu Leu
                580                 585                 590

Leu Glu Ile Leu Ile Gly Lys Lys Pro Gly Lys Asn Gly Arg Asn Gly
            595                 600                 605

Glu Tyr Val Asp Leu Pro Ser Met Val Lys Val Ala Leu Glu Glu
        610                 615                 620

Thr Thr Met Glu Val Phe Asp Val Glu Leu Leu Lys Gly Ile Arg Ser
625                 630                 635                 640

Pro Met Glu Asp Gly Leu Val Gln Ala Leu Lys Leu Ala Met Gly Cys
                645                 650                 655

Cys Ala Pro Val Ala Ser Val Arg Pro Ser Met Asp Glu Val Val Arg
                660                 665                 670

Gln Leu Glu Glu Asn Arg Pro Arg Asn Arg Ser Ala Leu Tyr Ser Pro
            675                 680                 685

Thr Glu Thr Arg Ser Gly Ser Val Thr Pro Phe
    690                 695

<210> SEQ ID NO 37
<211> LENGTH: 1989
<212> TYPE: DNA
<213> ORGANISM: oryza sativa

<400> SEQUENCE: 37
atgagatctg tgatgatgtg ctgcctcctc ctcctcctgg tctctgccgc tgccggggcc      60
gagggcaagt cggaggtggc gctcctcctg gagcgcgtga agccggcgct gcaggggag     120 ggcgaagtag gagggaacgc gcagctggcc acctggaccg cctccacccc gctctgccag    180
tggcgcggcc tccgctggtc caccgccgcc accctccccc gcgagctccc ctgcggcaac    240
ctctctgcag gcctcgccca ccaccccggtc ccggacgacc tcctcctcct cctctccatc    300
cgcctcccgg cctccgccct cgccggccac ctccctcccg aactcgccgc tttctccgcc    360

-continued

```
ctcgcctcca tcttcctcgc ccacaactcc ctctccgggc ccatccccct cgccctcggc    420
aacgcccccg ccctctccct cctcgacctc gcctccaacc gcctctccgg ctccctcccg    480
ctctccatct ggaacctctg cagcggcaac gcccgtctct ccctcctccg cctccacggc    540
aacgccctcc acggcccaat ccccgacccc gccgccctcg cccccaacac cacctgcgac    600
gccctcagcc tcctcgacct ctcgccaaac cgcctctccg ccccttcccc ctcctcccta    660
gtcaccaccg ccttccccgc cctccgctcc ctcgacctct ccgacaaccg cctccacggt    720
cccatcccgc acggcctcgc cccatccac tccctcaacc tctcctacaa caacttctcc     780
ggccaacttc ccccgacct cgcctctctg ccgcccgacg ccttcctcgc caacagcccc     840
gcgctctgcg gccgccgct gccccaccac tgcctcccca gcaaccccct cacctcctcc     900
gccgtcgccg ccatcgtcat tgccctcatg gccgccgccg tcgtcctggc ttccctctcc    960
atcggctggg cgcagggccg ttggaggcga cgcccttgc cgccggagga agggacactc    1020
acggaggacg gcgaggggaa gctggtggtg ttccagggcg gggagcacct cacgctggag    1080
gaggtgctca acgccacggg gcaggtggtc aacaaggcca gctactgcac cgtctacaag    1140
gccaagctgg cggagggcgg cggcagcatc gagctgcgcc tcctccgcga gggctgctgc    1200
aaggacgccg agtcgtgcgc gccggcggtg cgccgcatcg gccgcgcgcg ccacgacaac    1260
ctggttccgc tgcgcgcctt ctaccagggg cgccgcggag agaagctgct ggtgtacgac    1320
tacttccccg gcaaccggac gctccacgag ctcctccacg ccacggggga gcagagccag    1380
gggatgaggc cggcgttgac cgtgggcgcg cggcacaaga tcgcgctggg cgtggcgcgc    1440
gcgctggcgt acgtgcacgc ggggcacggc gaggcgcacg cagcgtgcg ctcgtccaac     1500
gtgctggtgg acgagtggtt cgtggcgagg gtggcggagt acgcagtgca ccggctgctg    1560
gtggcggcgg cggtggggaa gcggacgggc tacagggcgc cggagctgca gtcgaggggg    1620
aggtgcagcc cgcggacgga cgtgtacgcg ttcgggatat tgctgctgga gctgctgatg    1680
gggcggaagg cgtcgggaga gctgccggcg gtggtgaagg cggcggtgct ggaggaggtg    1740
acgatgatgg aggtgttcga cgcggaggtg gcgcgcgggg tgcgtagccc cgcggaggag    1800
gggctgcttc aggcgctgaa gctggcgatg gggtgctgcg cgccggtggc ttcggcaagg    1860
cccaccatgg cggaggtggt gcggcagctg gaggaggtcc ggccccggaa cagcagccgg    1920
ccgtcggcga tctacagccc cgccgagccc aggagcgacg ccggcacgcc caccgccgcc    1980
gccgtctaa                                                           1989
```

<210> SEQ ID NO 38
<211> LENGTH: 662
<212> TYPE: PRT
<213> ORGANISM: oryza sativa

<400> SEQUENCE: 38

```
Met Arg Ser Val Met Met Cys Cys Leu Leu Leu Leu Val Ser Ala
1               5                   10                  15

Ala Ala Gly Ala Glu Gly Lys Ser Glu Val Ala Leu Leu Leu Glu Arg
                20                  25                  30

Val Lys Pro Ala Leu Gln Gly Glu Gly Val Gly Gly Asn Ala Gln
            35                  40                  45

Leu Ala Thr Trp Thr Ala Ser Thr Pro Leu Cys Gln Trp Arg Gly Leu
        50                  55                  60

Arg Trp Ser Thr Ala Ala Thr Leu Pro Arg Glu Leu Pro Cys Gly Asn
65                  70                  75                  80
```

```
Leu Ser Ala Gly Leu Ala His His Pro Val Pro Asp Asp Leu Leu Leu
                85                  90                  95
Leu Leu Ser Ile Arg Leu Pro Ala Ser Ala Leu Ala Gly His Leu Pro
            100                 105                 110
Pro Glu Leu Ala Ala Phe Ser Ala Leu Ala Ser Ile Phe Leu Ala His
        115                 120                 125
Asn Ser Leu Ser Gly Pro Ile Pro Leu Ala Leu Gly Asn Ala Pro Ala
    130                 135                 140
Leu Ser Leu Leu Asp Leu Ala Ser Asn Arg Leu Ser Gly Ser Leu Pro
145                 150                 155                 160
Leu Ser Ile Trp Asn Leu Cys Ser Gly Asn Ala Arg Leu Ser Leu Leu
                165                 170                 175
Arg Leu His Gly Asn Ala Leu His Gly Pro Ile Pro Asp Pro Ala Ala
            180                 185                 190
Leu Ala Pro Asn Thr Thr Cys Asp Ala Leu Ser Leu Leu Asp Leu Ser
        195                 200                 205
Ala Asn Arg Leu Ser Gly Pro Phe Pro Ser Ser Leu Val Thr Thr Ala
    210                 215                 220
Phe Pro Ala Leu Arg Ser Leu Asp Leu Ser Asp Asn Arg Leu His Gly
225                 230                 235                 240
Pro Ile Pro His Gly Leu Ala Pro Ile His Ser Leu Asn Leu Ser Tyr
                245                 250                 255
Asn Asn Phe Ser Gly Gln Leu Pro Pro Asp Leu Ala Ser Leu Pro Pro
            260                 265                 270
Asp Ala Phe Leu Ala Asn Ser Pro Ala Leu Cys Gly Pro Pro Leu Pro
        275                 280                 285
His His Cys Leu Pro Ser Asn Pro Leu Thr Ser Ser Ala Val Ala Ala
    290                 295                 300
Ile Val Ile Ala Leu Met Ala Ala Ala Val Leu Ala Ser Leu Ser
305                 310                 315                 320
Ile Gly Trp Ala Gln Gly Arg Trp Arg Arg Ala Pro Leu Pro Pro Glu
                325                 330                 335
Glu Gly Thr Leu Thr Glu Asp Gly Glu Gly Lys Leu Val Phe Gln
            340                 345                 350
Gly Gly Glu His Leu Thr Leu Glu Glu Val Leu Asn Ala Thr Gly Gln
        355                 360                 365
Val Val Asn Lys Ala Ser Tyr Cys Thr Val Tyr Lys Ala Lys Leu Ala
    370                 375                 380
Glu Gly Gly Gly Ser Ile Glu Leu Arg Leu Leu Arg Glu Gly Cys Cys
385                 390                 395                 400
Lys Asp Ala Glu Ser Cys Ala Pro Ala Val Arg Arg Ile Gly Arg Ala
                405                 410                 415
Arg His Asp Asn Leu Val Pro Leu Arg Ala Phe Tyr Gln Gly Arg Arg
            420                 425                 430
Gly Glu Lys Leu Leu Val Tyr Asp Tyr Phe Pro Gly Asn Arg Thr Leu
        435                 440                 445
His Glu Leu Leu His Gly His Gly Glu Gln Ser Gln Gly Met Arg Pro
    450                 455                 460
Ala Leu Thr Trp Ala Arg Arg His Lys Ile Ala Leu Gly Val Ala Arg
465                 470                 475                 480
Ala Leu Ala Tyr Val His Ala Gly His Gly Glu Ala His Gly Ser Val
                485                 490                 495
```

Arg Ser Ser Asn Val Leu Val Asp Glu Trp Phe Val Ala Arg Val Ala
                500                 505                 510

Glu Tyr Ala Val His Arg Leu Leu Val Ala Ala Ala Val Gly Lys Ala
        515                 520                 525

Asp Gly Tyr Arg Ala Pro Glu Leu Gln Ser Arg Gly Arg Cys Ser Pro
    530                 535                 540

Arg Thr Asp Val Tyr Ala Phe Gly Ile Leu Leu Glu Leu Leu Met
545                 550                 555                 560

Gly Arg Lys Ala Ser Gly Glu Leu Pro Ala Val Lys Ala Val
                565                 570                 575

Leu Glu Glu Val Thr Met Met Glu Val Phe Asp Ala Val Ala Arg
            580                 585                 590

Gly Val Arg Ser Pro Ala Glu Glu Gly Leu Leu Gln Ala Leu Lys Leu
        595                 600                 605

Ala Met Gly Cys Cys Ala Pro Val Ala Ser Ala Arg Pro Thr Met Ala
        610                 615                 620

Glu Val Val Arg Gln Leu Glu Glu Val Arg Pro Arg Asn Ser Ser Arg
625                 630                 635                 640

Pro Ser Ala Ile Tyr Ser Pro Ala Glu Pro Arg Ser Asp Ala Gly Thr
                645                 650                 655

Pro Thr Ala Ala Ala Val
            660

<210> SEQ ID NO 39
<211> LENGTH: 1254
<212> TYPE: DNA
<213> ORGANISM: Gossypium hirsutum

<400> SEQUENCE: 39

```
tcccttgatt taggtaacaa caagttttta ggggatttcc cagagtttgt aactaggttt      60
caagctctta gagagcttga tctttcgagt aacatgcttt caggtcaaat tccacagagt     120
ttggccactt taaacgtgga aaaattaaac ctttcccaca ataacttcac tggaatgttg     180 cctgttttg gtgaaagaaa gtttggcccg gaggctttcg aagggaacaa tccagggcta     240
tgtgggttgc ctttgaatag ttgtagtggc aggtcacagc tgagtccagg tgcaattgct     300
ggcattgtga ttggtctaat gactggagtg gtagttttgg catcattgtt cgttggctat     360
atgcaaaaca ggaagaggag cagcaatgga gatagtgagg aggaactgga agaaggagag     420
ggggatgaaa acggggtcgg gggagttgtc agcgagagca agcttatttt gtttcaaggc     480
ggggagcatt tgacattaga ggatgtactg aatgcaactg gtcaagtcat ggagaagaca     540
aattatggga ctgttttataa ggcaaagctt gctgatggtg gaaatatagc attgaggttg     600
ttgagggaag gcagttgtaa ggacgggagt tcatgtctgc ctgtcataaa gcagctgggg     660
aaggttagac atgagaattt ggttccactg agagcattct atcagggggaa agaggggaa     720 aagcttctaa tttatgacta tcttccaaat agaagcctac atgactttt acatggtatg     780 caagcaggaa agccagttct aaattgggct cgacggcaca aaatcgcatt ggggatagcc     840
aaaggattag cacatcttca tacaggtctc gagatgccga tcacccatgg gaatgttagg     900
tccaaaaatg tgcttgtaga tgacttcttt gtagccaggc tcaccgaata tggactcgac     960
aagctaatga tcccggctgt ggctgatgaa atggttgccc tcgcaaagac cgaatgttac    1020
aaggcaccgg aacttcaaag catgaagaaa tgcaacacca gaactgacgt ttatgcattt    1080
gggatattgt tattagagat tttgatagcc aagaagcctg agaaaatgc aagacgcaac    1140
```

```
gatgttgggg atttgccttc gattgtgaaa gcagcagttt tggaagagac aacaatggag   1200
gttttcgacg tagaagtgtt gaaggtattc gaagtccgat ggaagacggg atag         1254
```

<210> SEQ ID NO 40
<211> LENGTH: 417
<212> TYPE: PRT
<213> ORGANISM: Gossypium hirsutum

<400> SEQUENCE: 40

```
Ser Leu Asp Leu Gly Asn Asn Lys Phe Leu Gly Asp Phe Pro Glu Phe
1               5                   10                  15

Val Thr Arg Phe Gln Ala Leu Arg Glu Leu Asp Leu Ser Ser Asn Met
            20                  25                  30

Leu Ser Gly Gln Ile Pro Gln Ser Leu Ala Thr Leu Asn Val Glu Lys
        35                  40                  45

Leu Asn Leu Ser His Asn Asn Phe Thr Gly Met Leu Pro Val Phe Gly
    50                  55                  60

Glu Arg Lys Phe Gly Pro Glu Ala Phe Glu Gly Asn Asn Pro Gly Leu
65                  70                  75                  80

Cys Gly Leu Pro Leu Asn Ser Cys Ser Gly Arg Ser Gln Leu Ser Pro
                85                  90                  95

Gly Ala Ile Ala Gly Ile Val Ile Gly Leu Met Thr Gly Val Val Val
            100                 105                 110

Leu Ala Ser Leu Phe Val Gly Tyr Met Gln Asn Arg Lys Arg Ser Ser
        115                 120                 125

Asn Gly Asp Ser Glu Glu Glu Leu Glu Glu Gly Glu Gly Asp Glu Asn
    130                 135                 140

Gly Val Gly Val Val Ser Glu Ser Lys Leu Ile Leu Phe Gln Gly
145                 150                 155                 160

Gly Glu His Leu Thr Leu Glu Asp Val Leu Asn Ala Thr Gly Gln Val
                165                 170                 175

Met Glu Lys Thr Asn Tyr Gly Thr Val Tyr Lys Ala Lys Leu Ala Asp
            180                 185                 190

Gly Gly Asn Ile Ala Leu Arg Leu Leu Arg Glu Gly Ser Cys Lys Asp
        195                 200                 205

Gly Ser Ser Cys Leu Pro Val Ile Lys Gln Leu Gly Lys Val Arg His
    210                 215                 220

Glu Asn Leu Val Pro Leu Arg Ala Phe Tyr Gln Gly Lys Arg Gly Glu
225                 230                 235                 240

Lys Leu Leu Ile Tyr Asp Tyr Leu Pro Asn Arg Ser Leu His Asp Phe
                245                 250                 255

Leu His Gly Met Gln Ala Gly Lys Pro Val Leu Asn Trp Ala Arg Arg
            260                 265                 270

His Lys Ile Ala Leu Gly Ile Ala Lys Gly Leu Ala His Leu His Thr
        275                 280                 285

Gly Leu Glu Met Pro Ile Thr His Gly Asn Val Arg Ser Lys Asn Val
    290                 295                 300

Leu Val Asp Asp Phe Phe Val Ala Arg Leu Thr Glu Tyr Gly Leu Asp
305                 310                 315                 320

Lys Leu Met Ile Pro Ala Val Ala Asp Glu Met Val Ala Leu Ala Lys
                325                 330                 335

Thr Glu Cys Tyr Lys Ala Pro Glu Leu Gln Ser Met Lys Lys Cys Asn
            340                 345                 350

Thr Arg Thr Asp Val Tyr Ala Phe Gly Ile Leu Leu Leu Glu Ile Leu
```

```
                355                 360                 365
Ile Gly Lys Lys Pro Glu Lys Asn Ala Arg Arg Asn Asp Val Gly Asp
        370                 375                 380

Leu Pro Ser Ile Val Lys Ala Ala Val Leu Glu Thr Thr Met Glu
385                 390                 395                 400

Val Phe Asp Val Glu Val Leu Lys Val Phe Glu Val Arg Trp Lys Thr
                405                 410                 415

Gly

<210> SEQ ID NO 41
<211> LENGTH: 1263
<212> TYPE: DNA
<213> ORGANISM: arabidopsis thaliana

<400> SEQUENCE: 41
```

| | | | | | |
|---|---|---|---|---|---|
| atgaaatgct | tcttattccc | tcttggggac | aagaaagatg | aacagagaag | ccctaaaccg | 60 |
| gtttcaccaa | cgtctaactt | cagtgacgta | aacaaaagcg | gttcagattt | cagtccccgg | 120 |
| gatgtttctg | gaacgagcac | agtatcatcc | actggtagga | actcgaacac | tagcatgtca | 180 |
| gctagagaaa | acaaccttag | agagttcact | attggtgatc | ttaaatctgc | acaaggaac | 240 |
| ttcagcaggt | caggtatgat | cggggaaggc | ggttttggtt | gtgtcttctg | gggaacaatc | 300 |
| aagaacttag | aagacccatc | gaagaaaatc | gaagtcgcgg | ttaaacagct | cggcaaaaga | 360 |
| gggttgcagg | tcataaaga | atgggtgact | gaagtgaact | ttctcggtgt | agtcgagcat | 420 |
| tcaaacttgg | tgaagttgct | gggacattgt | gcagaagacg | atgaacgtgg | aatccaaagg | 480 |
| cttttggttt | atgaatatat | gccaaaccaa | agtgtcgagt | ccatttatc | tccgcggtca | 540 |
| ccgacagtac | ttacttggga | cctcagattg | agaatagcac | aagacgcagc | tcgaggttta | 600 |
| acataccttc | atgaagaaat | ggactttcag | ataatattcc | gtgatttcaa | gtcatccaac | 660 |
| attctactag | acgagaattg | gacagcgaag | ctttcggatt | tcggtttggc | tcgcttaggt | 720 |
| ccttcaccag | gatccagcca | tgtttctact | gatgtagtag | aacaatggg | atacgcagct | 780 |
| ccagagtata | tccaaacggg | tcgcctcacg | tcgaaaagcg | atgtgtgggg | atacggagtt | 840 |
| ttcatctatg | agctcattac | aggaagaagg | ccactagacc | ggaacaagcc | taaggagag | 900 |
| cagaagcttt | tagaatgggt | gagaccttac | ttatccgaca | caaggaggtt | ccggctaata | 960 |
| gtagacccga | ggctcgaggg | aaagtacatg | atcaagtcag | tgcagaaact | cgcggttgta | 1020 |
| gccaaccttt | gccttactag | aaacgcaaag | gcgcgtccaa | agatgagcga | ggtgttagag | 1080 |
| atggtgacaa | agattgtgga | agcttcatcg | cctgggaatg | tggcaagaa | gccgcagctg | 1140 |
| gttccactaa | agagtcaaga | aacttctaga | gtcgaggaag | ggaagaataa | gaaggttctt | 1200 |
| gatggtgctg | aaggaggttg | gttagaaaag | ttgtggaacc | caaagaatgt | gagagcttgt | 1260 |
| tga | | | | | | 1263 |

```
<210> SEQ ID NO 42
<211> LENGTH: 420
<212> TYPE: PRT
<213> ORGANISM: arabidopsis thaliana

<400> SEQUENCE: 42

Met Lys Cys Phe Leu Phe Pro Leu Gly Asp Lys Lys Asp Glu Gln Arg
1               5                   10                  15

Ser Pro Lys Pro Val Ser Pro Thr Ser Asn Phe Ser Asp Val Asn Lys
            20                  25                  30
```

Ser Gly Ser Asp Phe Ser Pro Arg Asp Val Ser Gly Thr Ser Thr Val
            35                  40                  45

Ser Ser Thr Gly Arg Asn Ser Asn Thr Ser Met Ser Ala Arg Glu Asn
 50                  55                  60

Asn Leu Arg Glu Phe Thr Ile Gly Asp Leu Lys Ser Ala Thr Arg Asn
 65                  70                  75                  80

Phe Ser Arg Ser Gly Met Ile Gly Glu Gly Phe Gly Cys Val Phe
                 85                  90                  95

Trp Gly Thr Ile Lys Asn Leu Glu Asp Pro Ser Lys Lys Ile Glu Val
                100                 105                 110

Ala Val Lys Gln Leu Gly Lys Arg Gly Leu Gln Gly His Lys Glu Trp
                115                 120                 125

Val Thr Glu Val Asn Phe Leu Gly Val Val Glu His Ser Asn Leu Val
                130                 135                 140

Lys Leu Leu Gly His Cys Ala Glu Asp Asp Glu Arg Gly Ile Gln Arg
145                 150                 155                 160

Leu Leu Val Tyr Glu Tyr Met Pro Asn Gln Ser Val Glu Phe His Leu
                165                 170                 175

Ser Pro Arg Ser Pro Thr Val Leu Thr Trp Asp Leu Arg Leu Arg Ile
                180                 185                 190

Ala Gln Asp Ala Ala Arg Gly Leu Thr Tyr Leu His Glu Glu Met Asp
                195                 200                 205

Phe Gln Ile Ile Phe Arg Asp Phe Lys Ser Ser Asn Ile Leu Leu Asp
                210                 215                 220

Glu Asn Trp Thr Ala Lys Leu Ser Asp Phe Gly Leu Ala Arg Leu Gly
225                 230                 235                 240

Pro Ser Pro Gly Ser Ser His Val Ser Thr Asp Val Val Gly Thr Met
                245                 250                 255

Gly Tyr Ala Ala Pro Glu Tyr Ile Gln Thr Gly Arg Leu Thr Ser Lys
                260                 265                 270

Ser Asp Val Trp Gly Tyr Gly Val Phe Ile Tyr Glu Leu Ile Thr Gly
                275                 280                 285

Arg Arg Pro Leu Asp Arg Asn Lys Pro Lys Gly Glu Gln Lys Leu Leu
290                 295                 300

Glu Trp Val Arg Pro Tyr Leu Ser Asp Thr Arg Arg Phe Arg Leu Ile
305                 310                 315                 320

Val Asp Pro Arg Leu Glu Gly Lys Tyr Met Ile Lys Ser Val Gln Lys
                325                 330                 335

Leu Ala Val Ala Asn Leu Cys Leu Thr Arg Asn Ala Lys Ala Arg
                340                 345                 350

Pro Lys Met Ser Glu Val Leu Glu Met Val Thr Lys Ile Val Glu Ala
                355                 360                 365

Ser Ser Pro Gly Asn Gly Lys Lys Pro Gln Leu Val Pro Leu Lys
                370                 375                 380

Ser Gln Glu Thr Ser Arg Val Glu Glu Gly Lys Asn Lys Lys Val Leu
385                 390                 395                 400

Asp Gly Ala Glu Gly Gly Trp Leu Glu Lys Leu Trp Asn Pro Lys Asn
                405                 410                 415

Val Arg Ala Cys
            420

<210> SEQ ID NO 43
<211> LENGTH: 1296
<212> TYPE: DNA

<213> ORGANISM: zea mays

<400> SEQUENCE: 43

```
atgaggtgcc tgcctttctt gcatggagac accaaagaga aggatccagt cactaagtcg      60
gcctctctac ggtccatgag cacaacatca acggagcgcg atgtccgctc cggttcagac     120
ttcacctcct tgaatgtttc cgacatgagc gccgagtcga taaggaggac gcagtacccc     180
agcttcactg accgcccgtc taacctgagg gtgttctcct tgctgaact gaagagtgcc      240
acccgcaact tcagccggtc tctcatggtt ggcgagggtg gctttggctg tgtgtacagg     300
ggtgtcatca agacctccga tgaaccgaac gaacgaattg agatcgctgt taagcagttg     360
aatcgtaaag gacttcaggg gcagaaggag tggttaacag agatgaatgt gcttggaatt     420
gtggatcatc caaacctagt taaacttata ggctactgtg ctgaagatga tgagagggga     480
gtacaacggc ttttagtgta cgaatatatg cctaatggaa gtgtggatga tcacttgtcg     540
agtaggtcaa cttctactct gtcatggcca atgagactaa agtagctct tgattctgct      600
cggggactga agtatctgca tgaagaaatg gaattccagg ttattttccg ggacctgaaa     660
acatctaaca ttttgttgga tgagaactgg aatgctaaac tgtcagactt tggtttggct     720
aggcatggac cagcagaagg tctgacccat gtctccacag cggtggtcgg gactctaggc     780
tacgcagctc cagagtacat gcagactggg cgcctgaccg cgaagagcga catatggagc     840
tacggcgtcc tcctgtacga gctgatcaca ggccgccgcc ccatcgaccg gaaccgccca     900
aagagcgagc agaagctcct ggactgggtg aagccgtaca tctcggacgt gaacggttc      960
cccatcatcg tcgacccgcg gctggagggg cactacaacc tcaagtccat gacgaagctg    1020
tccagtgtgg cgaaccggtg cctggtccgg atgcccaagt ctcgccccaa gatgagcgag    1080
gtgtacgaca tggtgcagaa gatcgtggac tgcgtgggga ccggcccgcc gcagcccccg    1140
ctgctgcact accacggctc ggcctctgag cctggccctg cgacaagcg cgccaggaaa     1200
gggtcggtga agaggaggag gctctgggag ctcaggttcg gctgccggca catcgtgtgg    1260
cgcggctgga agcctgcgat cgtgaaggac atctga                              1296
```

<210> SEQ ID NO 44
<211> LENGTH: 431
<212> TYPE: PRT
<213> ORGANISM: zea mays

<400> SEQUENCE: 44

```
Met Arg Cys Leu Pro Phe Leu His Gly Asp Thr Lys Glu Lys Asp Pro
1               5                   10                  15

Val Thr Lys Ser Ala Ser Leu Arg Ser Met Ser Thr Thr Ser Thr Glu
            20                  25                  30

Arg Asp Val Arg Ser Gly Ser Asp Phe Thr Ser Leu Asn Val Ser Asp
        35                  40                  45

Met Ser Ala Glu Ser Ile Arg Arg Thr Gln Tyr Pro Ser Phe Thr Asp
    50                  55                  60

Arg Pro Ser Asn Leu Arg Val Phe Ser Phe Ala Glu Leu Lys Ser Ala
65                  70                  75                  80

Thr Arg Asn Phe Ser Arg Ser Leu Met Val Gly Glu Gly Gly Phe Gly
                85                  90                  95

Cys Val Tyr Arg Gly Val Ile Lys Thr Ser Asp Glu Pro Asn Glu Arg
            100                 105                 110

Ile Glu Ile Ala Val Lys Gln Leu Asn Arg Lys Gly Leu Gln Gly Gln
        115                 120                 125
```

```
Lys Glu Trp Leu Thr Glu Met Asn Val Leu Gly Ile Val Asp His Pro
    130                 135                 140
Asn Leu Val Lys Leu Ile Gly Tyr Cys Ala Glu Asp Glu Arg Gly
145                 150                 155                 160
Val Gln Arg Leu Leu Val Tyr Glu Tyr Met Pro Asn Gly Ser Val Asp
                165                 170                 175
Asp His Leu Ser Ser Arg Ser Thr Ser Thr Leu Ser Trp Pro Met Arg
            180                 185                 190
Leu Lys Val Ala Leu Asp Ser Ala Arg Gly Leu Lys Tyr Leu His Glu
        195                 200                 205
Glu Met Glu Phe Gln Val Ile Phe Arg Asp Leu Lys Thr Ser Asn Ile
    210                 215                 220
Leu Leu Asp Glu Asn Trp Asn Ala Lys Leu Ser Asp Phe Gly Leu Ala
225                 230                 235                 240
Arg His Gly Pro Ala Glu Gly Leu Thr His Val Ser Thr Ala Val Val
                245                 250                 255
Gly Thr Leu Gly Tyr Ala Ala Pro Glu Tyr Met Gln Thr Gly Arg Leu
            260                 265                 270
Thr Ala Lys Ser Asp Ile Trp Ser Tyr Gly Val Leu Leu Tyr Glu Leu
        275                 280                 285
Ile Thr Gly Arg Arg Pro Ile Asp Arg Asn Arg Pro Lys Ser Glu Gln
    290                 295                 300
Lys Leu Leu Asp Trp Val Lys Pro Tyr Ile Ser Asp Val Lys Arg Phe
305                 310                 315                 320
Pro Ile Ile Val Asp Pro Arg Leu Glu Gly His Tyr Asn Leu Lys Ser
                325                 330                 335
Met Thr Lys Leu Ser Ser Val Ala Asn Arg Cys Leu Val Arg Met Pro
            340                 345                 350
Lys Ser Arg Pro Lys Met Ser Glu Val Tyr Asp Met Val Gln Lys Ile
        355                 360                 365
Val Asp Cys Val Gly Thr Gly Pro Pro Gln Pro Leu Leu His Tyr
    370                 375                 380
His Gly Ser Ala Ser Glu Pro Gly Pro Gly Asp Lys Arg Ala Arg Lys
385                 390                 395                 400
Gly Ser Val Lys Arg Arg Arg Leu Trp Glu Leu Arg Phe Gly Cys Arg
                405                 410                 415
His Ile Val Trp Arg Gly Trp Lys Pro Ala Ile Val Lys Asp Ile
            420                 425                 430

<210> SEQ ID NO 45
<211> LENGTH: 1287
<212> TYPE: DNA
<213> ORGANISM: glycine max

<400> SEQUENCE: 45
atgaagtgtt ttccattctc gtatggagag aaaaaagatg aaccgaaagg cttgcagttg      60
cagtcaacat cgggtcgatc tgacaattcc atgtgtgttg aggctgaggt tagaagatcc     120
ggttctgagt taaattctca ggatgtttcg acaatggca gctcagaatc ccagaggagg      180
aatgcaattc ccagtttgtc ccagagaccc agcaacctca gagtgtttac tgtatctgaa     240
ctgaaatcag ccaccaagaa tttcagtcgc tctgttatga tcggagaggg tgggtttggg     300
tgtgtctacc tgggattgat aagaagcgca gaggactcct ccagaagaat tgaagttgca     360
gttaaacaac ttagtaaaag aggaatgcag ggccataggg aatgggtgac agaagtgaat     420
```

```
gttctgggca ttgttgagca tcccaatctt gtgaaactag tgggttactg tgctgatgat      480
gatgaaagag gaatccagag gcttctaatt tatgaataca tgccaaacag aagtgtggaa      540
caccatttat ctcaccgatc agagactcct ctcccatgga ctaggagatt aaaaatagct      600
cgagatgcag ctcgtgggtt aacatacctg catgaggaaa tggatttcca gataattttc      660
agagatttca atcttcaaa tatcctattg gatgaacagt ggaatgcaaa gctatcagac       720
tttgggttag caaggttggg accatcagat ggactgactc atgtctcaac ggcggttgta      780
ggaacaatgg gatatgccgc tcctgaatat gttcaaaccg gacgtctaac ttcaaagaat      840
gatgtatgga gctacggtgt cttcctttat gaactcatca ctggtaggcg ccctttagat      900
cgaaatcgcc ccaggcgtga gcagaagttg ttggaatgga taaggccata cctatcagat      960
gggaagaaat tcaactaat attagatcca agacttgata agaaacaagt cttcaagtca     1020
gcccagagac tcgctatgat tgctaaccaa tgcttggcaa aaatcccaa gaatcgccca      1080 aagatgagtg aggtattgga aatggtaaat ggaatggtag aatcatcatc cagttctagt    1140
ccacagttgc ccctgaggag tgtggtgaca ttggaagctt cccaggatac tgaaacaaat    1200
aacaagaaac gaaccatgga tcagaagctc ggagaaagta attggtttgt taggatgtgg   1260
agaccaaagc ttgtaagaac atgctga                                        1287
```

<210> SEQ ID NO 46
<211> LENGTH: 428
<212> TYPE: PRT
<213> ORGANISM: glycine max

<400> SEQUENCE: 46

```
Met Lys Cys Phe Pro Phe Ser Tyr Gly Glu Lys Lys Asp Glu Pro Lys
1               5                   10                  15

Gly Leu Gln Leu Gln Ser Thr Ser Gly Arg Ser Asp Asn Ser Met Cys
            20                  25                  30

Val Glu Ala Glu Val Arg Arg Ser Gly Ser Glu Leu Asn Ser Gln Asp
        35                  40                  45

Val Ser Asp Asn Gly Ser Ser Glu Ser Gln Arg Arg Asn Ala Ile Pro
    50                  55                  60

Ser Leu Ser Gln Arg Pro Ser Asn Leu Arg Val Phe Thr Val Ser Glu
65                  70                  75                  80

Leu Lys Ser Ala Thr Lys Asn Phe Ser Arg Ser Val Met Ile Gly Glu
                85                  90                  95

Gly Gly Phe Gly Cys Val Tyr Leu Gly Leu Ile Arg Ser Ala Glu Asp
            100                 105                 110

Ser Ser Arg Arg Ile Glu Val Ala Val Lys Gln Leu Ser Lys Arg Gly
        115                 120                 125

Met Gln Gly His Arg Glu Trp Val Thr Glu Val Asn Val Leu Gly Ile
    130                 135                 140

Val Glu His Pro Asn Leu Val Lys Leu Val Gly Tyr Cys Ala Asp Asp
145                 150                 155                 160

Asp Glu Arg Gly Ile Gln Arg Leu Leu Ile Tyr Glu Tyr Met Pro Asn
                165                 170                 175

Arg Ser Val Glu His His Leu Ser His Arg Ser Glu Thr Pro Leu Pro
            180                 185                 190

Trp Thr Arg Arg Leu Lys Ile Ala Arg Asp Ala Ala Arg Gly Leu Thr
        195                 200                 205

Tyr Leu His Glu Glu Met Asp Phe Gln Ile Ile Phe Arg Asp Phe Lys
```

```
                    210                 215                 220
Ser Ser Asn Ile Leu Leu Asp Glu Gln Trp Asn Ala Lys Leu Ser Asp
225                 230                 235                 240

Phe Gly Leu Ala Arg Leu Gly Pro Ser Asp Gly Leu Thr His Val Ser
                245                 250                 255

Thr Ala Val Val Gly Thr Met Gly Tyr Ala Ala Pro Glu Tyr Val Gln
            260                 265                 270

Thr Gly Arg Leu Thr Ser Lys Asn Asp Val Trp Ser Tyr Gly Val Phe
                275                 280                 285

Leu Tyr Glu Leu Ile Thr Gly Arg Arg Pro Leu Asp Arg Asn Arg Pro
        290                 295                 300

Arg Arg Glu Gln Lys Leu Leu Glu Trp Ile Arg Pro Tyr Leu Ser Asp
305                 310                 315                 320

Gly Lys Lys Phe Gln Leu Ile Leu Asp Pro Arg Leu Asp Lys Lys Gln
                325                 330                 335

Val Phe Lys Ser Ala Gln Arg Leu Ala Met Ile Ala Asn Gln Cys Leu
            340                 345                 350

Ala Lys Asn Pro Lys Asn Arg Pro Lys Met Ser Glu Val Leu Glu Met
        355                 360                 365

Val Asn Gly Met Val Glu Ser Ser Ser Ser Ser Pro Gln Leu Pro
370                 375                 380

Leu Arg Ser Val Val Thr Leu Glu Ala Ser Gln Asp Thr Glu Thr Asn
385                 390                 395                 400

Asn Lys Lys Arg Thr Met Asp Gln Lys Leu Gly Glu Ser Asn Trp Phe
                405                 410                 415

Val Arg Met Trp Arg Pro Lys Leu Val Arg Thr Cys
            420                 425

<210> SEQ ID NO 47
<211> LENGTH: 1284
<212> TYPE: DNA
<213> ORGANISM: oryza sativa

<400> SEQUENCE: 47
atgaggtgcc tgcctttctt gcatggagat tccaaagagg aggatcccgt caacaagtcg      60
gcttctgtcc ggtcgttgag cacaacatcg acggagcggg atgtccggtc cggctccgac     120
ttcaactcct tgaatgtctc tgacatgagt gccgaatcaa tacggaggac acagtatccc     180
agcttcactg atcggcccag taacctcagg gtgttctctt tctctgagct gaagaatgcc     240
actcgcaatt ttagccggtc tcttatggtt ggtgagggtg ggtttggatg tgtgtatagg     300
ggtgtcatca agaattccga tgaaccaact gagcgcaccg agattgctgt taaacagctg     360
aatcgcaaag gacttcaggg gcagaaagaa tggttaacag aactgaatgt gcttgggatt     420
gtagagcatc caaacctcgt caaactaatt ggctactgcg ctgaagatga tgaaaggggc     480
gtacagcgtc tcctagtata cgaatacatg cctaatggaa gcgtggatga tcacttgtca     540
agtaggtcaa attcaactct atcatggcca atgagactaa agtagctct ggacgctgct     600 cggggactga agtatctgca tgaagagatg gaatttcagg ttatcttccg tgacctaaaa     660
acatctaaca ttctgttaga tgagaactgg aatgcaaagt tgtctgactt tggattggct     720
aggcatggac catcagaagg cctgacccat gtctctacag cggtcgtggg aactcttggg     780
tatgcagctc cggagtacat gcagaccgga cgcctcactg ccaagagtga catatggggc     840
tatggtgtgc tcctttatga gctcatcacc ggccgccgtc ccattgaccg gaaccgccca     900
```

```
aagggtgagc agaagctcct ggattgggtg aaaccataca tatctgatat caagcggttc    960
cccatcatca tagacccacg gctagagggg cactacaacc tcaagtccat gacaaagctg   1020
gctagtgtgg cgaaccgctg tctcgtccgg ctaccaaagt cgcgcccaaa gatgagtgag   1080
gtgtatgaga tggttcagaa gattgtggcc agcattgaga ccggcacacc acagcctcct   1140
ctgcactacc atgggtcggt ttctgaaccg ggctcaaagc ggccaaagaa ggggtcactg   1200
aagagaaggt tccaagaatt caaattcggt tgccggcaga ttgtatggcg gagctggaag   1260
cctgagatca taaagacttg ctga                                          1284
```

<210> SEQ ID NO 48
<211> LENGTH: 428
<212> TYPE: PRT
<213> ORGANISM: oryza sativa

<400> SEQUENCE: 48

```
Met Met Arg Cys Leu Pro Phe Leu His Gly Asp Ser Lys Glu Glu Asp
1               5                   10                  15

Pro Val Asn Lys Ser Ala Ser Val Arg Ser Leu Ser Thr Thr Ser Thr
            20                  25                  30

Glu Arg Asp Val Arg Ser Gly Ser Asp Phe Asn Ser Leu Asn Val Ser
        35                  40                  45

Asp Met Ser Ala Glu Ser Ile Arg Arg Thr Gln Tyr Pro Ser Phe Thr
50                  55                  60

Asp Arg Pro Ser Asn Leu Arg Val Phe Ser Phe Ser Glu Leu Lys Asn
65                  70                  75                  80

Ala Thr Arg Asn Phe Ser Arg Ser Leu Met Val Gly Glu Gly Gly Phe
                85                  90                  95

Gly Cys Val Tyr Arg Gly Val Ile Lys Asn Ser Asp Glu Pro Thr Glu
            100                 105                 110

Arg Thr Glu Ile Ala Val Lys Gln Leu Asn Arg Lys Gly Leu Gln Gly
        115                 120                 125

Gln Lys Glu Trp Leu Thr Glu Leu Asn Val Leu Gly Ile Val Glu His
130                 135                 140

Pro Asn Leu Val Lys Leu Ile Gly Tyr Cys Ala Glu Asp Asp Glu Arg
145                 150                 155                 160

Gly Val Gln Arg Leu Leu Val Tyr Glu Tyr Met Pro Asn Gly Ser Val
                165                 170                 175

Asp Asp His Leu Ser Ser Arg Ser Asn Ser Thr Leu Ser Trp Pro Met
            180                 185                 190

Arg Leu Lys Val Ala Leu Asp Ala Ala Arg Gly Leu Lys Tyr Leu His
        195                 200                 205

Glu Glu Met Glu Phe Gln Val Ile Phe Arg Asp Leu Lys Thr Ser Asn
210                 215                 220

Ile Leu Leu Asp Glu Asn Trp Asn Ala Lys Leu Ser Asp Phe Gly Leu
225                 230                 235                 240

Ala Arg His Gly Pro Ser Glu Gly Leu Thr His Val Ser Thr Ala Val
                245                 250                 255

Val Gly Thr Leu Gly Tyr Ala Ala Pro Glu Tyr Met Gln Thr Gly Arg
            260                 265                 270

Leu Thr Ala Lys Ser Asp Ile Trp Gly Tyr Gly Val Leu Leu Tyr Glu
        275                 280                 285

Leu Ile Thr Gly Arg Arg Pro Ile Asp Arg Asn Arg Pro Lys Gly Glu
290                 295                 300
```

Gln Lys Leu Leu Asp Trp Val Lys Pro Tyr Ile Ser Asp Ile Lys Arg
305                 310                 315                 320

Phe Pro Ile Ile Ile Asp Pro Arg Leu Glu Gly His Tyr Asn Leu Lys
                325                 330                 335

Ser Met Thr Lys Leu Ala Ser Val Ala Asn Arg Cys Leu Val Arg Leu
            340                 345                 350

Pro Lys Ser Arg Pro Lys Met Ser Glu Val Tyr Glu Met Val Gln Lys
        355                 360                 365

Ile Val Ala Ser Ile Glu Thr Gly Thr Pro Gln Pro Leu His Tyr
370                 375                 380

His Gly Ser Val Ser Glu Pro Gly Ser Lys Arg Pro Lys Lys Gly Ser
385                 390                 395                 400

Leu Lys Arg Arg Phe Gln Glu Phe Lys Phe Gly Cys Arg Gln Ile Val
                405                 410                 415

Trp Arg Ser Trp Lys Pro Glu Ile Ile Lys Thr Cys
            420                 425

<210> SEQ ID NO 49
<211> LENGTH: 1041
<212> TYPE: DNA
<213> ORGANISM: Gossypium hirsutum

<400> SEQUENCE: 49

```
acagtttctg agcttaaatc tgcaaccaag aactttagcc gctctttcat gctcggagag      60
ggtggatttg gctgtgttta caagggttct ctcaagagtc ctgaagatcc gtctgaaaag     120
attgaagtag cagtgaaaca gcttggtaaa aggggttgc agggccacaa ggagtgggtg     180
actgaagtaa atgtccttgg tgtggttgag catccgaatc ttgtgaagct agttggttac     240
tgtgctgaag acgatgaaag aggaatccaa cggcttttga tatatgaata tatgcctaat     300
agaagtgtgg aaaaccattt atctgtgcgg tcagaaacaa ctctttcctg gcaatgaga      360
ttgaaaatag cccaagatgc tgctcgtggg ttagcatacc tacatgaagg aatggagttc     420
cagatcatct tcagggattt taaatcatca aatatccttc tagatgagca atggaatgca     480
aagctctctg actttggatt agccaggttg ggcccttcag aaggattaac tcatatctca     540
acagcggttg ttgggacaat gggatatgcg gctcctgaat acatccagac aggacgttta     600
acatccaaga ttgatgtgtg gagctatggg gtcttcctct atgaactcat tactggcagg     660
cgccccttig acaaaaaccg tcccaagaat gagcaaaggc tattggaatg ggtaaagcca     720
tacctatctg ataggaaatt ccagttgata ttggacccta gactgaaagg gaaataccaa     780
ctcaagtctg ctcaaaggct tgcggttgtg gccaaccgat gcttagtcag aaacccaaag     840
tcacgcccta agatgagtga ggttttagaa atggtgaatc ggattgtgga agcatcatca     900
gcaggaccca gaactcctga accaccattg aatgatgtct ctctggaaac tgctagggaa     960
cgtaaaagaa ggattataga ttttagaagc ggtgaagagt ttgtttggtc atggactcca    1020
aagctcataa gaccatgcta a                                                1041
```

<210> SEQ ID NO 50
<211> LENGTH: 346
<212> TYPE: PRT
<213> ORGANISM: Gossypium hirsutum

<400> SEQUENCE: 50

Thr Val Ser Glu Leu Lys Ser Ala Thr Lys Asn Phe Arg Ser Phe
1               5                   10                  15

```
Met Leu Gly Glu Gly Gly Phe Gly Cys Val Tyr Lys Gly Ser Leu Lys
                20                  25                  30

Ser Pro Glu Asp Pro Ser Glu Lys Ile Glu Val Ala Val Lys Gln Leu
            35                  40                  45

Gly Lys Arg Gly Leu Gln Gly His Lys Glu Trp Val Thr Glu Val Asn
 50                  55                  60

Val Leu Gly Val Val Glu His Pro Asn Leu Val Lys Leu Val Gly Tyr
 65                  70                  75                  80

Cys Ala Glu Asp Asp Glu Arg Gly Ile Gln Arg Leu Leu Ile Tyr Glu
                85                  90                  95

Tyr Met Pro Asn Arg Ser Val Glu Asn His Leu Ser Val Arg Ser Glu
                100                 105                 110

Thr Thr Leu Ser Trp Ala Met Arg Leu Lys Ile Ala Gln Asp Ala Ala
            115                 120                 125

Arg Gly Leu Ala Tyr Leu His Glu Gly Met Glu Phe Gln Ile Ile Phe
130                 135                 140

Arg Asp Phe Lys Ser Ser Asn Ile Leu Leu Asp Glu Gln Trp Asn Ala
145                 150                 155                 160

Lys Leu Ser Asp Phe Gly Leu Ala Arg Leu Gly Pro Ser Glu Gly Leu
                165                 170                 175

Thr His Ile Ser Thr Ala Val Val Gly Thr Met Gly Tyr Ala Ala Pro
                180                 185                 190

Glu Tyr Ile Gln Thr Gly Arg Leu Thr Ser Lys Ile Asp Val Trp Ser
            195                 200                 205

Tyr Gly Val Phe Leu Tyr Glu Leu Ile Thr Gly Arg Arg Pro Phe Asp
210                 215                 220

Lys Asn Arg Pro Lys Asn Glu Gln Arg Leu Leu Glu Trp Val Lys Pro
225                 230                 235                 240

Tyr Leu Ser Asp Arg Lys Phe Gln Leu Ile Leu Asp Pro Arg Leu Lys
                245                 250                 255

Gly Lys Tyr Gln Leu Lys Ser Ala Gln Arg Leu Ala Val Val Ala Asn
            260                 265                 270

Arg Cys Leu Val Arg Asn Pro Lys Ser Arg Pro Lys Met Ser Glu Val
275                 280                 285

Leu Glu Met Val Asn Arg Ile Val Glu Ala Ser Ser Ala Gly Pro Arg
290                 295                 300

Thr Pro Glu Pro Pro Leu Asn Asp Val Ser Leu Glu Thr Ala Arg Glu
305                 310                 315                 320

Arg Lys Arg Arg Ile Ile Asp Phe Arg Ser Gly Glu Glu Phe Val Trp
                325                 330                 335

Ser Trp Thr Pro Lys Leu Ile Arg Pro Cys
                340                 345
```

<210> SEQ ID NO 51
<211> LENGTH: 30
<212> TYPE: DNA
<213> ORGANISM: Artificial Sequence
<220> FEATURE:
<223> OTHER INFORMATION: NG6 Forward Primer

<400> SEQUENCE: 51
tcgagctagc atgaagcttg tggagaagac                                      30

<210> SEQ ID NO 52
<211> LENGTH: 29
<212> TYPE: DNA

```
<213> ORGANISM: Artificial Sequence
<220> FEATURE:
<223> OTHER INFORMATION: NG6 Reverse Primer

<400> SEQUENCE: 52
cgacgagctc ttacctgatg gaacaagag                                          29

<210> SEQ ID NO 53
<211> LENGTH: 22
<212> TYPE: DNA
<213> ORGANISM: Artificial Sequence
<220> FEATURE:
<223> OTHER INFORMATION: NG21 Forward Primer

<400> SEQUENCE: 53
atggtgagtg acaagcatgt ag                                                 22

<210> SEQ ID NO 54
<211> LENGTH: 20
<212> TYPE: DNA
<213> ORGANISM: Artificial Sequence
<220> FEATURE:
<223> OTHER INFORMATION: NG21 Reverse Primer

<400> SEQUENCE: 54
tcacttgccc gtgatgaatg                                                    20

<210> SEQ ID NO 55
<211> LENGTH: 21
<212> TYPE: DNA
<213> ORGANISM: Artificial Sequence
<220> FEATURE:
<223> OTHER INFORMATION: NG24 Forward Primer

<400> SEQUENCE: 55
atgggttatc tctcttgcaa c                                                  21

<210> SEQ ID NO 56
<211> LENGTH: 20
<212> TYPE: DNA
<213> ORGANISM: Artificial Sequence
<220> FEATURE:
<223> OTHER INFORMATION: NG24 Reverse Primer

<400> SEQUENCE: 56
tcagtatctc ttccgcgacg                                                    20

<210> SEQ ID NO 57
<211> LENGTH: 20
<212> TYPE: DNA
<213> ORGANISM: Artificial Sequence
<220> FEATURE:
<223> OTHER INFORMATION: NG28 Forward Primer

<400> SEQUENCE: 57
atgggcatgg aagctttgag                                                    20

<210> SEQ ID NO 58
<211> LENGTH: 20
<212> TYPE: DNA
<213> ORGANISM: Artificial Sequence
<220> FEATURE:
<223> OTHER INFORMATION: NG28 Reverse Primer

<400> SEQUENCE: 58
tcaaaatgga gtttcggcgt                                                    20
```

<210> SEQ ID NO 59
<211> LENGTH: 20
<212> TYPE: DNA
<213> ORGANISM: Artificial Sequence
<220> FEATURE:
<223> OTHER INFORMATION: NG32 Forward Primer

<400> SEQUENCE: 59
atgaaatgct tcttattccc     20

<210> SEQ ID NO 60
<211> LENGTH: 20
<212> TYPE: DNA
<213> ORGANISM: Artificial Sequence
<220> FEATURE:
<223> OTHER INFORMATION: NG32 Reverse Primer

<400> SEQUENCE: 60
tcaacaagct ctcacattct     20

<210> SEQ ID NO 61
<211> LENGTH: 18
<212> TYPE: DNA
<213> ORGANISM: Artificial Sequence
<220> FEATURE:
<223> OTHER INFORMATION: NG6 Forward Primer

<400> SEQUENCE: 61
tgtgcccgga gccctacc     18

<210> SEQ ID NO 62
<211> LENGTH: 22
<212> TYPE: DNA
<213> ORGANISM: Artificial Sequence
<220> FEATURE:
<223> OTHER INFORMATION: NG6 Reverse Primer

<400> SEQUENCE: 62
ctttcagtgc catgcggatt tt     22

<210> SEQ ID NO 63
<211> LENGTH: 21
<212> TYPE: DNA
<213> ORGANISM: Artificial Sequence
<220> FEATURE:
<223> OTHER INFORMATION: NG21 Forward Primer

<400> SEQUENCE: 63
ggcacaagtc ccgtcatcac c     21

<210> SEQ ID NO 64
<211> LENGTH: 22
<212> TYPE: DNA
<213> ORGANISM: Artificial Sequence
<220> FEATURE:
<223> OTHER INFORMATION: NG21 Reverse Primer

<400> SEQUENCE: 64
tccccaatcc cttcttttcc ta     22

<210> SEQ ID NO 65
<211> LENGTH: 20
<212> TYPE: DNA
<213> ORGANISM: Artificial Sequence
<220> FEATURE:

```
<223> OTHER INFORMATION: NG24 Forward Primer

<400> SEQUENCE: 65
gccgccgtca agagaacaac                                                  20

<210> SEQ ID NO 66
<211> LENGTH: 21
<212> TYPE: DNA
<213> ORGANISM: Artificial Sequence
<220> FEATURE:
<223> OTHER INFORMATION: NG24 Reverse Primer

<400> SEQUENCE: 66
ctccggtggt caacgcagta a                                                21

<210> SEQ ID NO 67
<211> LENGTH: 22
<212> TYPE: DNA
<213> ORGANISM: Artificial Sequence
<220> FEATURE:
<223> OTHER INFORMATION: NG28 Forward Primer

<400> SEQUENCE: 67
tgttgttgtg gcctcgttgt ta                                               22

<210> SEQ ID NO 68
<211> LENGTH: 22
<212> TYPE: DNA
<213> ORGANISM: Artificial Sequence
<220> FEATURE:
<223> OTHER INFORMATION: NG28 Reverse Primer

<400> SEQUENCE: 68
ctttccttca ccgccttctt tc                                               22

<210> SEQ ID NO 69
<211> LENGTH: 21
<212> TYPE: DNA
<213> ORGANISM: Artificial Sequence
<220> FEATURE:
<223> OTHER INFORMATION: NG32 Forward Primer

<400> SEQUENCE: 69
aagctttcgg atttcggttt g                                                21

<210> SEQ ID NO 70
<211> LENGTH: 22
<212> TYPE: DNA
<213> ORGANISM: Artificial Sequence
<220> FEATURE:
<223> OTHER INFORMATION: NG32 Reverse Primer

<400> SEQUENCE: 70
tggccttctt cctgtaatga gc                                               22

<210> SEQ ID NO 71
<211> LENGTH: 17
<212> TYPE: DNA
<213> ORGANISM: Artificial Sequence
<220> FEATURE:
<223> OTHER INFORMATION: ACTIN Forward Primer

<400> SEQUENCE: 71
cccgctatgt atgtcgc                                                     17
```

<210> SEQ ID NO 72
<211> LENGTH: 18
<212> TYPE: DNA
<213> ORGANISM: Artificial Sequence
<220> FEATURE:
<223> OTHER INFORMATION: ACTIN Reverse Primer

<400> SEQUENCE: 72
aaggtcaaga cggaggat                                                    18

<210> SEQ ID NO 73
<211> LENGTH: 1971
<212> TYPE: DNA
<213> ORGANISM: Arabidopsis thaliana

<400> SEQUENCE: 73

```
atgatcgtta atttctcttt cttcctcctt ctcttcgtct ccgtcttcgt ttcctctgct      60
gattctaaag cgaccatttc aatttcccct aatgctctca atcgatctgg cgattccgtt     120
gtgatacaat ggtccggtgt cgattctccg tcagatctcg attggttagg actctactcg     180
ccgccggagt ctcctaatga tcactttatt ggttacaaat tcctcaatga atcgtccact     240
tggaaagatg gtttcggttc gatttctctt cctttaacca atctccgatc aaattacaca     300
ttccggatct tccgttggag cgaatccgag attgatccga acataagga tcatgatcag     360
aatcctttac caggaactaa acatcttcta gctgaatcgg agcagctgac tttcggatcc     420
ggtgttggta tgccggagca gatccatttg tcgttcacaa atatggttaa cacgatgcgt     480
gttatgtttg tagctggaga tggtgaagaa cgttttgtta gatacggtga atcgaaggat     540
ttgttaggta attccgcggc ggcgcgtggg atgaggtacg agagagagca catgtgtgat     600
tcgccggcga attccactat tggttggaga gatcctggtt ggattttga taccgtcatg     660
aagaatttga atgatggcgt tagatactat tatcaggttg ggagtgattc taagggatgg     720
agtgagatcc atagctacat tgctcgagat gtgactgcag aagaaaccgt agctttcatg     780
tttggagata tgggttgtgc tacaccatac acgacattta tccgcacaca agatgagagc     840
atatctacag tgaagtggat cctccgtgac attgaagctc ttggtgataa gccagctatg     900
atttcacaca ttggagatat aagttatgct cgtggttact cgtgggtatg ggatgagttc     960
tttgctcagg ttgagcctat tgcctcgaca gttccttacc atgtttgcat tggtaaccat    1020
gagtatgatt tctctactca gccgtggaaa cctgattggg cagcttctat ttatggaaac    1080
gatggtggtg cgaatgtgg tgtgccgtat agcttgaagt taacatgcc tgggaattct    1140
tcagagtcta caggaatgaa agctcctccg acaaggaatt tatattattc ttatgatatg    1200
ggaacggtcc atttcgttta tatctccaca gagacgaatt ttcttaaagg aggtagtcaa    1260
tatgaattca taaagcgaga tctagagtct gtagacagga agaaaacacc gtttgttgtt    1320
gtgcaaggac atagaccaat gtacactacg agcaacgagg ttagagacac tatgattcga    1380
caaaagatgg ttgagcatct agaacctttg tttgtgaaaa acaatgtcac acttgctcta    1440
tggggacatg ttcatagata cgaaaggttt tgtcccataa gcaacaacac ttgcggcaca    1500
cagtggcaag gaaatccggt tcatcttgtg atcggtatgg ctggtcaaga ttggcaaccg    1560
atttggcagc ctagaccaaa ccatccagat cttcctatat tccctcagcc tgaacaatca    1620
atgtatcgta caggtgagtt tggttacact cgtttagttg caaacaaaga aaagctcact    1680
gttttcttttg tgggtaatca cgatggcgaa gttcatgata ctgttgagat gttagcatct    1740
ggggtagtaa tcagtgggag caaagagagt actaaaatcc caaatctgaa aaccgttcct    1800
```

```
gcttctgcta cacttatggg aaaatcagaa tctaatgctt tgtggtatgc caaaggagca    1860
ggcttgatgg ttgtgggtgt gcttttaggg ttcattatcg gttttttac ccggggaaag      1920 aaatcttcgt ctggaaaccg ttggatccca gtcaagaacg aggagacata a              1971
```

<210> SEQ ID NO 74
<211> LENGTH: 656
<212> TYPE: PRT
<213> ORGANISM: Arabidopsis thaliana

<400> SEQUENCE: 74

| | | | | | | | | | | | | | | |
|---|---|---|---|---|---|---|---|---|---|---|---|---|---|---|
| Met | Ile | Val | Asn | Phe | Ser | Phe | Phe | Leu | Leu | Leu | Phe | Val | Ser | Phe |
| 1 | | | | 5 | | | | | 10 | | | | | 15 |
| Val | Ser | Ser | Ala | Asp | Ser | Lys | Ala | Thr | Ile | Ser | Ile | Ser | Pro | Asn | Ala |
| | | 20 | | | | | 25 | | | | | 30 | | |
| Leu | Asn | Arg | Ser | Gly | Asp | Ser | Val | Val | Ile | Gln | Trp | Ser | Gly | Val | Asp |
| | | | 35 | | | | | 40 | | | | | 45 | | |
| Ser | Pro | Ser | Asp | Leu | Asp | Trp | Leu | Gly | Leu | Tyr | Ser | Pro | Pro | Glu | Ser |
| | 50 | | | | | 55 | | | | | 60 | | | | |
| Pro | Asn | Asp | His | Phe | Ile | Gly | Tyr | Lys | Phe | Leu | Asn | Glu | Ser | Ser | Thr |
| 65 | | | | | 70 | | | | | 75 | | | | | 80 |
| Trp | Lys | Asp | Gly | Phe | Gly | Ser | Ile | Ser | Leu | Pro | Leu | Thr | Asn | Leu | Arg |
| | | | | 85 | | | | | 90 | | | | | 95 | |
| Ser | Asn | Tyr | Thr | Phe | Arg | Ile | Phe | Arg | Trp | Ser | Glu | Ser | Glu | Ile | Asp |
| | | | 100 | | | | | 105 | | | | | 110 | | |
| Pro | Lys | His | Lys | Asp | His | Asp | Gln | Asn | Pro | Leu | Pro | Gly | Thr | Lys | His |
| | | 115 | | | | | 120 | | | | | 125 | | | |
| Leu | Leu | Ala | Glu | Ser | Glu | Gln | Leu | Thr | Phe | Gly | Ser | Gly | Val | Gly | Met |
| | 130 | | | | | 135 | | | | | 140 | | | | |
| Pro | Glu | Gln | Ile | His | Leu | Ser | Phe | Thr | Asn | Met | Val | Asn | Thr | Met | Arg |
| 145 | | | | | 150 | | | | | 155 | | | | | 160 |
| Val | Met | Phe | Val | Ala | Gly | Asp | Gly | Glu | Glu | Arg | Phe | Val | Arg | Tyr | Gly |
| | | | | 165 | | | | | 170 | | | | | 175 | |
| Glu | Ser | Lys | Asp | Leu | Leu | Gly | Asn | Ser | Ala | Ala | Ala | Arg | Gly | Met | Arg |
| | | | 180 | | | | | 185 | | | | | 190 | | |
| Tyr | Glu | Arg | Glu | His | Met | Cys | Asp | Ser | Pro | Ala | Asn | Ser | Thr | Ile | Gly |
| | | 195 | | | | | 200 | | | | | 205 | | | |
| Trp | Arg | Asp | Pro | Gly | Trp | Ile | Phe | Asp | Thr | Val | Met | Lys | Asn | Leu | Asn |
| | 210 | | | | | 215 | | | | | 220 | | | | |
| Asp | Gly | Val | Arg | Tyr | Tyr | Tyr | Gln | Val | Gly | Ser | Asp | Ser | Lys | Gly | Trp |
| 225 | | | | | 230 | | | | | 235 | | | | | 240 |
| Ser | Glu | Ile | His | Ser | Tyr | Ile | Ala | Arg | Asp | Val | Thr | Ala | Glu | Glu | Thr |
| | | | | 245 | | | | | 250 | | | | | 255 | |
| Val | Ala | Phe | Met | Phe | Gly | Asp | Met | Gly | Cys | Ala | Thr | Pro | Tyr | Thr | Thr |
| | | | 260 | | | | | 265 | | | | | 270 | | |
| Phe | Ile | Arg | Thr | Gln | Asp | Glu | Ser | Ile | Ser | Thr | Val | Lys | Trp | Ile | Leu |
| | | 275 | | | | | 280 | | | | | 285 | | | |
| Arg | Asp | Ile | Glu | Ala | Leu | Gly | Asp | Lys | Pro | Ala | Met | Ile | Ser | His | Ile |
| | 290 | | | | | 295 | | | | | 300 | | | | |
| Gly | Asp | Ile | Ser | Tyr | Ala | Arg | Gly | Tyr | Ser | Trp | Val | Trp | Asp | Glu | Phe |
| 305 | | | | | 310 | | | | | 315 | | | | | 320 |
| Phe | Ala | Gln | Val | Glu | Pro | Ile | Ala | Ser | Thr | Val | Pro | Tyr | His | Val | Cys |
| | | | | 325 | | | | | 330 | | | | | 335 | |
| Ile | Gly | Asn | His | Glu | Tyr | Asp | Phe | Ser | Thr | Gln | Pro | Trp | Lys | Pro | Asp |
| | | | 340 | | | | | 345 | | | | | 350 | | |

```
Trp Ala Ala Ser Ile Tyr Gly Asn Asp Gly Gly Glu Cys Gly Val
        355                 360                 365

Pro Tyr Ser Leu Lys Phe Asn Met Pro Gly Asn Ser Ser Glu Ser Thr
    370                 375                 380

Gly Met Lys Ala Pro Pro Thr Arg Asn Leu Tyr Tyr Ser Tyr Asp Met
385                 390                 395                 400

Gly Thr Val His Phe Val Tyr Ile Ser Thr Glu Thr Asn Phe Leu Lys
                405                 410                 415

Gly Gly Ser Gln Tyr Glu Phe Ile Lys Arg Asp Leu Glu Ser Val Asp
                420                 425                 430

Arg Lys Lys Thr Pro Phe Val Val Val Gln Gly His Arg Pro Met Tyr
            435                 440                 445

Thr Thr Ser Asn Glu Val Arg Asp Thr Met Ile Arg Gln Lys Met Val
        450                 455                 460

Glu His Leu Glu Pro Leu Phe Val Lys Asn Asn Val Thr Leu Ala Leu
465                 470                 475                 480

Trp Gly His Val His Arg Tyr Glu Arg Phe Cys Pro Ile Ser Asn Asn
                485                 490                 495

Thr Cys Gly Thr Gln Trp Gln Gly Asn Pro Val His Leu Val Ile Gly
            500                 505                 510

Met Ala Gly Gln Asp Trp Gln Pro Ile Trp Gln Pro Arg Pro Asn His
        515                 520                 525

Pro Asp Leu Pro Ile Phe Pro Gln Pro Glu Gln Ser Met Tyr Arg Thr
    530                 535                 540

Gly Glu Phe Gly Tyr Thr Arg Leu Val Ala Asn Lys Glu Lys Leu Thr
545                 550                 555                 560

Val Ser Phe Val Gly Asn His Asp Gly Glu Val His Asp Thr Val Glu
                565                 570                 575

Met Leu Ala Ser Gly Val Val Ile Ser Gly Ser Lys Glu Ser Thr Lys
                580                 585                 590

Ile Pro Asn Leu Lys Thr Val Pro Ala Ser Ala Thr Leu Met Gly Lys
            595                 600                 605

Ser Glu Ser Asn Ala Leu Trp Tyr Ala Lys Gly Ala Gly Leu Met Val
        610                 615                 620

Val Gly Val Leu Leu Gly Phe Ile Ile Gly Phe Phe Thr Arg Gly Lys
625                 630                 635                 640

Lys Ser Ser Ser Gly Asn Arg Trp Ile Pro Val Lys Asn Glu Glu Thr
                645                 650                 655

<210> SEQ ID NO 75
<211> LENGTH: 8
<212> TYPE: PRT
<213> ORGANISM: Artificial sequence
<220> FEATURE:
<223> OTHER INFORMATION: motifs

<400> SEQUENCE: 75

Gly Ile Phe Arg Ser Gly Phe Pro
1               5

<210> SEQ ID NO 76
<211> LENGTH: 8
<212> TYPE: PRT
<213> ORGANISM: Artificial sequence
<220> FEATURE:
<223> OTHER INFORMATION: motifs
```

```
<400> SEQUENCE: 76

Tyr Leu Cys Pro Glu Pro Tyr Pro
1               5

<210> SEQ ID NO 77
<211> LENGTH: 8
<212> TYPE: PRT
<213> ORGANISM: Artificial sequence
<220> FEATURE:
<223> OTHER INFORMATION: motifs
<220> FEATURE:
<221> NAME/KEY: misc_feature
<222> LOCATION: (6)..(6)
<223> OTHER INFORMATION: Xaa can be any naturally occurring amino acid

<400> SEQUENCE: 77

Lys Glu Pro Phe Val Xaa Ile Pro
1               5

<210> SEQ ID NO 78
<211> LENGTH: 10
<212> TYPE: PRT
<213> ORGANISM: Artificial sequence
<220> FEATURE:
<223> OTHER INFORMATION: motifs
<220> FEATURE:
<221> NAME/KEY: misc_feature
<222> LOCATION: (3)..(3)
<223> OTHER INFORMATION: Xaa can be any naturally occurring amino acid

<400> SEQUENCE: 78

His Cys Xaa Arg Gly Lys His Arg Thr Gly
1               5                   10

<210> SEQ ID NO 79
<211> LENGTH: 10
<212> TYPE: PRT
<213> ORGANISM: Artificial sequence
<220> FEATURE:
<223> OTHER INFORMATION: NG21 motif
<220> FEATURE:
<221> NAME/KEY: MISC_FEATURE
<222> LOCATION: (7)..(7)
<223> OTHER INFORMATION: Xaa = Asp or Glu

<400> SEQUENCE: 79

Asp Asn Trp Asp Asp Ala Xaa Gly Tyr Tyr
1               5                   10

<210> SEQ ID NO 80
<211> LENGTH: 12
<212> TYPE: PRT
<213> ORGANISM: Artificial sequence
<220> FEATURE:
<223> OTHER INFORMATION: NG21 motif

<400> SEQUENCE: 80

Tyr Arg Asn His Leu Cys Leu Val Phe Glu Ser Leu
1               5                   10

<210> SEQ ID NO 81
<211> LENGTH: 15
<212> TYPE: PRT
<213> ORGANISM: Artificial sequence
<220> FEATURE:
<223> OTHER INFORMATION: NG21 motif

<400> SEQUENCE: 81
```

```
Val Leu His Cys Asp Ile Lys Pro Asp Asn Met Leu Val Asn Glu
1               5                   10                  15
```

<210> SEQ ID NO 82
<211> LENGTH: 14
<212> TYPE: PRT
<213> ORGANISM: Artificial sequence
<220> FEATURE:
<223> OTHER INFORMATION: NG21 motif
<220> FEATURE:
<221> NAME/KEY: MISC_FEATURE
<222> LOCATION: (8)..(8)
<223> OTHER INFORMATION: Xaa = Phe or Val
<220> FEATURE:
<221> NAME/KEY: misc_feature
<222> LOCATION: (11)..(11)
<223> OTHER INFORMATION: Xaa can be any naturally occurring amino acid

<400> SEQUENCE: 82

```
Thr Pro Tyr Leu Val Ser Arg Phe Tyr Arg Xaa Pro Glu Ile
1               5                   10
```

<210> SEQ ID NO 83
<211> LENGTH: 8
<212> TYPE: PRT
<213> ORGANISM: Artificial sequence
<220> FEATURE:
<223> OTHER INFORMATION: NG24 motif
<220> FEATURE:
<221> NAME/KEY: misc_feature
<222> LOCATION: (6)..(6)
<223> OTHER INFORMATION: Xaa can be any naturally occurring amino acid

<400> SEQUENCE: 83

```
Val Arg His Arg Asp Xaa Lys Ser
1               5
```

<210> SEQ ID NO 84
<211> LENGTH: 9
<212> TYPE: PRT
<213> ORGANISM: Artificial sequence
<220> FEATURE:
<223> OTHER INFORMATION: NG24 motif
<220> FEATURE:
<221> NAME/KEY: misc_feature
<222> LOCATION: (4)..(4)
<223> OTHER INFORMATION: Xaa can be any naturally occurring amino acid

<400> SEQUENCE: 84

```
Gly Thr Leu Xaa Gly Tyr Leu Asp Pro
1               5
```

<210> SEQ ID NO 85
<211> LENGTH: 12
<212> TYPE: PRT
<213> ORGANISM: Artificial Sequence
<220> FEATURE:
<223> OTHER INFORMATION: NG24 motif
<220> FEATURE:
<221> NAME/KEY: MISC_FEATURE
<222> LOCATION: (3)..(3)
<223> OTHER INFORMATION: Xaa = Phe or Tyr
<220> FEATURE:
<221> NAME/KEY: MISC_FEATURE
<222> LOCATION: (5)..(5)
<223> OTHER INFORMATION: Xaa = Phe or Tyr
<220> FEATURE:
<221> NAME/KEY: MISC_FEATURE
<222> LOCATION: (7)..(7)
<223> OTHER INFORMATION: Xaa = Ile or Val

<400> SEQUENCE: 85

```
Asp Val Xaa Ser Xaa Gly Xaa Leu Leu Leu Glu Ile
1               5                   10
```

<210> SEQ ID NO 86
<211> LENGTH: 8
<212> TYPE: PRT
<213> ORGANISM: Artificial sequence
<220> FEATURE:
<223> OTHER INFORMATION: NG28 motif

<400> SEQUENCE: 86

```
Arg Arg His Lys Ile Ala Leu Gly
1               5
```

<210> SEQ ID NO 87
<211> LENGTH: 6
<212> TYPE: PRT
<213> ORGANISM: Artificial sequence
<220> FEATURE:
<223> OTHER INFORMATION: NG28 motif
<220> FEATURE:
<221> NAME/KEY: MISC_FEATURE
<222> LOCATION: (2)..(2)
<223> OTHER INFORMATION: Xaa = Lys or Arg

<400> SEQUENCE: 87

```
Tyr Xaa Ala Pro Glu Leu
1               5
```

<210> SEQ ID NO 88
<211> LENGTH: 11
<212> TYPE: PRT
<213> ORGANISM: Artificial sequence
<220> FEATURE:
<223> OTHER INFORMATION: NG28 motif

<400> SEQUENCE: 88

```
Asp Val Tyr Ala Phe Gly Ile Leu Leu Leu Glu
1               5                   10
```

<210> SEQ ID NO 89
<211> LENGTH: 8
<212> TYPE: PRT
<213> ORGANISM: Artificial sequence
<220> FEATURE:
<223> OTHER INFORMATION: NG32 motif
<220> FEATURE:
<221> NAME/KEY: misc_feature
<222> LOCATION: (3)..(3)
<223> OTHER INFORMATION: Xaa can be any naturally occurring amino acid

<400> SEQUENCE: 89

```
Cys Ala Xaa Asp Asp Glu Arg Gly
1               5
```

<210> SEQ ID NO 90
<211> LENGTH: 10
<212> TYPE: PRT
<213> ORGANISM: Artificial sequence
<220> FEATURE:
<223> OTHER INFORMATION: NG32 motif

<400> SEQUENCE: 90

```
Ala Lys Leu Ser Asp Phe Gly Leu Ala Arg
1               5                   10
```

<210> SEQ ID NO 91

```
<211> LENGTH: 8
<212> TYPE: PRT
<213> ORGANISM: Artificial Sequence
<220> FEATURE:
<223> OTHER INFORMATION: NG32 motif
<220> FEATURE:
<221> NAME/KEY: MISC_FEATURE
<222> LOCATION: (8)..(8)
<223> OTHER INFORMATION: Xaa = Arg or Lys

<400> SEQUENCE: 91

Tyr Glu Leu Ile Thr Gly Arg Xaa
1               5

<210> SEQ ID NO 92
<211> LENGTH: 7
<212> TYPE: PRT
<213> ORGANISM: Artificial sequence
<220> FEATURE:
<223> OTHER INFORMATION: NG32 motif

<400> SEQUENCE: 92

Arg Pro Lys Met Ser Glu Val
1               5

<210> SEQ ID NO 93
<211> LENGTH: 648
<212> TYPE: DNA
<213> ORGANISM: Brassica napus

<400> SEQUENCE: 93
atgaagctag ttgagaatac gccggcggcg actgacaagt tcaccaccac ggaggaggag      60
gacggtgaag acgcctgccg cacgatcgag gtcgtcgaga aaacgtgtt tcaggctcag     120
ttcgatgaag ctgctgatgc ggttgaggag cttaacctta taccgccgct caacttctct     180
atggtggata acggaatatt ccgttctgga ttccctgatc cggctaactt ctccttcctc     240
cagactctcg gactccgctc aattatttat ctgtgtccgg agccttaccc agagagtaac     300
atccagttcc tcaaatccaa tgggattact cttttccagt ttggcattga aggcaataag     360
gaaccatttg tgattattcc agaccagaaa atccgcaagg cactcaatgt ccttttagat     420
gagaaaaacc atccggttct gattcattgt aagcgaggca agcatcgtac tggttgtctt     480
gtgggttgct tgagaaaact tcagaaatgg tgtttgactt cgatatttga cgagtaccag     540
cgatttgcag cagctaaagc tagagtttca gatcaaagat tcatggagat attcgacgtc     600
tccagcttca gtcatgttcc gatgtctttc tcttgttcca gcaggtaa                 648

<210> SEQ ID NO 94
<211> LENGTH: 215
<212> TYPE: PRT
<213> ORGANISM: Brassica napus

<400> SEQUENCE: 94

Met Lys Leu Val Glu Asn Thr Pro Ala Ala Thr Asp Lys Phe Thr Thr
1               5                   10                  15

Thr Glu Glu Glu Asp Gly Glu Asp Ala Cys Arg Thr Ile Glu Val Val
            20                  25                  30

Glu Arg Asn Val Phe Gln Ala Gln Phe Asp Glu Ala Ala Asp Ala Val
        35                  40                  45

Glu Glu Leu Asn Leu Ile Pro Pro Leu Asn Phe Ser Met Val Asp Asn
    50                  55                  60

Gly Ile Phe Arg Ser Gly Phe Pro Asp Pro Ala Asn Phe Ser Phe Leu
```

```
              65                  70                  75                  80
Gln Thr Leu Gly Leu Arg Ser Ile Ile Tyr Leu Cys Pro Glu Pro Tyr
                    85                  90                  95

Pro Glu Ser Asn Ile Gln Phe Leu Lys Ser Asn Gly Ile Thr Leu Phe
                100                 105                 110

Gln Phe Gly Ile Glu Gly Asn Lys Glu Pro Phe Val Ile Ile Pro Asp
                115                 120                 125

Gln Lys Ile Arg Lys Ala Leu Asn Val Leu Leu Asp Glu Lys Asn His
            130                 135                 140

Pro Val Leu Ile His Cys Lys Arg Gly Lys His Arg Thr Gly Cys Leu
145                 150                 155                 160

Val Gly Cys Leu Arg Lys Leu Gln Lys Trp Cys Leu Thr Ser Ile Phe
                165                 170                 175

Asp Glu Tyr Gln Arg Phe Ala Ala Ala Lys Ala Arg Val Ser Asp Gln
                180                 185                 190

Arg Phe Met Glu Ile Phe Asp Val Ser Ser Phe Ser His Val Pro Met
            195                 200                 205

Ser Phe Ser Cys Ser Ser Arg
    210                 215

<210> SEQ ID NO 95
<211> LENGTH: 2325
<212> TYPE: DNA
<213> ORGANISM: Brassica napus

<400> SEQUENCE: 95
gtggtgtccg gtgcattccc ggcggccctt gaaaatccgg aggacaagaa agaatctggg      60
ggtccttcgg agagagttgg taaaagaagt tatgataatg caggagttc gttttcttcg     120 gagaactctg aagagaagta taagagtagt aaccggtctc ttacggagag ccggcagtat     180
aacgaagtcc gtgcgcggag tagatctaag tcaagggttg ttgcggagga tgagttttcg     240
gtcagaggaa gacatcgcga ctctagtagg gagtatcgtc atgacagagt tgactcaagg     300
aggagcgagg gacgtgggcg atatgaagga tatgacaggg aatatactcg agaagacgtg     360
gaaagagaaa gaagtaagga gagggatatg gacaggaag gaagcattcg agataggat      420 tcagaaggaa gtaaacggag agagagggat attgatcgga ggagggaaag agaacgagaa     480
gaaaggaggg agatagaggc tgaccgtgaa aggcggaaag ataaggaacg ggagcgcagc     540
attgataggg ataggagaag ggagagggaa ggacgagata gagacaatga agaggtggg      600 agcgtcgata gggaaaggag aagggagagg gaaggagatt atttacgaga cagagacaat     660
agaaggggta ggagtagaga cagaaccaga tatgatagcc gagagaggat gagagaaaag     720
gaaagggaga gtgacaaaga tagagaaatc caggctgata aggagaagca taaaagtgtt     780
gaagtggaca acgtgaaag gtcgaaatat gagaatgatc aagatgataa tgacaaagaa     840
tttatatgga aatctccgga agaaatagaa gaagaagaat taaataaaat cagggagagc     900
atagagaaat ttaaaagaa gcccgagcag caaagtgaac ttatttcgca ggataaggag     960
atagatttcg ttcaagaaag cagtgctcca gattcggctt cttttgcagt tgttacagat    1020
gctaatgctg tgcagccaa agctaagtcg acttcgacc ctgtagttag tgatgttgct     1080
aaaacctcat taacagctgg tgggccacct aatatgtttg gaatttcaaa ctcggagaaa    1140
actcaagctc cagcagggct tggcgaaggt agcccaaaga gtgaaagatc agctgacatg    1200
tttcatgatg atatattgg agagtcccca gctgctaatc aaaaagtgga tcacatgcga    1260
```

-continued

```
gggaaaggtg atggtgttcc aatggtaagg agcgggcttc atgacaattg ggatgatgcg    1320
gagggttatt acagctatca gttcggcgag ctaattgacg gcagatatga agtcattgct    1380
actcatggaa aaggcgtttt ctctactgtc gttcgtgcga agatttaag agctggacca     1440
gctgaacctg acgaagttgc tataaaaatt attcgtaaca acgagacgat gcataaagct    1500
ggccagactg aggttcagat attgaagaag ctggctggtg ctgaccgaga tgacaagcgg    1560
cactgtgttc gtttgctttc aagtttcaag taccggaatc accttttgctt ggtgtttgag   1620
tcgctccatt taaatcttcg agagctcttg aagaagtttg gccgtaacat tggcctcaaa    1680
ctgtctgctg ttaggtcgta ttcaaagcag cttttcattg cccttaaaca tctgaagaat    1740
tgtggggttc ttcactgcga tataaaacct gacaacatgc tggtgaatga aacaaaacc     1800
gtgttgaagc tttgcgactt tggtaatgca atgtttgctg gaaaaaacga agtcacgcca    1860
tatctcgtta gtcgctttta cagatcccct gaaatcattc tggggctggc ttatgaccat    1920
ccgcttgata tatggtcggt tggctgctgt ctatatgagc tttattgcgg gaaagttctt    1980
ttccctggcg ccacaaataa tgatatgtta cgccttcata tggaactgaa aggcctttc     2040
cccaaaaaga tgcttcgtaa gggagcattt attgatcagc actttgatca cgacttgaac    2100
ttttacgcta cagaggagga cactgttagt gggaagatga tgaagagaat gattttaaat    2160
gtaaagccaa aagattttgg ttcaattata aagggttacc ctggtgagga tcccaagatg    2220
ttagctcatt tcagggatct cttagacaag atgttcatcc ttgatccaga gaagagactg    2280
actgtgtcac aggcattagc tcacccattt atcactggca agtga                    2325

<210> SEQ ID NO 96
<211> LENGTH: 774
<212> TYPE: PRT
<213> ORGANISM: Brassica napus

<400> SEQUENCE: 96

Met Val Ser Gly Ala Phe Pro Ala Ala Leu Glu Asn Pro Glu Asp Lys
1               5                   10                  15

Lys Glu Ser Gly Gly Pro Ser Glu Arg Val Gly Lys Arg Ser Tyr Asp
            20                  25                  30

Asn Gly Arg Ser Ser Phe Ser Ser Glu Asn Ser Glu Glu Lys Tyr Lys
        35                  40                  45

Ser Ser Asn Arg Ser Leu Thr Glu Ser Arg Gln Tyr Asn Glu Val Arg
    50                  55                  60

Ala Arg Ser Arg Ser Lys Ser Arg Val Val Ala Glu Asp Glu Phe Ser
65                  70                  75                  80

Val Arg Gly Arg His Arg Asp Ser Ser Arg Glu Tyr Arg His Asp Arg
                85                  90                  95

Val Asp Ser Arg Arg Ser Glu Gly Arg Gly Arg Tyr Glu Gly Tyr Asp
            100                 105                 110

Arg Glu Tyr Thr Arg Glu Asp Val Glu Arg Glu Arg Ser Lys Glu Arg
        115                 120                 125

Asp Met Asp Arg Glu Gly Ser Ile Arg Asp Arg Asp Ser Glu Gly Ser
    130                 135                 140

Lys Arg Arg Glu Arg Asp Ile Asp Arg Arg Glu Arg Glu Arg Glu
145                 150                 155                 160

Glu Arg Arg Glu Ile Glu Ala Asp Arg Glu Arg Lys Asp Lys Glu
                165                 170                 175

Arg Glu Arg Ser Ile Asp Arg Asp Arg Arg Glu Arg Glu Gly Arg
            180                 185                 190
```

```
Asp Arg Asp Asn Glu Arg Gly Gly Ser Val Asp Arg Glu Arg Arg
        195                 200                 205

Glu Arg Glu Gly Asp Tyr Leu Arg Asp Arg Asp Asn Arg Arg Gly Arg
        210                 215                 220

Ser Arg Asp Arg Thr Arg Tyr Asp Ser Arg Glu Arg Met Arg Glu Lys
225                 230                 235                 240

Glu Arg Glu Ser Asp Lys Asp Arg Glu Ile Gln Ala Asp Lys Glu Lys
        245                 250                 255

His Lys Ser Val Glu Val Asp Asn Gly Glu Arg Ser Lys Tyr Glu Asn
            260                 265                 270

Asp Gln Asp Asp Asn Asp Lys Glu Phe Ile Trp Lys Ser Pro Glu Glu
        275                 280                 285

Ile Glu Glu Glu Glu Leu Asn Lys Ile Arg Glu Ser Ile Glu Lys Phe
    290                 295                 300

Lys Lys Lys Pro Glu Gln Gln Ser Glu Leu Ile Ser Gln Asp Lys Glu
305                 310                 315                 320

Ile Asp Phe Val Gln Glu Ser Ser Ala Pro Asp Ser Ala Ser Phe Ala
                325                 330                 335

Val Val Thr Asp Ala Asn Ala Gly Ala Ala Lys Ala Lys Ser Asp Phe
            340                 345                 350

Asp Pro Val Val Ser Asp Val Ala Lys Thr Ser Leu Thr Ala Gly Gly
        355                 360                 365

Pro Pro Asn Met Phe Gly Ile Ser Asn Ser Glu Lys Thr Gln Ala Pro
370                 375                 380

Ala Gly Leu Gly Glu Gly Ser Pro Lys Ser Glu Arg Ser Ala Asp Met
385                 390                 395                 400

Phe His Asp Asp Ile Phe Gly Glu Ser Pro Ala Ala Asn Gln Lys Val
                405                 410                 415

Asp His Met Arg Gly Lys Gly Asp Gly Val Pro Met Val Arg Ser Gly
            420                 425                 430

Leu His Asp Asn Trp Asp Asp Ala Glu Gly Tyr Tyr Ser Tyr Gln Phe
        435                 440                 445

Gly Glu Leu Ile Asp Gly Arg Tyr Glu Val Ile Ala Thr His Gly Lys
    450                 455                 460

Gly Val Phe Ser Thr Val Val Arg Ala Lys Asp Leu Arg Ala Gly Pro
465                 470                 475                 480

Ala Glu Pro Asp Glu Val Ala Ile Lys Ile Ile Arg Asn Asn Glu Thr
                485                 490                 495

Met His Lys Ala Gly Gln Thr Glu Val Gln Ile Leu Lys Lys Leu Ala
            500                 505                 510

Gly Ala Asp Arg Asp Asp Lys Arg His Cys Val Arg Leu Leu Ser Ser
        515                 520                 525

Phe Lys Tyr Arg Asn His Leu Cys Leu Val Phe Glu Ser Leu His Leu
    530                 535                 540

Asn Leu Arg Glu Leu Leu Lys Lys Phe Gly Arg Asn Ile Gly Leu Lys
545                 550                 555                 560

Leu Ser Ala Val Arg Ser Tyr Ser Lys Gln Leu Phe Ile Ala Leu Lys
                565                 570                 575

His Leu Lys Asn Cys Gly Val Leu His Cys Asp Ile Lys Pro Asp Asn
            580                 585                 590

Met Leu Val Asn Glu Asn Lys Thr Val Leu Lys Leu Cys Asp Phe Gly
        595                 600                 605
```

```
Asn Ala Met Phe Ala Gly Lys Asn Glu Val Thr Pro Tyr Leu Val Ser
    610                 615                 620
Arg Phe Tyr Arg Ser Pro Glu Ile Ile Leu Gly Leu Ala Tyr Asp His
625                 630                 635                 640
Pro Leu Asp Ile Trp Ser Val Gly Cys Cys Leu Tyr Glu Leu Tyr Cys
                645                 650                 655
Gly Lys Val Leu Phe Pro Gly Ala Thr Asn Asn Asp Met Leu Arg Leu
                660                 665                 670
His Met Glu Leu Lys Gly Leu Phe Pro Lys Lys Met Leu Arg Lys Gly
            675                 680                 685
Ala Phe Ile Asp Gln His Phe Asp His Asp Leu Asn Phe Tyr Ala Thr
    690                 695                 700
Glu Glu Asp Thr Val Ser Gly Lys Met Met Lys Arg Met Ile Leu Asn
705                 710                 715                 720
Val Lys Pro Lys Asp Phe Gly Ser Ile Ile Lys Gly Tyr Pro Gly Glu
                725                 730                 735
Asp Pro Lys Met Leu Ala His Phe Arg Asp Leu Leu Asp Lys Met Phe
                740                 745                 750
Ile Leu Asp Pro Glu Lys Arg Leu Thr Val Ser Gln Ala Leu Ala His
            755                 760                 765
Pro Phe Ile Thr Gly Lys
            770

<210> SEQ ID NO 97
<211> LENGTH: 1387
<212> TYPE: DNA
<213> ORGANISM: Brassica napus

<400> SEQUENCE: 97
atgcagctac ctattgcaac tgcagagatt ggctttgcgt tgcttctaac tgcagctgta      60
tcaatatcag cggttttata cgttcggtat aggctgaggc attgtaggtg ctcagagagt     120
gatgcaaggt cttctaaaga ctcagcgttt accaaagata cgaccgtcc ggatcttgat     180 aagttgcaga agcgcagaag ggctagagtg ttcacctacg aggagctgga gaaagctgca     240
gaagggttca agaagagtc aatagtaggg aaagggagct tctcatgtgt gtacaaaggt     300
gtgctgagag atggaaccac tgtcgctgtg aagaaggcca taatgtcatc agacaaacag     360
aagaactcaa acgagttccg caccgagctt gatctgttgt caagactcaa ccatgctcat     420
ctccttagcc ttcttggcta ctgcgaagaa ggaggagaga ggcttcttgt ttacgagttt     480
atggcgcatg gctcactcta caaccatctt cacggtaaga acaaggcctt gaagagcag     540 ctagattggg ttaaacgagt caccattgct gtccaagcag ctagaggaat cgagtacttg     600
catggctacg cttgtcctcc tgtcatccac cgtgatatca aatcatcaaa catacttata     660
gacgaagaac acaacgctag agtagctgac tttggtctct ccttgcttgg tcctgttgat     720
agcggctctc ctttagcaga gctgccagct ggcactctcg gttaccttga tcctgagtac     780
tatagactac actatctcac aaccaagtct gatgtctaca gcttcggagt cttgcttctc     840
gagatcctga gcggaagaaa agctattgac atgcactatg aagaagggaa catagtggaa     900
tgggcggttc ctttgatcaa agctggagat attacatcaa tcttggaccc ggtcttgaaa     960
caaccaaccg agatagaagc tctgaggagg atagtgagcg tggcttgcaa atgcgtgagg    1020
atgagaggca agacagacc gtcaatggat aaagtgacaa catcactgga gagagctctc    1080
gcgcagctga tggggaaccc gagcagcgag cagccgatat accgacaga agtggttctt    1140
```

```
gggagcagca ggatgcacaa gaagtcgtgg aggatcggtt cggagaacac tgagtttaga    1200
ggcgggtcgt ggataacttt ccctagcgtg acgtcatcac agaggaggaa gtcttcagct    1260
tctgaaggtg atgtggcgga ggaggtggag gatgaaggaa ggaagcaaca agaggcgttg    1320
aggagtcttg aagaggagat aggaccagct tctcctggac agagcttgtt cttgcatcat    1380
aatttct                                                              1387
```

<210> SEQ ID NO 98
<211> LENGTH: 462
<212> TYPE: PRT
<213> ORGANISM: Brassica napus

<400> SEQUENCE: 98

```
Met Gln Leu Pro Ile Ala Thr Ala Glu Ile Gly Phe Ala Leu Leu Leu
 1               5                  10                  15

Thr Ala Ala Val Ser Ile Ser Ala Val Leu Tyr Val Arg Tyr Arg Leu
            20                  25                  30

Arg His Cys Arg Cys Ser Glu Ser Asp Ala Arg Ser Ser Lys Asp Ser
        35                  40                  45

Ala Phe Thr Lys Asp Asn Asp Arg Pro Asp Leu Asp Lys Leu Gln Lys
    50                  55                  60

Arg Arg Arg Ala Arg Val Phe Thr Tyr Glu Glu Leu Glu Lys Ala Ala
65                  70                  75                  80

Glu Gly Phe Lys Glu Glu Ser Ile Val Gly Lys Gly Ser Phe Ser Cys
                85                  90                  95

Val Tyr Lys Gly Val Leu Arg Asp Gly Thr Thr Val Ala Val Lys Lys
            100                 105                 110

Ala Ile Met Ser Ser Asp Lys Gln Lys Asn Ser Asn Glu Phe Arg Thr
        115                 120                 125

Glu Leu Asp Leu Leu Ser Arg Leu Asn His Ala His Leu Leu Ser Leu
    130                 135                 140

Leu Gly Tyr Cys Glu Glu Gly Gly Glu Arg Leu Leu Val Tyr Glu Phe
145                 150                 155                 160

Met Ala His Gly Ser Leu Tyr Asn His Leu His Gly Lys Asn Lys Ala
                165                 170                 175

Leu Lys Glu Gln Leu Asp Trp Val Lys Arg Val Thr Ile Ala Val Gln
            180                 185                 190

Ala Ala Arg Gly Ile Glu Tyr Leu His Gly Tyr Ala Cys Pro Pro Val
        195                 200                 205

Ile His Arg Asp Ile Lys Ser Ser Asn Ile Leu Ile Asp Glu Glu His
    210                 215                 220

Asn Ala Arg Val Ala Asp Phe Gly Leu Ser Leu Leu Gly Pro Val Asp
225                 230                 235                 240

Ser Gly Ser Pro Leu Ala Glu Leu Pro Ala Gly Thr Leu Gly Tyr Leu
                245                 250                 255

Asp Pro Glu Tyr Tyr Arg Leu His Tyr Leu Thr Thr Lys Ser Asp Val
            260                 265                 270

Tyr Ser Phe Gly Val Leu Leu Leu Glu Ile Leu Ser Gly Arg Lys Ala
        275                 280                 285

Ile Asp Met His Tyr Glu Glu Gly Asn Ile Val Glu Trp Ala Val Pro
    290                 295                 300

Leu Ile Lys Ala Gly Asp Ile Thr Ser Ile Leu Asp Pro Val Leu Lys
305                 310                 315                 320

Gln Pro Thr Glu Ile Glu Ala Leu Arg Arg Ile Val Ser Val Ala Cys
```

```
                  325                 330                 335
Lys Cys Val Arg Met Arg Gly Lys Asp Arg Pro Ser Met Asp Lys Val
                340                 345                 350

Thr Thr Ser Leu Glu Arg Ala Leu Ala Gln Leu Met Gly Asn Pro Ser
                355                 360                 365

Ser Glu Gln Pro Ile Leu Pro Thr Glu Val Val Leu Gly Ser Ser Arg
            370                 375                 380

Met His Lys Lys Ser Trp Arg Ile Gly Ser Glu Asn Thr Glu Phe Arg
385                 390                 395                 400

Gly Gly Ser Trp Ile Thr Phe Pro Ser Val Thr Ser Ser Gln Arg Arg
                405                 410                 415

Lys Ser Ser Ala Ser Glu Gly Asp Val Ala Glu Glu Val Glu Asp Glu
                420                 425                 430

Gly Arg Lys Gln Gln Glu Ala Leu Arg Ser Leu Glu Glu Glu Ile Gly
            435                 440                 445

Pro Ala Ser Pro Gly Gln Ser Leu Phe Leu His His Asn Phe
        450                 455                 460

<210> SEQ ID NO 99
<211> LENGTH: 612
<212> TYPE: DNA
<213> ORGANISM: Brassica napus

<400> SEQUENCE: 99
gccaggagac acaagattgc gttgggaata gcgagaggac ttgcttatct tcacaccgga      60
caagaagctc ccatcatcca cggcaatata agatcgaaaa acgtgctggt ggacgacttc     120
ttcttcgcta ggctgactga gtttgggctt gataagatca tggtgcaagc ggtggcggat     180
gagatagtct cgcaggcgaa atcagacgga tacaaggcgc ctgagcttca caagatgaag     240
aaatgcaacc cgagaagcga tgtttacgcc tttgggatcc ttctcctgga gatactgatg     300
ggcaagaagc tgggaagag tgggaggaac ggtggtgagt atgttgatct accttctttg      360
gttaaagccg cggtgttgga ggagacgacg atggaggttt cgacttgga ggcgatgaaa      420 gggatcagga gtccgatgga ggaaggtttg gttcatgcgt tgaagctggc gatgggatgc     480
tgtgctcctg ttacgacggt tagaccgagt atggaagagg ttgtgaagca gttggaagag     540
aacaggccga ggaatagatc agcgttgtat agccctacgg aaacgaggag cgacgctgag     600
acaccatgct ga                                                         612

<210> SEQ ID NO 100
<211> LENGTH: 203
<212> TYPE: PRT
<213> ORGANISM: Brassica napus

<400> SEQUENCE: 100

Ala Arg Arg His Lys Ile Ala Leu Gly Ile Ala Arg Gly Leu Ala Tyr
1               5                   10                  15

Leu His Thr Gly Gln Glu Ala Pro Ile Ile His Gly Asn Ile Arg Ser
                20                  25                  30

Lys Asn Val Leu Val Asp Asp Phe Phe Phe Ala Arg Leu Thr Glu Phe
            35                  40                  45

Gly Leu Asp Lys Ile Met Val Gln Ala Val Ala Asp Glu Ile Val Ser
        50                  55                  60

Gln Ala Lys Ser Asp Gly Tyr Lys Ala Pro Glu Leu His Lys Met Lys
65                  70                  75                  80
```

Lys Cys Asn Pro Arg Ser Asp Val Tyr Ala Phe Gly Ile Leu Leu Leu
            85                  90                  95

Glu Ile Leu Met Gly Lys Lys Pro Gly Lys Ser Gly Arg Asn Gly Gly
        100                 105                 110

Glu Tyr Val Asp Leu Pro Ser Leu Val Lys Ala Ala Val Leu Glu Glu
            115                 120                 125

Thr Thr Met Glu Val Phe Asp Leu Glu Ala Met Lys Gly Ile Arg Ser
        130                 135                 140

Pro Met Glu Glu Gly Leu Val His Ala Leu Lys Leu Ala Met Gly Cys
145                 150                 155                 160

Cys Ala Pro Val Thr Thr Val Arg Pro Ser Met Glu Glu Val Val Lys
                165                 170                 175

Gln Leu Glu Glu Asn Arg Pro Arg Asn Arg Ser Ala Leu Tyr Ser Pro
            180                 185                 190

Thr Glu Thr Arg Ser Asp Ala Glu Thr Pro Cys
        195                 200

<210> SEQ ID NO 101
<211> LENGTH: 1278
<212> TYPE: DNA
<213> ORGANISM: Brassica napus

<400> SEQUENCE: 101

| | | | | |
|---|---|---|---|---|
| atgaagtgtt | tcaagttctc | tagtggtgac | aagaaagaag | aacacaacaa | gactcccaag | 60 |
| tctgtctcac | tgacctctaa | cttctccgac | cgcgacataa | accgaagcgg | gtcggatttc | 120 |
| aactctcgag | acgcctctgg | gacgagcacg | gagtcgtcca | tggggaggaa | gaactcgtac | 180 |
| ccttcaatgt | ctgctagaga | aagtaatctc | agagagttca | gcgttactga | tctcaaggct | 240 |
| gcgactaaga | actttagccg | ctctgttatg | attggagaag | gagggttcgg | ttgtgtcttc | 300 |
| aggggaacag | tgagggactt | ggaagatccg | tcgattaaaa | tcgaagtcgc | ggttaagcag | 360 |
| ctcggtaaaa | gagggttgca | ggggcataag | gaatgggtca | cggaagtgaa | ctttcttggt | 420 |
| gtggttgagc | attcaaactt | ggtgaagttg | cttggttact | gtgcagaaga | tgatgaacgt | 480 |
| gggatccaac | ggcttttggt | ttatgaatac | atgccaaacc | gaagcgttga | gtcccactta | 540 |
| tccccctcgct | cactcacagt | ccttacttgg | gatctaaggc | tgagaatcgc | tcaagatgca | 600 |
| gctcgtggtt | taacatacct | gcatgaacaa | atggagtttc | agataatatt | cagggacttt | 660 |
| aagtcctcga | cattctctt | ggatgaggac | tggaaagcaa | agctctctga | ctttggcctg | 720 |
| gctcgtttag | gtccatctga | aggactaact | catgttacta | ctgatgttgt | aggtacaatg | 780 |
| gcttatgcag | ctcctgagta | tattcaaact | ggtcgtctca | catcaaaaag | cgatgtgtgg | 840 |
| ggttatggag | tgtttatcta | cgagctcatc | acagggagga | aaccagttga | taggaacaaa | 900 |
| cctaagggag | agcagaagct | tctagaatgg | gtgagacctt | atctatcaga | cacaaggaag | 960 |
| ttcaagctca | tattagaccc | gaggctagaa | gggaagtacc | ctctcaaatc | agttcagaag | 1020 |
| ctagcggttg | tggccaacag | tgtgtttagtt | agaaacccaa | aggcacgtcc | caagatgagt | 1080 |
| gaagtgctgg | agatggtgaa | caagattgtg | gaagcgcctt | catgtagcgg | tactagcccg | 1140 |
| cagctagttc | cgctgcaggg | tctggagact | tccagagacg | ctggaggagg | gaaaaagaag | 1200 |
| agggggtttag | agaatggtgg | tggtgaagga | ggttggtttg | gtaagttatg | gaacccaaag | 1260 |
| acaataagag | cttgttga | | | | | 1278 |

<210> SEQ ID NO 102
<211> LENGTH: 425

<212> TYPE: PRT
<213> ORGANISM: Brassica napus

<400> SEQUENCE: 102

```
Met Lys Cys Phe Lys Phe Ser Ser Gly Asp Lys Lys Glu Glu His Asn
1               5                   10                  15

Lys Thr Pro Lys Ser Val Ser Leu Thr Ser Asn Phe Ser Asp Arg Asp
            20                  25                  30

Ile Asn Arg Ser Gly Ser Asp Phe Asn Ser Arg Asp Ala Ser Gly Thr
        35                  40                  45

Ser Thr Glu Ser Ser Met Gly Arg Lys Asn Ser Tyr Pro Ser Met Ser
    50                  55                  60

Ala Arg Glu Ser Asn Leu Arg Glu Phe Ser Val Thr Asp Leu Lys Ala
65                  70                  75                  80

Ala Thr Lys Asn Phe Ser Arg Ser Val Met Ile Gly Glu Gly Gly Phe
                85                  90                  95

Gly Cys Val Phe Arg Gly Thr Val Arg Asp Leu Glu Asp Pro Ser Ile
            100                 105                 110

Lys Ile Glu Val Ala Val Lys Gln Leu Gly Lys Arg Gly Leu Gln Gly
        115                 120                 125

His Lys Glu Trp Val Thr Glu Val Asn Phe Leu Gly Val Val Glu His
    130                 135                 140

Ser Asn Leu Val Lys Leu Leu Gly Tyr Cys Ala Glu Asp Asp Glu Arg
145                 150                 155                 160

Gly Ile Gln Arg Leu Leu Val Tyr Glu Tyr Met Pro Asn Arg Ser Val
                165                 170                 175

Glu Ser His Leu Ser Pro Arg Ser Leu Thr Val Leu Thr Trp Asp Leu
            180                 185                 190

Arg Leu Arg Ile Ala Gln Asp Ala Ala Arg Gly Leu Thr Tyr Leu His
        195                 200                 205

Glu Gln Met Glu Phe Gln Ile Ile Phe Arg Asp Phe Lys Ser Ser Asn
    210                 215                 220

Ile Leu Leu Asp Glu Asp Trp Lys Ala Lys Leu Ser Asp Phe Gly Leu
225                 230                 235                 240

Ala Arg Leu Gly Pro Ser Glu Gly Leu Thr His Val Thr Thr Asp Val
                245                 250                 255

Val Gly Thr Met Ala Tyr Ala Ala Pro Glu Tyr Ile Gln Thr Gly Arg
            260                 265                 270

Leu Thr Ser Lys Ser Asp Val Trp Gly Tyr Gly Val Phe Ile Tyr Glu
        275                 280                 285

Leu Ile Thr Gly Arg Lys Pro Val Asp Arg Asn Lys Pro Lys Gly Glu
    290                 295                 300

Gln Lys Leu Leu Glu Trp Val Arg Pro Tyr Leu Ser Asp Thr Arg Lys
305                 310                 315                 320

Phe Lys Leu Ile Leu Asp Pro Arg Leu Glu Gly Lys Tyr Pro Leu Lys
                325                 330                 335

Ser Val Gln Lys Leu Ala Val Val Ala Asn Arg Cys Leu Val Arg Asn
            340                 345                 350

Pro Lys Ala Arg Pro Lys Met Ser Glu Val Leu Glu Met Val Asn Lys
        355                 360                 365

Ile Val Glu Ala Pro Ser Cys Ser Gly Thr Ser Pro Gln Leu Val Pro
    370                 375                 380

Leu Gln Gly Leu Glu Thr Ser Arg Asp Ala Gly Gly Gly Lys Lys Lys
385                 390                 395                 400
```

-continued

```
Arg Gly Leu Glu Asn Gly Gly Gly Glu Gly Gly Trp Phe Gly Lys Leu
            405                 410                 415

Trp Asn Pro Lys Thr Ile Arg Ala Cys
            420             425
```

METHOD FOR SPEEDING UP PLANT GROWTH AND IMPROVING YIELD BY ALTERING EXPRESSION LEVELS OF KINASES AND PHOSPHATASES

CROSS-REFERENCE TO RELATED APPLICATIONS

This application claims the benefit under 35 U.S.C. §119 (e) of U.S. Provisional Patent Application No. 61/482,467, filed May 4, 2011, which is hereby incorporated by reference in its entirety.

1. INTRODUCTION

Described herein are methods for speeding up plant growth and/or elevating plant yields by altering the expression levels of plant kinases and phosphatases. Also described therein are the use of plant kinases and phosphatases, and their respective protein products, as well as fragments, derivatives, homologues, and variants thereof.

2. BACKGROUND OF THE INVENTION

Purple acid phosphatases (PAPs) catalyze the hydrolysis of a wide range of activated phosphoric acid mono- and di-esters and anhydrides (Klabunde et al., 1996). The PAP proteins are characterized by seven conserved amino acid residues (shown in bold face) in the five conserved motifs XDXX, XDXXY, GNH(D/E), XXXH, XHXH, which are involved in the coordination of the dimetal nuclear center ($Fe^{3+}$-$Me^{2+}$) in the active site (Li et al., 2002), where Me is a transition metal; $Me^{2+}$ is mostly found to be $Fe^{2+}$ in mammals, and $Zn^{2+}$, or $Mn^{2+}$ in plants (Klabunde and Krebs, 1997; Schenk et al., 1999).

Multiple PAP-like sequences are present in plant genomes. In the *Arabidopsis* genome, twenty-nine potential PAP genes have been identified based on sequence comparison. Most of the functions of characterized plant PAPs are related to phosphorus metabolism. None of the plant PAPs that had been functionally or biochemically characterized carry any transmembrane motif. In addition, no AtPAPs or any other plant PAPs had been discovered to affect sugar signalling and carbon metabolism in plants. Overexpression of AtPAP2 in *Arabidopsis*, a PAP with a C-terminal motif, can significantly speed up plant growth, increase sugar content in plants and improve seed yield (U.S. Patent Application Publication No. 2010/0159065).

3. SUMMARY

In one aspect, provided herein are methods that speed up or increase the rate of plant growth and elevate plant yields by altering the expression levels of plant kinases and phosphatases. Kinases and phosphatases, and their respectively encoded protein products, as well as fragments, derivatives, homologues, and variants thereof, are disclosed. Methods for introducing these genes into plants to speed up or increase the growth rate of plants, and to increase yield of plants, are provided. The kinases and phosphatases of the present invention are selected from the results of a microarray study. Surprisingly, it is discovered that phosphatases (such as NG6) and kinases (such as NG21, NG24, NG28, and NG32) have growth-promoting effects.

Provided herein, a microarray study was carried out to compare the gene expression profiles of the AtPAP2 overexpression lines, AtPAP2 T-DNA (mutant) line, and the wild-type plants. The results showed that expression levels of a number of genes are significantly altered (upregulated or downregulated) in AtPAP2 overexpression lines, when compared to the wild-type. Among these genes, a number of phosphatases and kinases were selected and analyzed using transgenic studies in *Arabidopsis*.

At least in part, the present inventors discover that altering the expression levels of plant phosphatases (such as NG6) and kinases (such as NG21, NG24, NG28 and NG32) in plants resulted in rapid plant growth and higher yield. In one aspect, provided herein are methods of producing plants with enhanced growth and/or yield. In one embodiment, the method comprises: transforming a plant or plant cell with a nucleic acid molecule comprising a plant kinase and/or phosphatase gene selected from SEQ ID NO: 1, 3, 5, 7, 9, 11, 13, 15, 17, 19, 21, 23, 25, 27, 29, 31, 33, 35, 37, 39, 41, 43, 45, 47, 49, 93, 95, 97, 99, or 101, and over-expressing said kinase and/or phosphatase gene in the plant or plant cell. In one embodiment, provided herein are methods of regenerating, from said transformed plant or plant cell, a plant having enhanced growth and/or yield.

In one embodiment, the method comprises: transforming a plant or plant cell with a nucleic acid molecule comprising a plant kinase and/or phosphatase having at least 65%, 70%, 75%, 80%, 85%, 90%, 93%, 95%, 96%, 97%, 98%, or 99% identity with SEQ ID NO: 1, 3, 5, 7, 9, 11, 13, 15, 17, 19, 21, 23, 25, 27, 29, 31, 33, 35, 37, 39, 41, 43, 45, 47, 49, 93, 95, 97, 99, or 101, and over-expressing said kinase and/or phosphatase gene in the plant or plant cell.

In certain embodiments, the method comprises transforming a plant or plant cell with a nucleic acid molecule comprising a plant kinase and/or phosphatase having a nucleic acid fragment from SEQ ID NO: 1, 3, 5, 7, 9, 11, 13, 15, 17, 19, 21, 23, 25, 27, 29, 31, 33, 35, 37, 39, 41, 43, 45, 47, 49, 93, 95, 97, 99 or 101. In certain embodiments, the nucleic acid fragment encode a peptide that has the same activity as a peptide encoded by SEQ ID NO: 1, 3, 5, 7, 9, 11, 13, 15, 17, 19, 21, 23, 25, 27, 29, 31, 33, 35, 37, 39, 41, 43, 45, 47, 49, 93, 95, 97, 99 or 101.

In certain embodiments, the activity is a kinase and/or phosphatase activity. In certain, embodiments, the method comprises transforming a plant or plant cell with a nucleic and molecule comprising a plant kinase and/or phosphatase having a variant from SEQ ID NO: 1, 3, 5, 7, 9, 11, 13, 15, 17, 19, 21, 23, 25, 27, 29, 31, 33, 35, 37, 39, 41, 43, 45, 47, 49, 93, 95, 97, 99 or 101.

In certain embodiments, the variant has 1-5, 6-10, 11-20, 21-30, 31-40, 41-50, 50-70, 71-80, 81-100 nucleic acid deletion, substitution or insertion in the sequence as compared to SEQ ID NO: 1, 3, 5, 7, 9, 11, 13, 15, 17, 19, 21, 23, 25, 27, 29, 31, 33, 35, 37, 39, 41, 43, 45, 47, 49, 93, 95, 97, 99, or 101. In certain embodiments, the variants encode a peptide that has the same activity as a peptide encoded by SEQ ID NO: 1, 3, 5, 7, 9, 11, 13, 15, 17, 19, 21, 23, 25, 27, 29, 31, 33, 35, 37, 39, 41, 43, 45, 47, 49, 93, 95, 97, 99, or 101. In certain embodiments, the activity is a kinase and/or phosphatase activity.

Provided herein are transgenic plants with enhanced growth and/or yield. In certain embodiments, the transgenic plant comprises a nucleic acid molecule selected from SEQ ID NO: 1, 3, 5, 7, 9, 11, 13, 15, 17, 19, 21, 23, 25, 27, 29, 31, 33, 35, 37, 39, 41, 43, 45, 47, 49, 93, 95, 97, 99, or 101, wherein said nucleic acid molecule is overexpressed in the transgenic plant when compared to a wild-type plant of the same species cultivated under the same conditions.

In certain embodiments, the transgenic plant comprises a nucleic acid molecule having at least 65%, 70%, 75%, 80%, 85%, 90%, 93%, 95%, 96%, 97%, 98% or 99% identity with SEQ ID NO: 1, 3, 5, 7, 9, 11, 13, 15, 17, 19, 21, 23, 25, 27, 29, 31, 33, 35, 37, 39, 41, 43, 45, 47, 49, 93, 95, 97, 99, or 101, wherein said nucleic acid molecule is overexpressed in the transgenic plant when compared to a wild-type plant of the same species cultivated under the same conditions.

In certain embodiments, the transgenic plant comprises a nucleic acid fragment from SEQ ID NO: 1, 3, 5, 7, 9, 11, 13, 15, 17, 19, 21, 23, 25, 27, 29, 31, 33, 35, 37, 39, 41, 43, 45, 47, 49, 93, 95, 97, 99, or 101. In certain embodiments, the nucleic acid fragment encodes a peptide that has the same activity as a peptide encoded by SEQ ID NO: 1, 3, 5, 7, 9, 11, 13, 15, 17, 19, 21, 23, 25, 27, 29, 31, 33, 35, 37, 39, 41, 43, 45, 47, 49, 93, 95, 97, 99, or 101. In certain embodiments, the activity is a kinase and/or phosphatase activity.

In certain embodiments, the transgenic plant comprises a plant kinase and/or phosphatase homologue, derivative, or variant having a nucleic acid sequence of the SEQ ID NO: 1, 3, 5, 7, 9, 11, 13, 15, 17, 19, 21, 23, 25, 27, 29, 31, 33, 35, 37, 39, 41, 43, 45, 47, 49, 93, 95, 97, 99, or 101. In certain embodiments, the homologue, derivative or variant has 1-5, 6-10, 11-20, 21-30, 31-40, 41-50, 50-70, 71-80, 81-100 nucleic acid deletion, substitution or insertion in the sequence as compared to SEQ ID NO: 1, 3, 5, 7, 9, 11, 13, 15, 17, 19, 21, 23, 25, 27, 29, 31, 33, 35, 37, 39, 41, 43, 45, 47, 49, 93, 95, 97, 99, or 101. In certain embodiments, the variants encode a peptide that has the same activity as a peptide encoded by SEQ ID NO: 1, 3, 5, 7, 9, 11, 13, 15, 17, 19, 21, 23, 25, 27, 29, 31, 33, 35, 37, 39, 41, 43, 45, 47, 49, 93, 95, 97, 99 or 101. In certain embodiments, the activity is a kinase and/or phosphatase activity.

In certain embodiments provided herein are the methods of altering the expression levels of plant kinase and/or phosphatase. In certain embodiments, the method comprises transforming a plant or plant cell with a nucleic acid molecule that expresses a plant kinase and/or phosphatase peptide, fragment, derivative or variant from a peptide having an amino acid sequence of SEQ ID NO: 2, 4, 6, 8, 10, 12, 14, 16, 18, 20, 22, 24, 26, 28, 30, 32, 34, 36, 38, 40, 42, 44, 46, 48, 50, 94, 96, 98, 100, or 102. In certain embodiments, the peptide, fragment, derivative or variant is overexpressed. In certain embodiments, provided herein are methods of regenerating, from said transformed plant or plant cell, a plant having enhanced growth and/or yield.

In certain embodiments, the transgenic plants express a plant kinase and/or phosphatase peptide, fragment, derivative or variant from a protein having an amino acid sequence of SEQ ID NO: 2, 4, 6, 8, 10, 12, 14, 16, 18, 20, 22, 24, 26, 28, 30, 32, 34, 36, 38, 40, 42, 44, 46, 48, 50, 94, 96, 98, 100, or 102. In certain embodiments, the peptide fragment, derivative or variant is overexpressed. In certain embodiments, provided herein are regenerated transformed plant having enhanced growth and/or yield.

4. BRIEF DESCRIPTION OF THE FIGURES

Figure 4:
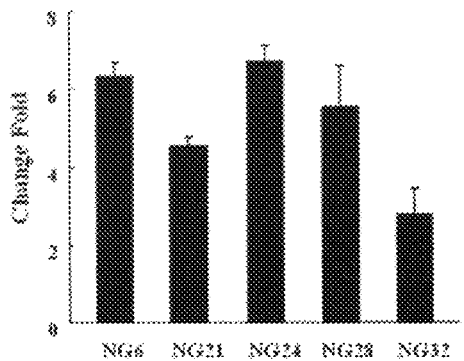
Figure 4:
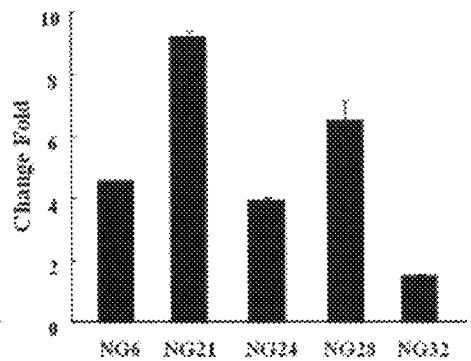

FIG. 4 shows the mRNA expression levels of NG genes in the respective overexpression lines. The mRNA expression levels in 10-day-old T3 homologous seedlings were determined by quantitative RT-PCR using gene-specific primers. The fold-changes represent the relative expression levels of mRNAs compared to that of the wild-type (WT=1.0). The results of two trials were obtained from two batches of plant growth studies.

Figure 5:
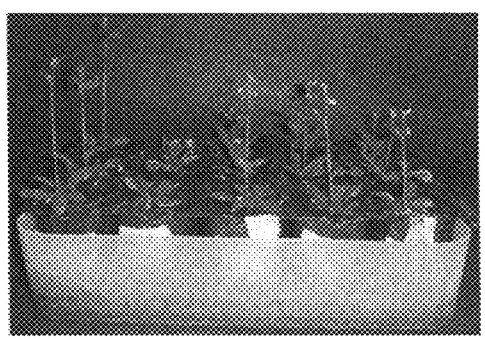
Figure 5:

FIG. 5 shows the growth performance of the wild-type and NG6 over-expression lines in soil. The five columns of plants from left to right were AtPAP2 overexpression lines, WT, T3 homologous NG6 overexpression lines NG6-1, NG6-2, and NG6-3. (a) 22-day-old and (b) 25-day-old plants.

Figure 6:
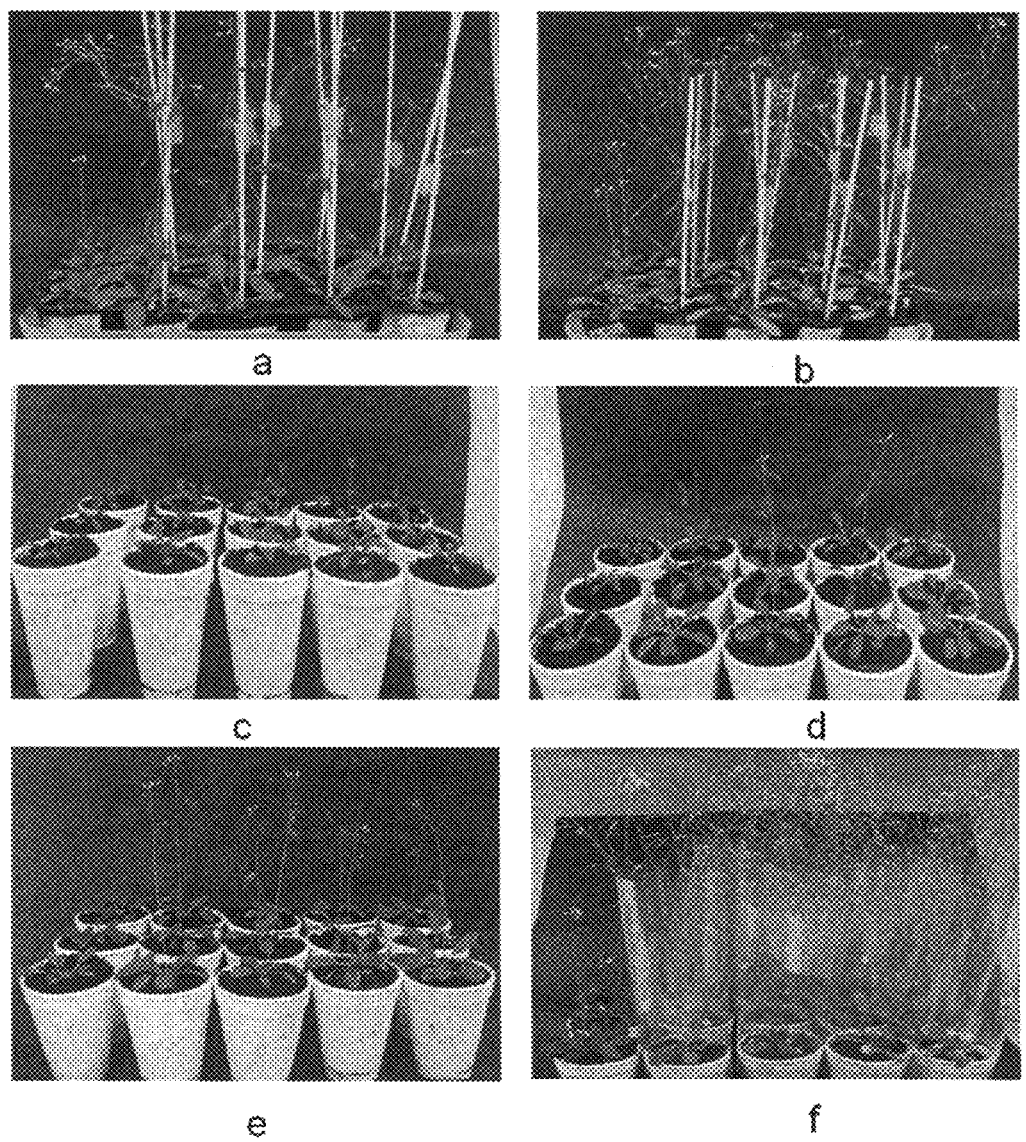

FIG. 6 shows the growth performance of the wild-type and T3 homologous NG21, NG24, NG28 and NG32 overexpression lines in soil. The five columns of plants from left to right were WT, NG21, NG24, NG28 and NG32 overexpression lines. (a) 30-day-old plants and (b) 34-day-old plants grown in black tray. (c) 22-day-old plants, (d) 25-day-old plants, (e) 28-day-old plants, and (f) 36-day-old plants grown in white cups.

4.1. BRIEF DESCRIPTION OF THE SEQUENCES

SEQ ID NO:1 is a nucleic acid sequence of *Arabidopsis* phosphatase NG6 gene.

SEQ ID NO:2 is an amino acid sequence of *Arabidopsis* phosphatase NG6.

SEQ ID NO:3 is a nucleic acid sequence of maize phosphatase NG6 gene.

SEQ ID NO:4 is an amino acid sequence of maize phosphatase NG6.

SEQ ID NO:5 is a nucleic acid sequence of soybean phosphatase NG6 gene.

SEQ ID NO:6 is an amino acid sequence of soybean phosphatase NG6.

SEQ ID NO:7 is a nucleic acid sequence of rice phosphatase NG6 gene.

SEQ ID NO:8 is an amino acid sequence of rice phosphatase NG6.

SEQ ID NO:9 is a nucleic acid sequence of cotton phosphatase NG6 gene.

SEQ ID NO:10 is an amino acid sequence of cotton phosphatase NG6.

SEQ ID NO:11 is a nucleic acid sequence of *Arabidopsis* kinase NG21 gene.

SEQ ID NO:12 is an amino acid sequence of *Arabidopsis* kinase NG21.

SEQ ID NO:13 is a nucleic acid sequence of maize kinase NG21 gene.

SEQ ID NO:14 is an amino acid sequence of maize kinase NG21.

SEQ ID NO:15 is a nucleic acid sequence of soybean kinase NG21 gene.

SEQ ID NO:16 is an amino acid sequence of soybean kinase NG21.

SEQ ID NO:17 is a nucleic acid sequence of rice kinase NG21 gene.

SEQ ID NO:18 is an amino acid sequence of rice kinase NG21.

SEQ ID NO:19 is a nucleic acid sequence of cotton kinase NG21 gene.

SEQ ID NO:20 is an amino acid sequence of cotton kinase NG21.
SEQ ID NO:21 is a nucleic acid sequence of *Arabidopsis* kinase NG24 gene.
SEQ ID NO:22 is an amino acid sequence of *Arabidopsis* kinase NG24.
SEQ ID NO:23 is a nucleic acid sequence of maize kinase NG24 gene.
SEQ ID NO:24 is an amino acid sequence of maize kinase NG24.
SEQ ID NO:25 is a nucleic acid sequence of soybean kinase NG24 gene.
SEQ ID NO:26 is an amino acid sequence of soybean kinase NG24.
SEQ ID NO:27 is a nucleic acid sequence of rice kinase NG24 gene.
SEQ ID NO:28 is an amino acid sequence of rice kinase NG24.
SEQ ID NO:29 is a nucleic acid sequence of cotton kinase NG24 gene.
SEQ ID NO:30 is an amino acid sequence of cotton kinase NG24.
SEQ ID NO:31 is a nucleic acid sequence of *Arabidopsis* kinase NG28 gene.
SEQ ID NO:32 is an amino acid sequence of *Arabidopsis* kinase NG28.
SEQ ID NO:33 is a nucleic acid sequence of maize kinase NG28 gene.
SEQ ID NO:34 is an amino acid sequence of maize kinase NG28.
SEQ ID NO:35 is a nucleic acid sequence of soybean kinase NG28 gene.
SEQ ID NO:36 is an amino acid sequence of soybean kinase NG28.
SEQ ID NO:37 is a nucleic acid sequence of rice kinase NG28 gene.
SEQ ID NO:38 is an amino acid sequence of rice kinase NG28.
SEQ ID NO:39 is a nucleic acid sequence of cotton kinase NG28 gene.
SEQ ID NO:40 is an amino acid sequence of cotton kinase NG28.
SEQ ID NO:41 is a nucleic acid sequence of *Arabidopsis* kinase NG32 gene.
SEQ ID NO:42 is an amino acid sequence of *Arabidopsis* kinase NG32.
SEQ ID NO:43 is a nucleic acid sequence of maize kinase NG32 gene.
SEQ ID NO:44 is an amino acid sequence of maize kinase NG32.
SEQ ID NO:45 is a nucleic acid sequence of soybean kinase NG32 gene.
SEQ ID NO:46 is an amino acid sequence of soybean kinase NG32.
SEQ ID NO:47 is a nucleic acid sequence of rice kinase NG32 gene.
SEQ ID NO:48 is an amino acid sequence of rice kinase NG32.
SEQ ID NO:49 is a nucleic acid sequence of cotton kinase NG32 gene.
SEQ ID NO:50 is an amino acid sequence of cotton kinase NG32.
SEQ ID NO:51 is a primer sequence useful according to the present invention.
SEQ ID NO:52 is a primer sequence useful according to the present invention.
SEQ ID NO:53 is a primer sequence useful according to the present invention.
SEQ ID NO:54 is a primer sequence useful according to the present invention.
SEQ ID NO:55 is a primer sequence useful according to the present invention.
SEQ ID NO:56 is a primer sequence useful according to the present invention.
SEQ ID NO:57 is a primer sequence useful according to the present invention.
SEQ ID NO:58 is a primer sequence useful according to the present invention.
SEQ ID NO:59 is a primer sequence useful according to the present invention.
SEQ ID NO:60 is a primer sequence useful according to the present invention.
SEQ ID NO:61 is a primer sequence useful according to the present invention.
SEQ ID NO:62 is a primer sequence useful according to the present invention.
SEQ ID NO:63 is a primer sequence useful according to the present invention.
SEQ ID NO:64 is a primer sequence useful according to the present invention.
SEQ ID NO:65 is a primer sequence useful according to the present invention.
SEQ ID NO:66 is a primer sequence useful according to the present invention.
SEQ ID NO:67 is a primer sequence useful according to the present invention.
SEQ ID NO:68 is a primer sequence useful according to the present invention.
SEQ ID NO:69 is a primer sequence useful according to the present invention.
SEQ ID NO:70 is a primer sequence useful according to the present invention.
SEQ ID NO:71 is a primer sequence useful according to the present invention.
SEQ ID NO:72 is a primer sequence useful according to the present invention.
SEQ ID NO:73 is a nucleic acid sequence of *Arabidopsis* AtPAP2 phosphatase gene.
SEQ ID NO:74 is an amino acid sequence of *Arabidopsis* AtPAP2 phosphatase.
SEQ ID NO:75 is an amino acid sequence of a conserved motif of an NG6 protein.
SEQ ID NO:76 is an amino acid sequence of a conserved motif of an NG6 protein.
SEQ ID NO:77 is an amino acid sequence of a conserved motif of an NG6 protein.
SEQ ID NO:78 is an amino acid sequence of a conserved motif of an NG6 protein.
SEQ ID NO:79 is an amino acid sequence of a conserved motif of an NG21 protein.
SEQ ID NO:80 is an amino acid sequence of a conserved motif of an NG21 protein.
SEQ ID NO:81 is an amino acid sequence of a conserved motif of an NG21 protein.
SEQ ID NO:82 is an amino acid sequence of a conserved motif of an NG21 protein.
SEQ ID NO:83 is an amino acid sequence of a conserved motif of an NG24 protein.
SEQ ID NO:84 is an amino acid sequence of a conserved motif of an NG24 protein.
SEQ ID NO:85 is an amino acid sequence of a conserved motif of an NG24 protein.

SEQ ID NO:86 is an amino acid sequence of a conserved motif of an NG28 protein.

SEQ ID NO:87 is an amino acid sequence of a conserved motif of an NG28 protein.

SEQ ID NO:88 is an amino acid sequence of a conserved motif of an NG28 protein.

SEQ ID NO:89 is an amino acid sequence of a conserved motif of an NG32 protein.

SEQ ID NO:90 is an amino acid sequence of a conserved motif of an NG32 protein.

SEQ ID NO:91 is an amino acid sequence of a conserved motif of an NG32 protein.

SEQ ID NO:92 is an amino acid sequence of a conserved motif of an NG32 protein.

SEQ ID NO:93 is a nucleic acid sequence of rapeseed kinase NG6 gene.

SEQ ID NO:94 is an amino acid sequence of rapeseed kinase NG6.

SEQ ID NO:95 is a nucleic acid sequence of rapeseed kinase NG21 gene.

SEQ ID NO:96 is an amino acid sequence of rapeseed kinase NG21.

SEQ ID NO:97 is a nucleic acid sequence of rapeseed kinase NG24 gene.

SEQ ID NO:98 is an amino acid sequence of rapeseed kinase NG24.

SEQ ID NO:99 is a nucleic acid sequence of rapeseed kinase NG28 gene.

SEQ ID NO:100 is an amino acid sequence of rapeseed kinase NG28.

SEQ ID NO:101 is a nucleic acid sequence of rapeseed kinase NG32 gene.

SEQ ID NO:102 is an amino acid sequence of rapeseed kinase NG32.

5. DETAILED DESCRIPTION

Provided herein are methods of producing plants with enhanced growth and/or yield. In one embodiment, the method comprises: transforming a plant or plant cell with a nucleic acid molecule comprising a plant kinase and/or phosphatase gene selected from NG6, NG21, NG24, NG28, and NG32, and over-expressing said kinase and/or phosphatase gene in the plant or plant cell. In one embodiment, the method further comprises: regenerating, from said transformed plant or plant cell, a plant having enhanced growth and/or yield. Also provided are transgenic plants with enhanced growth and/or yield, comprising a plant kinase and/or phosphatase gene selected from NG6, NG21, NG24, NG28, and NG32, wherein the kinase and/or phosphatase is overexpressed in the plant or plant cell.

The inventors discover that altering the expression levels of one or more phosphatases (such as NG6) and kinases (such as NG21, NG24, NG28, and NG32) results in rapid plant growth and higher yield. The gene expression profiles of the AtPAP2 overexpression lines, AtPAP2 T-DNA (mutant) line, and the wild-type plants are analyzed using microarray. The microarray data show that the expression levels of a range of genes are significantly altered (upregulated or downregulated) in the AtPAP2 overexpression lines, when compared to the wild-type.

The introduction of a representative gene of phosphatases (AT1G05000 (NG6)) and kinases (AT1G13350 (NG21), AT1G28390 (NG24), AT3G24660 (NG28) and AT5G03320 (NG32)), into the genome of *Arabidopsis* by transgenic technology produced transgenic *Arabidopsis* that grew faster than the wild-type plants (Table 4, FIG. 5, FIG. 6), and the yield of seeds were elevated by 23-70% (Table 5).

While any plant species can be modified using the methods described herein, preferably included without limitation are species from the following genera with representative species in parentheses:

Monocots: genera *Asparagus* (asparagus), *Bromus* (cheatgrass), *Hemerocallis* (daylily), *Hordeum* (barley), *Lolium* (ryegrass), *Oryza* (rice), *Panicum* (Switchgrass), *Pennisetum* (fountaingrass), *Saccharum* (Sugar cane), *Sorghum, Trigonella* (fenu grass), *Triticum* (wheat), and *Zea* (corn); and Dicots: genera *Antirrhinum* (flower sp.), *Arabidopsis* (thaliana), *Arachis* (peanut), *Atropa* (deadly nightshade), *Brassica* (rapeseed), *Browallia, Capsicum* (pepper), *Carthamus* (safflower), *Cichorium* (chicory), *Citrus* (orange, lemon), *Chrysanthemum, Cucumis* (cucumber), *Datura* (thorn apple), *Daucus* (carrot), *Digitalis* (foxglove), *Fragaria* (strawberry), *Geranium* (flower sp.), *Glycine* (soybean), *Helianthus* (sunflower), *Hyscyamus, Ipomoea* (morning glory), *Latuca* (lettuce), *Linum* (linseed), *Lotus* (flower sp.), *Lycopersicon* (tomato), *Majorana, Malva* (cotton), *Manihot, Medicago* (alfalfa), *Nemesia, Nicotiana* (tobacco), *Onobrychis, Pelargonium* (citrosa), *Petunia* (flower sp.), *Ranunculus* (flower sp.), *Raphanus* (radishes), *Salpiglossis, Senecio* (flower sp.), *Sinapis* (albae semen), *Solanum* (potato), *Trifolium* (clovers), *Vigna* (mungbean, fava bean), and *Vitis* (grape).

In certain embodiments, plant species transgenically modified according to the present invention are selected from soybean, maize, potato, rice, sugar canes, switchgrass, cotton, sorghum, alfalfas, rapeseed, canola, rye, sorghum, sunflower, wheat, tobacco, millet, peanuts sweet potato cassava, coffee, coconut, cocoa, tea, banana, citrus, apple, pineapple, avocado, fig, guava, mango, olive, barley ornamentals, and conifers. In preferred embodiments, plant species transgenically modified according to the present invention are selected from soybean, maize, potato, rice, sugar canes, switchgrass, cotton, sorghum, alfalfas, rapeseed, and canola.

In certain embodiment, plant parts, plant tissue, and plant cells including, but not limited to, shoots, stems, seeds, and roots, can be transgenically modified in accordance with the present invention.

4.2 DEFINITIONS

The term "protein or peptide homologue," as used herein, refers to one or more of the following proteins or peptides: (i) a protein or polypeptide with at least about 60%, at least about 70%, at least about 80%, at least about 90%, or at least about 98% sequence identity with a protein or polypeptide of the invention; (ii) a protein or polypeptide encoded by a nucleotide sequence that is at least about 60%, at least about 70%, at least about 80%, at least about 90%, or at least about 98% identical to a nucleic acid sequence of the invention; (iii) a protein or polypeptide encoded by a nucleotide sequence that hybridizes under stringent conditions to a nucleotide sequence of the invention; (iv) a protein or polypeptide that is derived from conservative substitution of amino acids of a protein or polypeptide of the invention, or that is derived from conservative substitution of amino acids of a protein or polypeptide of (i)-(iii); (v) a fragment of a protein or polypeptide of the invention or a fragment of a protein or polypeptide of (i) through (iv); and (vii) a protein or polypeptide recognized by an antibody that immunospecifically binds to a sequence selected from SEQ ID NO: 2, 4, 6, 8, 10, 12, 14, 16, 18, 20, 22, 24, 26, 28, 30, 32, 34, 36, 38, 40, 42, 44, 46, 48, 50, 94, 96, 98, 100 or 102.

The term "an antibody or an antibody fragment that immunospecifically binds to a polypeptide selected from SEQ ID NO: 2, 4, 6, 8, 10, 12, 14, 16, 18, 20, 22, 24, 26, 28, 30, 32, 34, 36, 38, 40, 42, 44, 46, 48, 50, 94, 96, 98, 100 or 102" or "an antibody or an antibody fragment that immunospecifically binds to a polypeptide, peptide, or protein of the invention," as used herein, refers to an antibody or a fragment thereof that immunospecifically binds to a polypeptide selected from SEQ ID NO: 2, 4, 6, 8, 10, 12, 14, 16, 18, 20, 22, 24, 26, 28, 30, 32, 34, 36, 38, 40, 42, 44, 46, 48, 50, 94, 96, 98, 100 or 102, or a fragment of these polypeptide, wherein the antibody or the antibody fragment does not non-specifically bind to other peptides, polypeptides, or proteins.

An antibody or a fragment thereof that immunospecifically binds to a polypeptide selected from SEQ ID NO: 2, 4, 6, 8, 10, 12, 14, 16, 18, 20, 22, 24, 26, 28, 30, 32, 34, 36, 38, 40, 42, 44, 46, 48, 50, 94, 96, 98, 100 or 102, or a fragment of these polypeptide, may cross-react with other antigens. In a preferred embodiment, an antibody or a fragment thereof that immunospecifically binds to a polypeptide selected from SEQ ID NO: 2, 4, 6, 8, 10, 12, 14, 16, 18, 20, 22, 24, 26, 28, 30, 32, 34, 36, 38, 40, 42, 44, 46, 48, 50, 94, 96, 98, 100 or 102, or a fragment of these polypeptides, does not cross-react with other antigens. An antibody or a fragment thereof that immunospecifically binds to a polypeptide selected from SEQ ID NO: 2, 4, 6, 8, 10, 12, 14, 16, 18, 20, 22, 24, 26, 28, 30, 32, 34, 36, 38, 40, 42, 44, 46, 48, 50, 94, 96, 98, 100 or 102, or a fragment of these polypeptide, can be identified by, for example, immunoassays or other techniques known to those skilled in the art. An antibody or an antibody fragment that immunospecifically binds a polypeptide selected from SEQ ID NO: 2, 4, 6, 8, 10, 12, 14, 16, 18, 20, 22, 24, 26, 28, 30, 32, 34, 36, 38, 40, 42, 44, 46, 48, 50, 94, 96, 98, 100 or 102 may be interchangeably referred to as "anti-PAP antibody".

The term "peptide or protein derivative," as used herein, refers to a given peptide or protein that is modified, e.g., by covalent attachment of another molecule, to the peptide or protein, including the incorporation of non-naturally occurring amino acids. The peptide or protein derivative retains one or more biological activities of the peptide or protein.

The term "nucleic acid fragment," as used herein, refers to a fragment of a nucleic acid molecule of the invention, wherein the fragment comprises at least about 400, at least about 450, at least about 500, at least about 550, at least about 600, at least about 650, at least about 700, at least about 750, at least about 800, at least about 850, at least about 900, at least about 950, at least about 1000, at least about 1050, at least about 1100, at least about 1150, at least about 1200, at least about 1250, at least about 1300, or at least about 1350 contiguous nucleic acid bases of the nucleic acid molecule.

The term "protein or peptide fragment," as used herein, refers to a fragment of a protein or peptide of the invention, wherein the fragment comprises at least about 160, at least about 180, at least about 200, at least about 220, at least about 240, at least about 260, at least about 280, at least about 300, at least about 320, at least about 340, or at least about 360 contiguous amino acid residues of the protein or peptide.

The term "protein or peptide variant," as used herein, includes 1) a naturally occurring allelic variation of a given protein or peptide, and 2) a recombinantly prepared variation of a given protein or peptide, in which one or more amino acid residues have been modified by amino acid substitution, addition, and/or deletion.

An "isolated" nucleic acid molecule has been removed from any environment in which it may exist in nature. For instance, an "isolated" nucleic acid molecule, such as a cDNA molecule, is substantially free of other cellular materials, or culture medium when produced by recombinant techniques, or substantially free of chemical precursors or other chemicals when chemically synthesized. In a preferred embodiment, nucleic acid molecules encoding the polypeptides/proteins of the present invention are isolated or purified.

The term "under stringent conditions" refers to hybridization and washing conditions under which nucleotide sequences having homology to each other remain hybridized to each other. Such hybridization conditions are described in, for example, but not limited to, *Current Protocols in Molecular Biology*, John Wiley & Sons, N.Y. (1989), 6.3.1-6.3.6.; *Basic Methods in Molecular Biology*, Elsevier Science Publishing Co., Inc., N.Y. (1986), pp. 75-78, and 84-87; and *Molecular Cloning*, Cold Spring Harbor Laboratory, N.Y. (1982), pp. 387-389, and are well known to those skilled in the art. A preferred example of stringent hybridization conditions is hybridization in 6× sodium chloride/sodium citrate (SSC), 0.5% SDS at about 68° C. followed by one or more washes in 2×SSC, 0.5% SDS at room temperature. Another preferred, example of stringent hybridization conditions is hybridization in 6×SSC at about 45° C. followed by one or more washes in 0.2×SSC, 0.1% SDS at about 50-65° C.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions×100%). In one embodiment, the two sequences are the same length.

The determination of percent identity between two sequences can also be accomplished using a mathematical algorithm. A preferred, non limiting example of a mathematical algorithm utilized for the comparison of two sequences is the algorithm of Karlin and Altschul, 1990, Proc. Natl. Acad. Sci. U.S.A. 87:2264 2268, modified as in Karlin and Altschul, 1993, Proc. Natl. Acad. Sci. U.S.A. 90:5873 5877. Such an algorithm is incorporated into the NBLAST and) (BLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecules of the present invention. BLAST protein searches can be performed with the XBLAST program parameters set, e.g., to score 50, wordlength=3 to obtain amino acid sequences homologous to a protein molecule of the present invention. To obtain gapped alignments for comparison purposes, Gapped BLAST can be utilized as described in Altschul et al., 1997, Nucleic Acids Res. 25:3389 3402. Alternatively, PSI BLAST can be used to perform an iterated search which detects distant relationships between molecules (Id.). When utilizing BLAST, Gapped BLAST, and PSI Blast programs, the default parameters of the respective programs (e.g., of XBLAST and NBLAST) can be used (see, e.g., the NCBI website). Another preferred, non limiting example of a mathematical algorithm utilized for the comparison of sequences is the algorithm of Myers and Miller, 1988, CABIOS 4:11 17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

As used herein, the term "derivative" (e.g., proteins, polypeptides, peptides, and antibodies) refers to an agent that comprises an amino acid sequence which has been altered by the introduction of amino acid residue substitutions, deletions, and/or additions. The term "derivative" as used herein also refers to an agent which has been modified, i.e., by the covalent attachment of any type of molecule to the agent. For example, but not by way of limitation, an antibody may be modified, e.g., by glycosylation, acetylation, pegylation, phosphorylation, amidation, derivatization by known protecting/blocking groups, proteolytic cleavage, linkage to a cellular ligand or other protein, etc. A derivative of an agent may be produced by chemical modifications using techniques known to those of skill in the art, including, but not limited to specific chemical cleavage, acetylation, formylation, metabolic synthesis of tunicamycin, etc. Further, a derivative of an agent may contain one or more non-classical amino acids. A derivative of an agent possesses a similar or identical function as the agent from which it was derived.

The term "enhance or promote plant growth and/or yield" refers to for example, increased plant weight, increased leaf number and/or weight, increased number of inflorescence, increased seed production (such as weight/seed and total weight of seeds), increased carbon metabolism, increased carbohydrate (e.g., starch, sugars, cellulose), amino acid, and/or lipid production, early bolting, and also can include combinations of the foregoing, when compared to a wild-type plant of the same species cultivated under the same conditions.

5.1 GROWTH-PROMOTING PHOSPHATASES AND KINASES

Provided herein are phosphatases and kinases that promote plant growth and/or yield. In one embodiment, the growth-promoting phosphatase is NG6, and the growth-promoting kinases are selected from NG6, NG21, NG24, NG28, and NG32. In certain specific embodiments, the growth-promoting phosphatases and kinases are derived from plant species including, but not limited to, *Arabidopsis*, rice, soybean, maize, and cotton.

In certain embodiments, the phosphatase gene that promotes plant growth and/or yield is an NG6 gene comprising a nucleic acid sequence selected from SEQ ID NO: 1, 3, 5, 7, 9 or 93. In certain embodiments, the phosphatase gene that promotes plant growth and/or yield comprises a nucleic acid sequence having at least 80%, 85%, 90%, 93%, 95%, 96%, 97%, 98% or 99% identity with SEQ ID NO: 1, 3, 5, 7, 9 or 93. In certain embodiments, the phosphatase gene that promotes plant growth and/or yield is a homologue, derivative, or variant of a nucleic acid molecule derives from a nucleic acid molecule having nucleic acid sequence comprising SEQ ID NO: 1, 3, 5, 7, 9 or 93.

In certain embodiments, the phosphatase gene that promotes plant growth and/or yield comprises a nucleic acid sequence having at least 80%, 85%, 90%, 93%, 95%, 96%, 97%, 98% or 99% identity with SEQ ID NO: 1, 3, 5, 7, 9 or 93. In certain embodiments, the phosphatase gene that promotes plant growth and/or yield comprises the nucleic acid sequence that encodes a protein that comprises one or more of the following conserved motifs: GIFRSGFP (SEQ ID NO:75), YLCPEPYP (SEQ ID NO:76), KEPFVXIP (SEQ ID NO:77), and HCXRGKHRTG (SEQ ID NO:78).

In certain embodiments, the phosphatase gene that promotes plant growth and/or yield is a homologue, derivative, or variant of a nucleic acid molecule that derives from nucleic acid molecule having nucleic acid sequences comprising SEQ ID NO: 1, 3, 5, 7, 9 or 93. In certain embodiments, the phosphatase gene that promotes plant growth and/or yield comprises one or more of the following conserved motifs: GIFRSGFP (SEQ ID NO:75), YLCPEPYP (SEQ ID NO:76), KEPFVXIP (SEQ ID NO:77), and HCXRGKHRTG (SEQ ID NO:78).

In certain embodiments, the kinase gene that promotes plant growth and/or yield is an NG21 gene comprising a nucleic acid sequence selected from SEQ ID NO: 11, 13, 15, 17, 19 or 95. In certain embodiments, the kinase gene that promotes plant growth and/or yield comprises a nucleic acid sequence having at least 65%, 70%, 75%, 80%, 85%, 90%, 93%, 95%, 96%, 97%, 98% or 99% identity with SEQ ID NO: 11, 13, 15, 17, 19 or 95. In certain embodiments, the kinase gene that promotes plant growth and/or yield is a homologue, derivative, or variant of a nucleic acid molecule that derives from nucleic acid molecule having nucleic acid sequence comprising SEQ ID NO: 11, 13, 15, 17, 19 or 95.

In certain embodiments, the kinase gene that promotes plant growth and/or yield comprises a nucleic acid sequence having at least 80%, 85%, 90%, 93%, 95%, 96%, 97%, 98% or 99% identity with SEQ ID NO: 11, 13, 15, 17, or 19 or 95. In certain embodiments, the kinase gene that promotes plant growth and/or yield comprises the nucleic acid sequence that encodes a protein that comprises one or more of the following conserved motifs: DNWDDA(D/E)GYY (SEQ ID NO:79), YRNHLCLVFESL (SEQ ID NO:80), VLHCDIKPDNMLVNE (SEQ ID NO:81), and TPYLVSRFYRXPEI (SEQ ID NO:82).

In certain embodiments, the kinase gene that promotes plant growth and/or yield is a homologue, derivative, or variant of a nucleic acid molecule that derives from nucleic acid molecule having nucleic acid sequences comprising SEQ ID NO: 11, 13, 15, 17, 19 or 95. In certain embodiments, the kinase gene that promotes plant growth and/or yield comprises one or more of the following conserved motifs: DNWDDA(D/E)GYY (SEQ ID NO:79), YRNHLCLVFESL (SEQ ID NO:80), VLHCDIKPDNMLVNE (SEQ ID NO:81), and TPYLVSRFYRXPEI (SEQ ID NO:82). In certain embodiments, the kinase gene that promotes plant growth and/or yield is an NG24 gene comprising a nucleic acid sequence selected from SEQ ID NO: 21, 23, 25, 27, 29 or 97. In certain embodiments, the kinase gene that promotes plant growth and/or yield comprises a nucleic acid sequence having at least 65%, 70%, 75%, 80%, 85%, 90%, 93%, 95%, 96%, 97%, 98% or 99% identity with SEQ ID NO: 21, 23, 25, 27, 29 or 97. In certain embodiments, the kinase gene that promotes plant growth and/or yield is a homologue, derivative, or variant of a nucleic acid molecule that derives from nucleic acid molecule having nucleic acid sequence comprising SEQ ID NO: 21, 23, 25, 27, 29 or 97.

In certain embodiments, the kinase gene that promotes plant growth and/or yield comprises a nucleic acid sequence having at least 80%, 85%, 90%, 93%, 95%, 96%, 97%, 98% or 99% identity with SEQ ID NO: 21, 23, 25, 27, 29 or 97. In certain embodiments, the kinase gene that promotes plant growth and/or yield comprises one or more of the following conserved motifs: VRHRDXKS (SEQ ID NO:83), GTLXGYLDP (SEQ ID NO:84), and DV(F/Y)S(F/Y)G(I/V)LLLEI (SEQ ID NO:85).

In certain embodiments, the kinase gene that promotes plant growth and/or yield is a homologue, derivative, or variant of a nucleic acid molecule that derives from nucleic acid molecule having nucleic acid sequence comprising SEQ ID NO: 21, 23, 25, 27, 29 or 97. In certain embodiments, the kinase gene that promotes plant growth and/or yield comprises one or more of the following conserved motifs: VRHRDXKS (SEQ ID NO:83), GTLXGYLDP (SEQ ID NO:84), and DV(F/Y)S(F/Y)G(UV)LLLEI (SEQ ID NO:85). In certain embodiments, the kinase gene that promotes plant growth and/or yield is an NG28 gene comprising a nucleic acid sequence selected from SEQ ID NO: 31, 33, 35, 37, 39 or 99. In certain embodiments, the NG24 kinase gene that promotes plant growth and/or yield comprises a nucleic acid sequence having at least 65%, 70%, 75%, 80%, 85%, 90%, 93%, 95%, 96%, 97%, 98% or 99% identity with SEQ ID NO: 31, 33, 35, 37, 39 or 99. In certain embodiments, the NG24 kinase gene that promotes plant growth and/or yield is a homologue, derivative, or variant of a nucleic acid molecule that derives from nucleic acid molecule having nucleic acid sequence comprising SEQ ID NO: 31, 33, 35, 37, 39 or 99.

In certain embodiments, the kinase gene that promotes plant growth and/or yield comprises a nucleic acid sequence having at least 80%, 85%, 90%, 93%, 95%, 96%, 97%, 98% or 99% identity with SEQ ID NO: 31, 33, 35, 37, 39 or 99. In certain embodiments, the kinase gene that promotes plant growth and/or yield comprises one or more of the following conserved motifs: RRHKIALG (SEQ ID NO:86), Y(K/R)APEL (SEQ ID NO:87), and DVYAFGILLLE (SEQ ID NO:88).

In certain embodiments, the kinase gene that promotes plant growth and/or yield is a homologue, derivative, or variant of a nucleic acid molecule that derives from nucleic acid molecule having nucleic acid sequence comprising SEQ ID NO: 31, 33, 35, 37, 39 or 99. In certain embodiments, the kinase gene that promotes plant growth and/or yield comprises one or more of the following conserved motifs: RRHKIALG (SEQ ID NO:86), Y(K/R)APEL (SEQ ID NO:87), and DVYAFGILLLE (SEQ ID NO:88).

In certain embodiments, the kinase gene that promotes plant growth and/or yield is an NG32 gene comprising a nucleic acid sequence selected from SEQ ID NO: 41, 43, 45, 47, 49 or 101. In certain embodiments, the kinase gene that promotes plant growth and/or yield comprises a nucleic acid sequence having at least 65%, 70%, 75%, 80%, 85%, 90%, 93%, 95%, 96%, 97%, 98% or 99% identity with SEQ ID NO: 41, 43, 45, 47, 49 or 101. In certain embodiments, the kinase gene that promotes plant growth and/or yield is a homologue, derivative, or variant of a nucleic acid molecule that derives from nucleic acid molecule having nucleic acid sequence comprising SEQ ID NO: 41, 43, 45, 47, 49 or 101.

In certain embodiments, the kinase gene that promotes plant growth and/or yield comprises a nucleic acid sequence having at least 80%, 85%, 90%, 93%, 95%, 96%, 97%, 98% or 99% identity with SEQ ID NO: 41, 43, 45, 47, 49 or 101. In certain embodiments, the kinase gene that promotes plant growth and/or yield comprises one or more of the following conserved motifs: CAXDDERG (SEQ ID NO:89), AKLSDFGLAR (SEQ ID NO:90), YELITGR(R/K) (SEQ ID NO:91), and RPKMSEV (SEQ ID NO:92).

In certain embodiments, the kinase gene that promotes plant growth and/or yield is a homologue, derivative, or variant of a nucleic acid molecule that derives from nucleic acid molecule having nucleic acid sequence comprising SEQ ID NO: 41, 43, 45, 47, 49 or 101. In certain embodiments, the kinase gene that promotes plant growth and/or yield comprises one or more of the following conserved motifs: CAXDDERG (SEQ ID NO:89), AKLSDFGLAR (SEQ ID NO:90), YELITGR(R/K) (SEQ ID NO:91), and RPKMSEV (SEQ ID NO:92). In certain embodiments, the phosphatase or kinase gene that promotes plant growth and/or yield encodes a protein selected from SEQ ID NO: 2, 4, 6, 8, 10, 12, 14, 16, 18, 20, 22, 24, 26, 28, 30, 32, 34, 36, 38, 40, 42, 44, 46, 48, 50, 94, 96, 98, 100 or 102. In certain embodiments, the phosphatase or kinase gene that promotes plant growth and/or yield encodes a protein having at least 65%, 70%, 75%, 80%, 85%, 90%, 93%, 95%, 96%, 97%, 98% or 99% identity with SEQ ID NO: 2, 4, 6, 8, 10, 12, 14, 16, 18, 20, 22, 24, 26, 28, 30, 32, 34, 36, 38, 40, 42, 44, 46, 48, 50, 94, 96, 98, 100 or 102. In certain embodiments, the phosphatase or kinase gene that promotes plant growth and/or yield encodes a protein that is a homologue, derivative, or variant of a protein derived from the amino acid molecule having the amino acid sequence selected from SEQ ID NO: 2, 4, 6, 8, 10, 12, 14, 16, 18, 20, 22, 24, 26, 28, 30, 32, 34, 36, 38, 40, 42, 44, 46, 48, 50, 94, 96, 98, 100 or 102.

In certain embodiments, the phosphatase gene that promotes plant growth and/or yield encodes an NG6 protein having at least 80%, 85%, 90%, 93%, 95%, 96%, 97%, 98% or 99% identity with SEQ ID NO: 2, 4, 6, 8, 10 or 94. In certain embodiments, the phosphatase gene that promotes plant growth and/or yield one or more of the following conserved motifs: GIFRSGFP (SEQ ID NO:75), YLCPEPYP (SEQ ID NO:76), KEPFVXIP (SEQ ID NO:77), and HCXRGKHRTG (SEQ ID NO:78).

In certain embodiments, the phosphatase gene that promotes plant growth and/or yield encodes an NG6 protein that is a homologue, derivative, or variant of a protein derived from the amino acid molecule having the amino acid sequence comprising SEQ ID NO: 2, 4, 6, 8, 10 or 94. In certain embodiments, the phosphatase gene that promotes plant growth and/or yield comprises one or more of the following conserved motifs: GIFRSGFP (SEQ ID NO:75), YLCPEPYP (SEQ ID NO:76), KEPFVXIP (SEQ ID NO:77), and HCXRGKHRTG (SEQ ID NO:78).

In certain embodiments, the kinase gene that promotes plant growth and/or yield encodes an NG 21 protein having at least 80%, 85%, 90%, 93%, 95%, 96%, 97%, 98% or 99% identity with SEQ ID NO: 12, 14, 16, 18, 20 or 96. In certain embodiments, the kinase gene that promotes plant growth and/or yield comprises one or more of the following conserved motifs: DNWDDA(D/E)GYY (SEQ ID NO:79), YRNHLCLVFESL (SEQ ID NO:80), VLHCDIKPDNMLVNE (SEQ ID NO:81), and TPYLVSRFYRXPEI (SEQ ID NO:82).

In certain embodiments, the kinase gene that promotes plant growth and/or yield encodes an NG21 protein that is a homologue, derivative, or variant of a protein derived from the amino acid molecule having the amino acid sequence selected from SEQ ID NO: 12, 14, 16, 18, 20 or 96. In certain embodiments, the kinase gene that promotes plant growth and/or yield comprises one or more of the following conserved motifs: DNWDDA(D/E)GYY (SEQ ID NO:79), YRNHLCLVFESL (SEQ ID NO:80), VLHCDIKPDNMLVNE (SEQ ID NO:81), and TPYLVSRFYRXPEI (SEQ ID NO:82).

In certain embodiments, the kinase gene that promotes plant growth and/or yield encodes an NG24 protein having at least 80%, 85%, 90%, 93%, 95%, 96%, 97%, 98% or 99% identity with SEQ ID NO: 22, 24, 26, 28, 30 or 98. In certain embodiments, the kinase gene that promotes plant growth and/or yield comprises one or more of the following conserved motifs: VRHRDXKS (SEQ ID NO:83), GTLXGYLDP (SEQ ID NO:84), and DV(F/Y)S(F/Y)G(I/V) LLLEI (SEQ ID NO:85).

In certain embodiments, the kinase gene that promotes plant growth and/or yield encodes an NG24 protein that is a homologue, derivative, or variant of a protein derived from the amino acid molecule having the amino acid sequence selected from SEQ ID NO: 22, 24, 26, 28, 30 or 98. In certain embodiments, the kinase gene that promotes plant growth and/or yield comprises one or more of the following conserved motifs: VRHRDXKS (SEQ ID NO:83), GTLXGYLDP (SEQ ID NO:84), and DV(F/Y)S(F/Y)G (UV)LLLEI (SEQ ID NO:85).

In certain embodiments, the kinase gene that promotes plant growth and/or yield encodes an NG28 protein having at least 80%, 85%, 90%, 93%, 95%, 96%, 97%, 98% or 99% identity with SEQ ID NO: 32, 34, 36, 38, 40 or 100. In certain embodiments, the kinase gene that promotes plant growth and/or yield comprises one or more of the following conserved motifs: RRHKIALG (SEQ ID NO:86), Y(K/R)APEL (SEQ ID NO:87), and DVYAFGILLLE (SEQ ID NO:88).

In certain embodiments, the kinase gene that promotes plant growth and/or yield encodes an NG28 protein that is a homologue, derivative, or variant of a protein derived from the amino acid molecule having the amino acid sequence selected from SEQ ID NO: 32, 34, 36, 38, 40 or 100, wherein the protein comprises one or more of the following conserved motifs: RRHKIALG (SEQ ID NO:86), Y(K/R)APEL (SEQ ID NO:87), and DVYAFGILLLE (SEQ ID NO:88).

In certain embodiments, the kinase gene that promotes plant growth and/or yield encodes an NG32 protein having at least 80%, 85%, 90%, 93%, 95%, 96%, 97%, 98% or 99% identity with SEQ ID NO: 42, 44, 46, 48, 50 or 102. In certain embodiments, the kinase gene that promotes plant growth and/or yield comprises one or more of the following conserved motifs: CAXDDERG (SEQ ID NO:89), AKLSDF-GLAR (SEQ ID NO:90), YELITGR(R/K) (SEQ ID NO:91), and RPKMSEV (SEQ ID NO:92).

In certain embodiments, the kinase gene that promotes plant growth and/or yield encodes an NG32 protein that is a homologue, derivative, or variant of a protein derived from the amino acid molecule having the amino acid sequence selected from SEQ ID NO: 42, 44, 46, 48, 50 or 102, wherein the protein comprises one or more of the following conserved motifs: CAXDDERG (SEQ ID NO:89), AKLSDFGLAR (SEQ ID NO:90), YELITGR(R/K) (SEQ ID NO:91), and RPKMSEV (SEQ ID NO:92).

5.2 PRODUCTION OF TRANSGENIC PLANTS WITH ENHANCED GROWTH AND/OR YIELD

Another aspect of the present invention provides methods of producing plants with enhanced growth and/or yield. In one embodiment, the method comprises: transforming a plant or plant cell with a nucleic acid molecule comprising a plant kinase and/or phosphatase gene of the present invention. In one embodiment, the method comprises overexpressing said kinase and/or phosphatase gene in the plant or plant cell. In one embodiment, the present invention further comprises: regenerating, from said transformed plant or plant cell, a plant having enhanced growth and/or yield.

The term "overexpressing," "overexpression," or any of the grammatical variations thereof (e.g., over-expressing, over-expression) refers to an increase in the level of expression of a gene, or the level of a protein product encoded by a gene, wherein such increase is at least 5%, 10%, 15%, 20%, 25%, 30%, 35%, 40%, 50%, 60%, 70%, 80%, 90%, 100%, 150%, or 200%, when compared to cells of the same type in a wild-type plant of the same species cultivated under the same conditions.

In one embodiment, the method further comprises: transforming a plant or a plant cell with a nucleic acid molecule comprising an AtPAP2 gene. In certain embodiments, the method comprises overexpressing the AtPAP2 gene in the plant or plant cell. In one embodiment, the AtPAP2 gene comprises SEQ ID NO: 73. In certain embodiments, the AtPAP2 gene comprises a nucleic acid molecule having a nucleic acid molecule having sequence having at least 65%, 70%, 75%, 80%, 85%, 90%, 93%, 95%, 96%, 97%, 98%, or 99% identity with SEQ ID NO: 73.

In one embodiment, the method further comprises: transforming a plant or a plant cell with a nucleic acid molecule encoding AtPAP2 phosphatase. In certain embodiment, the method comprises overexpressing the nucleic acid molecule encoding AtPAP2 phosphatase in the plant or plant cell. In one embodiment, AtPAP2 phosphatase comprises SEQ ID NO: 74. In certain embodiments, AtPAP2 phosphatase comprises an amino acid molecule having an amino acid nucleic acid sequence having at least 65%, 70%, 75%, 80%, 85%, 90%, 93%, 95%, 96%, 97%, 98%, or 99% identity with SEQ ID NO: 74.

Provided herein are transgenic plants with enhanced growth and/or yield. In certain embodiments, the transgenic plant comprises a nucleic acid molecule having a nucleic acid sequence selected from SEQ ID NO: 1, 3, 5, 7, 9, 11, 13, 15, 17, 19, 21, 23, 25, 27, 29, 31, 33, 35, 37, 39, 41, 43, 45, 47, 49, 93, 95, 97, 99 or 101. In certain embodiments, the nucleic acid molecule is overexpressed in the transgenic plant when compared to a wild-type plant of the same species cultivated under the same conditions. In certain embodiments, the transgenic plant comprises a nucleic acid molecule having a nucleic acid sequence that is at least 65%, 70%, 75%, 80%, 85%, 90%, 93%, 95%, 96%, 97%, 98% or 99% identity with SEQ ID NO: 1, 3, 5, 7, 9, 11, 13, 15, 17, 19, 21, 23, 25, 27, 29, 31, 33, 35, 37, 39, 41, 43, 45, 47, 49, 93, 95, 97, 99 or 101. In certain embodiments, the nucleic acid molecule is overexpressed in the transgenic plant when compared to a wild-type plant of the same species cultivated under the same conditions. In certain embodiments, the transgenic plant comprises a nucleic acid molecule that is a homologue, derivative, or variant of a nucleic acid molecule derived from the nucleic acid molecule having a nucleic acid sequence selected from SEQ ID NO: 1, 3, 5, 7, 9, 11, 13, 15, 17, 19, 21, 23, 25, 27, 29, 31, 33, 35, 37, 39, 41, 43, 45, 47, 49, 93, 95, 97, 99 or 101. In certain embodiments, the nucleic acid molecule is overexpressed in the transgenic plant when compared to a wild-type plant of the same species cultivated under the same conditions.

In certain embodiments, the transgenic plant comprises a nucleic acid that encodes a protein having an amino acid sequence selected from SEQ ID NO: 2, 4, 6, 8, 10, 12, 14, 16, 18, 20, 22, 24, 26, 28, 30, 32, 34, 36, 38, 40, 42, 44, 46, 48, 50, 94, 96, 98, 100 or 102. In certain embodiments, the nucleic acid molecule is overexpressed in the transgenic plant when compared to a wild-type plant of the same species cultivated under the same conditions. In certain embodiments, the transgenic plant comprises a nucleic acid that encodes a protein having an amino acid sequence that is at least 65%, 70%, 75%, 80%, 85%, 90%, 93%, 95%, 96%, 97%, 98% or 99% identity with SEQ ID NO: 2, 4, 6, 8, 10, 12, 14, 16, 18, 20, 22, 24, 26, 28, 30, 32, 34, 36, 38, 40, 42, 44, 46, 48, 50, 94, 96, 98, 100 or 102. In certain embodiments, the nucleic acid molecule is overexpressed in the transgenic plant when compared to a wild-type plant of the same species cultivated under the same conditions. In certain embodiments, the transgenic plant comprises a nucleic acid that encodes a protein that is a homologue, derivative, or variant of a protein derived from the peptide having an amino acid sequence selected from SEQ ID NO: 2, 4, 6, 8, 10, 12, 14, 16, 18, 20, 22, 24, 26, 28, 30, 32, 34, 36, 38, 40, 42, 44, 46, 48, 50, 94, 96, 98, 100 or 102. In certain embodiments, the nucleic acid molecule is overexpressed in the transgenic plant when compared to a wild-type plant of the same species cultivated under the same conditions.

In certain embodiments, the transgenic plant comprises a protein having an amino acid sequence selected from SEQ ID NO: 2, 4, 6, 8, 10, 12, 14, 16, 18, 20, 22, 24, 26, 28, 30, 32, 34, 36, 38, 40, 42, 44, 46, 48, 50, 94, 96, 98, 100 or 102. In certain embodiments, the level of the protein in the transgenic plant is higher than that of a wild-type plant of the same species cultivated under the same conditions. In certain embodiments, the transgenic plant comprises a protein having an amino acid sequence that is at least 65%, 70%, 75%, 80%, 85%, 90%, 93%, 95%, 96%, 97%, 98% or 99% identity with SEQ ID NO: 2, 4, 6, 8, 10, 12, 14, 16, 18, 20, 22, 24, 26, 28, 30, 32, 34, 36, 38, 40, 42, 44, 46, 48, 50, 94, 96, 98, 100 or 102. In certain embodiments, the level of the protein in the transgenic plant is higher than that of a wild-type plant of the same species cultivated under the same conditions. In certain embodiments, the transgenic plant comprises a protein that is a homologue, derivative, or variant of a protein derived from the peptide having an amino acid and sequence selected from SEQ ID NO: 2, 4, 6, 8, 10, 12, 14, 16, 18, 20, 22, 24, 26, 28, 30, 32, 34, 36, 38, 40, 42, 44, 46, 48, 50, 94, 96, 98, 100 or 102. In certain embodiments, the level of the protein in the transgenic plant is higher than that of a wild-type plant of the same species cultivated under the same conditions.

In addition, the present invention provides transgenic plant cells transformed with a nucleic acid molecule of the present invention. In one embodiment, the invention provides transgenic plant cells comprising a kinase or phosphatase nucleic acid molecule of the invention. In certain embodiments, the nucleic acid molecule is overexpressed in the transgenic plant cells when compared to plant cells of the same type in a wild-type plant of the same species cultivated under the same conditions. In another embodiment, the invention provides transgenic plant cells comprising a kinase or phosphatase protein of the invention, wherein the level of said protein in the transgenic plant cells is higher (e.g., at least 5%, 10%, 15%, 20%, 25%, 30%, 35%, 40%, 50%, 60%, 70%, 80%, 90%, 100%, 150%, or 200% higher) than that of plant cells of the same type in a wild-type plant of the same species cultivated under the same conditions.

In certain embodiments, the transgenic plant comprises a nucleic acid molecule encoding a phosphatase having an amino acid sequence selected from SEQ ID NO: 2, 4, 6, 8, 10, or 94 and/or a kinase selected from SEQ ID NO: 12, 14, 16, 18, 20, 22, 24, 26, 28, 30, 32, 34, 36, 38, 40, 42, 44, 46, 48, 50, 96, 98, 100 or 102. In another embodiment, the transgenic plant comprises a nucleic acid molecule encoding a phosphatase having an amino acid sequence selected from SEQ ID NO: 2, 4, 6, 8, 10, or 94 and/or a kinase selected from SEQ ID NO: 12, 14, 16, 18, 20, 22, 24, 26, 28, 30, 32, 34, 36, 38, 40, 42, 44, 46, 48, 50, 96, 98, 100 or 102. In certain embodiment, all or a portion, particularly an N-terminal portion, of amino acid residues 1 to 80, preferably all or a portion of amino acid residues 1 to 30, are replaced by a heterologous plant signal peptide by genetic engineering. In such a transgenic plant, the phosphatases or kinases are directed to various organelles/compartments of the cells.

In certain embodiments, the present invention provides chimeric gene constructs for genetic modification of plants to increase growth rate and to improve yield. In a specific embodiment, the chimeric gene constructs comprise a nucleic acid molecule having the nucleic acid sequence of SEQ ID NO: 1, 3, 5, 7, 9, 11, 13, 15, 17, 19, 21, 23, 25, 27, 29, 31, 33, 35, 37, 39, 41, 43, 45, 47, 49, 93, 95, 97, 99 or 101. In another specific embodiment, the chimeric gene constructs comprise a sequence that hybridizes under stringent conditions to a nucleic acid molecule comprising a nucleic acid sequence of SEQ ID NO: 1, 3, 5, 7, 9, 11, 13, 15, 17, 19, 21, 23, 25, 27, 29, 31, 33, 35, 37, 39, 41, 43, 45, 47, 49, 93, 95, 97, 99 or 101, or a complement thereof, wherein the nucleic acid sequence encodes a protein or a polypeptide that exhibits at least one structural and/or functional feature of the polypeptides and enhances plant growth and/or yield.

Figure 3:
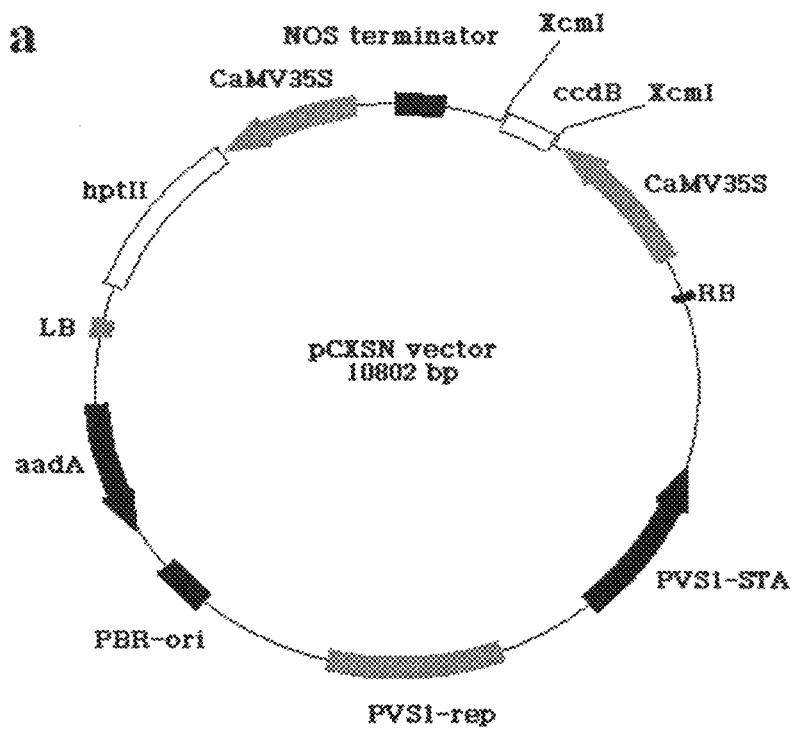
FIG. 3 shows a schematic diagram of the expression vector pCXSN. (a). The cDNAs of the NG genes were cloned into the pCXSN vector at the XcmI sites to create the overexpression vectors. (b) shows an exemplified overexpression vector pCXSN-NG6.
Figure 3:
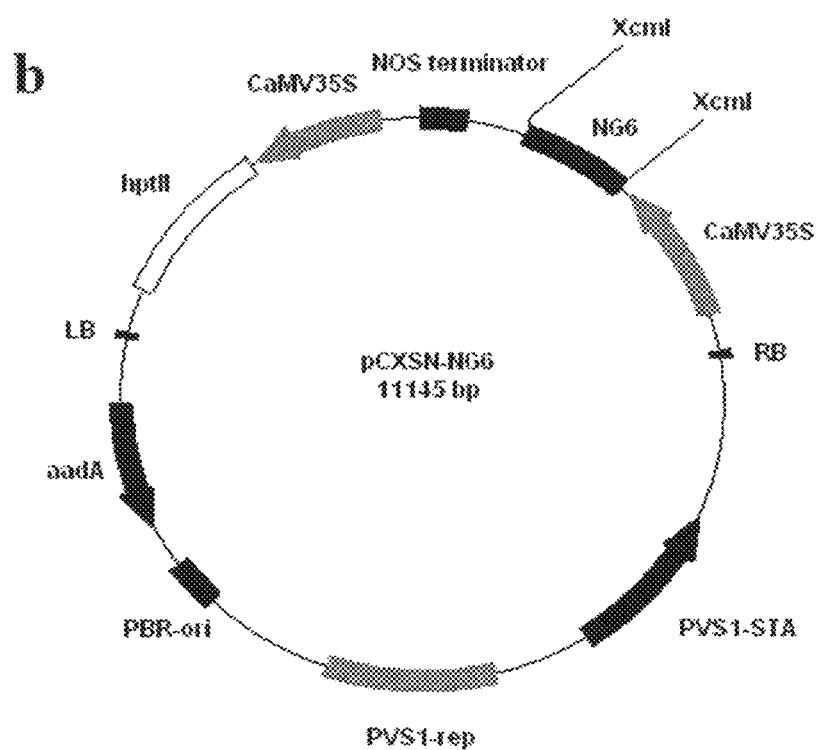

The phosphatase or kinase-coding sequence is operatively linked to upstream and downstream regulatory components, preferably heterologous to the phosphatase or kinase sequence, such as for example, CMV 35S promoter, which acts to cause expression of the gene (production of the enzyme) in plant cells (see FIG. 3). Preferably, when a construct comprising a gene encoding a phosphatase or kinase of the present invention is introduced into plant cells by a conventional transformation method, such as microparticle bombardment, *Agrobacterium* infection, or microinjection, the gene is expressed in the cells under the control of the regulatory sequences. The expressed phosphatase interacts with the biosynthetic machinery that is naturally present in the plant cells to alter the carbon metabolism. By altering the carbon metabolism, the method of the present invention promotes the growth rate of the plant, resulting in faster growth rate and higher yield. As a result, the time required for the maturation of the plant and the time required for flowering is shortened. Also provided are methods for increasing growth rate and yield of plants, comprising the step of inserting into such plant cells, or cells of such whole plants, a chimeric gene construct.

In one specific embodiment, *Arabidopsis* is genetically modified by introducing an overexpression construct comprising nucleic acid molecules encoding a growth-promoting phosphatase or kinase of the present invention.

In an embodiment, the growth-promoting phosphatase and kinase genes are derived from *Arabidopsis*. As shown in the examples, transgenic *Arabidopsis* plants with over-expression of NG6, NG21, NG24, NG28, and/or NG32 have enhanced growth and/or yield, when compared to wild-type *Arabidopsis* plants (see Table 5, and FIGS. 5 and 6).

In one embodiment, a transgenic plant overexpressing a nucleic acid comprises the sequence of SEQ ID NO: 1, 3, 5, 7, 9, 11, 13, 15, 17, 19, 21, 23, 25, 27, 29, 31, 33, 35, 37, 39, 41, 43, 45, 47, 49, 93, 95, 97, 99 or 101 or homologues thereof, wherein the nucleic acid molecule encodes polypeptides or proteins of the invention.

5.3 HOMOLOGUES, DERIVATIVES, AND VARIANTS OF KINASES AND PHOSPHATASES

The present invention also provides homologues, derivatives, and variants of kinases and phosphatases of the present invention; nucleic acid molecules encoding the polypeptides and homologues, derivatives, and variants; vectors, plant cells and transgenic plants comprising these nucleic acid molecules; and uses thereof for promoting plant growth and/or yield. The homologues, derivatives and variants of kinases and phosphatases are derived from the wild-type kinases and phosphatases, respectively. The methods of deriving the homologues, derivatives and variants are well known in the art which include routine conventional techniques of chemical modifications of amino acid residues or using molecular biology and recombinant DNA manipulation and production. Such techniques are available to the skilled artisan in laboratory manuals such as Sambrook and Russell, Molecular cloning: A Laboratory Manual, 3$^{rd}$ edition, Cold Spring Harbor Laboratory Press, Cold Spring Harbor, N.Y. (2001).

In one embodiment, a homologue of the nucleic acid or polypeptide molecule of the present invention includes: (i) a polypeptide with at least about 65%, at least about 70%, at least about 80%, at least about 90%, or at least about 98% sequence identity of the polypeptide of the invention; (ii) a polypeptide encoded by a nucleotide sequence that is at least about 65%, at least about 70%, at least about 80%, at least about 90%, or at least about 98% identical to one or more of the nucleotide sequences encoding a polypeptide of the invention, or a fragment thereof; (iii) a polypeptide encoded by a nucleotide sequence that hybridizes, under stringent conditions, to a nucleotide sequence of the present invention; (iv) a polypeptide having an amino acid sequence that is at least about 65%, at least about 70%, at least about 80%, at least about 90%, or at least about 98% identical to a polypeptide of the present invention, and wherein the polypeptide of the invention is conservatively substituted; (v) a nucleic acid sequence encoding an amino acid sequence that is at least about 70%, at least about 80%, at least about 90%, or at least about 98% identical to a polypeptide of the present invention and wherein the polypeptide of the invention is conservatively substituted; and (vi) a fragment of a polypeptide described in (i) through (iv), wherein the polypeptide fragment has at least 175, 200, 225, 250, 275, 300, 325, 350, 375, 400, 450, 500, 550, 600, 650, 700, or 750 contiguous amino acid residues of a polypeptide of the invention.

In one embodiment, a homologue polypeptide has an amino acid sequence that is at least about 65%, at least about 70%, at least about 80%, at least about 90%, at least about 95%, or at least about 98% identical to a kinase or phosphatase of the present invention. In one embodiment, the homologue polypeptide is obtained by conservative substitution.

In one aspect, the homologues derivatives and variants are derived from the wild type kinase and phosphatase by substitution, deletion, insertion of one or more nucleic acid in a nucleic acid molecule or one or more amino acid residues in an amino acid molecule. The term "derived" as used herein includes the modifications of a wild type nucleic acid molecule or amino acid molecule as described below. For example, non-natural amino acids can be substituted for the amino acids of the kinases and phosphatases so long as the kinases and phosphatases having the substituted amino acids retain substantially the same functional activity as the kinases and phosphatases in which amino acids have not been substituted. Those having skill in the art will recognize that mutations can be made to polynucleotides encoding protein and peptides, or complementary thereto, and that such mutations do not cause structural changes that affect functionality.

Conservative substitutions whereby a modified protein or polypeptide of the present invention having an amino acid of one class is replaced with another amino acid of the same class fall within the scope of the subject invention so long as the modified protein or polypeptide having the substitution still retains substantially the same functional activity as the protein or polypeptide that does not have the substitution. For instance, amino acid residue of any of the following 11 groups may be conservatively substituted with another amino acid of the same group: (1) acidic (negatively charged) amino acids, such as aspartic acid and glutamic acid; (2) basic (positively charged) amino acids, such as arginine, histidine, and lysine; (3) neutral polar amino acids, such as glycine, serine, threonine, cysteine, tyrosine, asparagine, and glutamine; (4) neutral nonpolar (hydrophobic) amino acids, such as alanine, leucine, isoleucine, valine, proline, phenylalanine, tryptophan, and methionine; (5) amino acids having aliphatic side chains, such as glycine, alanine, valine, leucine, and isoleucine; (6) amino acids having aliphatic-hydroxyl side chains, such as serine and threonine; (7) amino acids having amide-containing side chains, such as asparagine and glutamine; (8) amino acids having aromatic side chains, such as phenylalanine, tyrosine, and tryptophan; (9) amino acids having basic side chains, such as lysine, arginine, and histidine; (10) amino acids having sulfur-containing side chains, such as cysteine and methionine; and (11) amino acids having similar geometry and hydrogen bonding patterns, such as aspartic acid, asparagine, glutamic acid and glutamine.

Examples of non-natural amino acids include, but are not limited to, ornithine, citrulline, hydroxyproline, homoserine, phenylglycine, taurine, iodotyrosine, 2,4-diaminobutyric acid, α-amino isobutyric acid, 4-aminobutyric acid, 2-amino butyric acid, γ-amino butyric acid, ε-amino hexanoic acid, 6-amino hexanoic acid, 2-amino isobutyric acid, 3-amino propionic acid, norleucine, norvaline, sarcosine, homocitrulline, cysteic acid, τ-butylglycine, τ-butylalanine, phenylglycine, cyclohexylalanine, β-alanine, fluoro-amino acids, designer amino acids such as β-methyl amino acids, C-methyl amino acids, N-methyl amino acids, and amino acid analogues in general. Non-natural amino acids also include amino acids having derivatized side groups. Furthermore, any of the amino acids in the protein can be of the D (dextrorotary) form or L (levorotary) form.

The structure of a polypeptide can be determined by methods known to those skilled in the art, including but not limited to, X-ray crystallography, nuclear magnetic resonance, and crystallographic electron microscopy. A sequence having sequence homology can be made using standard molecular biology techniques, including site-directed mutagenesis and by insertion or deletion of sequences.

In one aspect, the homologues, derivatives and variants are derived from the wild type kinase and phosphatase. In certain embodiments, provided herein are derivatives of the disclosed polypeptides. For example, but not by way of limitation, derivatives may include peptides or proteins that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques including, but not limited to, specific chemical cleavage, acetylation, formylation, etc. Additionally, the derivative may contain one or more non-classical amino acids. The subject invention also concerns variants of the polynucleotides of the present invention. Variant sequences include those sequences wherein one or more nucleotides of the sequence have been substituted, deleted, and/or inserted.

The nucleotides that can be substituted for natural nucleotides of DNA have a base moiety that can include, but is not limited to, inosine, 5-fluorouracil, 5-bromouracil, hypoxanthine, 1-methylguanine, 5-methylcytosine, and tritylated bases. The sugar moiety of the nucleotide in a sequence can also be modified and includes, but is not limited to, arabinose, xylulose, and hexose. In addition, the adenine, cytosine, guanine, thymine, and uracil bases of the nucleotides can be modified with acetyl, methyl, and/or thio groups. Sequences containing nucleotide substitutions, deletions, and/or insertions can be prepared and tested using standard techniques known in the art.

Unless otherwise specified, as used herein percent sequence identity and/or similarity of two sequences can be determined using the algorithm of Karlin and Altschul (1990), modified as in Karlin and Altschul (1993). Such an algorithm is incorporated into the NBLAST and XBLAST programs of Altschul et al. (1990). BLAST searches can be performed with the NBLAST program, score=100, wordlength=12, to obtain sequences with the desired percent sequence identity. To obtain gapped alignments for comparison purposes, Gapped BLAST can be used as described in Altschul et al. (1997). When utilizing BLAST and Gapped BLAST programs, the default parameters of the respective programs (NBLAST and XBLAST) can be used. See NCBI/NIH website.

The subject invention also contemplates those polynucleotide molecules having sequences which are sufficiently homologous with the polynucleotide sequences exemplified herein so as to permit hybridization with that sequence under standard stringent conditions and standard methods (Maniatis et al., 1982).

In one embodiment, the present invention further provides isolated nucleic acid molecules that comprise, or consist of, at least about 550, at least about 600, at least about 650, at least about 700, at least about 750, at least about 800, at least about 850, at least about 900, at least about 950, at least about 1000, at least about 1050, at least about 1100, at least about 1150, at least about 1200, at least about 1250, at least about 1300, or at least about 1350 contiguous nucleotides of a nucleic acid molecule of the present invention.

In another embodiment, an isolated nucleic acid molecule encodes a variant of a polypeptide whose amino acid sequence has been modified by genetic engineering so that biological activities of the polypeptides are either enhanced or reduced, or the local structures thereof are changed without significantly altering the biological activities. Amino acid modifications can be made by methods known in the art.

In one embodiment, the present invention embodies isolated nucleic acid molecules that hybridize, under stringent conditions, to nucleic acid molecules having the nucleic acid sequence comprising SEQ ID NO: 1, 3, 5, 7, 9, 11, 13, 15, 17, 19, 21, 23, 25, 27, 29, 31, 33, 35, 37, 39, 41, 43, 45, 47, 49, 93, 95, 97, 99 or 101, or homologues thereof. In certain embodiments, the nucleic acid molecules encode proteins or polypeptides that exhibit at least one structural and/or functional feature of the polypeptides of the invention (e.g. enhance plant growth and/or yield).

A further embodiment includes methods for preparing a polypeptide as provided herein by recombinant DNA technology. In one embodiment, the preparation method comprises culturing host cells containing a recombinant expression vector encoding a polypeptide as provided herein, or a nucleotide sequence encoding a polypeptide as provided herein operably linked to a heterologous promoter, and producing the polypeptide as provided herein.

5.4 VECTORS AND EXPRESSION CONSTRUCTS

Another embodiment includes nucleic acid molecules suitable for use as primers or hybridization probes for the detection of nucleic acids encoding a phosphatase or kinase polypeptide as provided herein or other sequences.

Yet another embodiment includes vectors, e.g., recombinant expression vectors, comprising a nucleic acid molecule as provided herein. Furthermore, host cells containing such a vector or engineered to contain and/or express a nucleic acid molecule as provided herein and host cells containing a nucleotide sequence as provided herein operably linked to a heterologous promoter are disclosed.

As used herein, the term "expression construct" refers to a combination of nucleic acid sequences that provides for transcription of an operably linked nucleic acid sequence. In general, operably linked components are in contiguous relation.

Expression constructs of the invention will also generally include regulatory elements that are functional in the intended host cell in which the expression construct is to be expressed. Regulatory elements include promoters, transcription termination sequences, translation termination sequences, enhancers, and polyadenylation elements.

An expression construct as provided herein can comprise a promoter sequence operably linked to a polynucleotide sequence encoding a peptide. Promoters can be incorporated into a polynucleotide using standard techniques known in the art. Multiple copies of promoters or multiple promoters can be used in an expression construct. In a preferred embodiment, a promoter can be positioned about the same distance from the transcription start site as it is from the transcription start site in its natural genetic environment. Some variation in this distance is permitted without substantial decrease in promoter activity. A transcription start site is typically included in the expression construct.

Unique restriction enzyme sites can be included at the 5' and 3' ends of the expression construct to allow for insertion into a polynucleotide vector. As used herein, the term "vector" refers to any genetic element, including for example, plasmids, cosmids, chromosomes, phage, virus, and the like, which is capable of replication when associated with proper control elements and which can transfer polynucleotide sequences between cells. Vectors contain a nucleotide sequence that permits the vector to replicate in a selected host cell.

The term "operably linked," as used herein, refers to when transcription under the control of the "operably linked" promoter produces a functional messenger RNA, translation of which results in the production of the polypeptide encoded by the DNA operably linked to the promoter.

5.5 FUSION PROTEINS

Also provided herein are fusion proteins. In one embodiment, the polypeptides as provided herein, or fragments thereof, are recombinantly fused or chemically conjugated (e.g., covalent and non-covalent conjugations) to heterologous polypeptides (i.e., an unrelated polypeptide or portion thereof, preferably at least 10, at least 20, at least 30, at least 40, at least 50, at least 60, at least 70, at least 80, at least 90 or at least 100 amino acids of the polypeptide) to generate fusion proteins. The fusion can be direct, or may occur through linker sequences.

In one embodiment, the fusion protein comprises a polypeptide fused to a heterologous signal sequence at its N-terminus. For example, the signal sequence naturally found in the polypeptide can be replaced by a signal sequence that is derived from a heterologous origin. Various signal sequences are commercially available.

In another embodiment, a polypeptide can be fused to tag sequences, e.g., a hexa-histidine peptide, among others, many of which are commercially available. As described in Gentz et al., 1989, *Proc. Natl. Acad. Sci. USA*, 86:821-824, for instance, hexa-histidine provides for convenient purification of the fusion protein. Other examples of peptide tag include the hemagglutinin "HA" tag, which corresponds to an epitope derived from the influenza hemagglutinin protein (Wilson et al., 1984, *Cell,* 37:767), and the "flag" tag (Knappik et al., 1994, *Biotechniques,* 17(4):754-761). These tags are useful for purification of recombinantly produced polypeptides.

Fusion proteins can be produced by standard recombinant DNA techniques or by protein synthetic techniques, e.g., by use of a DNA synthesizer. For example, a nucleic acid molecule encoding a fusion protein can be synthesized by conventional techniques including, for example, automated DNA synthesizers. Alternatively, PCR amplification of gene fragments can be carried out using anchor primers, which give rise to complementary overhangs between two consecutive gene fragments that can subsequently be annealed and reamplified to generate a chimeric gene sequence (see, e.g., *Current Protocols in Molecular Biology*, Ausubel et al., eds., John Wiley & Sons, 1992).

The nucleotide sequence encoding a fusion protein can be inserted into an appropriate expression vector, i.e., a vector that contains the necessary elements for the transcription and translation of the inserted protein-coding sequence. In a specific embodiment, the expression of a fusion protein is regulated by an inducible promoter.

In another embodiment, the present invention provides methods for detecting the presence, activity or expression of a polypeptide of the invention or similar polypeptide in a biological material, such as cells, or culture media. The increased or decreased activity or expression of the polypeptide in a sample relative to a control sample can be determined by contacting the biological material with an agent that can detect directly or indirectly the presence, activity or expression of the polypeptide. In a particular embodiment, such an agent is an antibody or a fragment thereof which immunospecifically binds to one of the disclosed polypeptides.

In a still another embodiment, a fusion protein comprising a bioactive molecule and one or more domains of a disclosed polypeptide or fragment thereof is provided. In particular, fusion proteins comprising a bioactive molecule recombinantly fused or chemically conjugated (including both covalent and non-covalent conjugations) to one or more domains of a disclosed polypeptide or fragments thereof.

5.6 PREPARATION OF TRANSGENIC PLANTS

Genetic engineering of plants can be achieved in several ways. The most common method is *Agrobacterium*-mediated transformation. In this method, *A. tumefaciens*, which naturally infects plants by inserting tumor-causing genes into a plant's genome, is genetically altered. Selected genes can be engineered into the T-DNA of the bacterial Ti (tumor-inducing) plasmid of *A. tumefaciens* in laboratory conditions so that they become integrated into the plant chromosomes when the T-DNA is transferred to the plant by the bacteria's own internal transfer mechanisms.

The only essential parts of the T-DNA are its two small (25 base pair) border repeats, at least one of which is needed for plant transformation. The bacterial genes encoding for plant hormones that promote tumor growth are excised from the T-DNA and replaced with a sequence of DNA that typically contains: a selectable marker (e.g. an antibiotic-resistance gene; usually kanamycin resistance), a restriction site—a site with a specific sequence of nucleotides where a restriction enzyme will cut the DNA, and the desired genes to be incorporated into the plant (B. Tinland, 1996. The integration of T-DNA into plant genomes. Trends in Plant Science 1, 178-184; D. Grierson (ed.) 1991. Plant Genetic Engineering. Blackie, Glasgow).

*Agrobacterium* can be added to plant protoplasts (plant cells with cell walls removed) in culture; the plant protoplasts then regenerate cell walls at which point non-transformed plants are killed with antibiotics for which the transformed plants have been given resistance genes. Plantlets are then regenerated from the surviving transformed cells using standard plant tissue culture techniques.

In an alternative technique, sterile disks or fragments of vegetative portions of plants are placed in liquid culture medium with *Agrobacterium*, and then hormones are used to induce rooting, thereby regenerating plantlets grown on selection media. Another technique for delivering genes is possible for some plants such as *Arabidopsis*, where the *Agrobacterium* or even "naked" DNA can be infused through the seed coat to cause transformation (Clough S J and Bent A F, 1998. Floral dip: a simplified method for *Agrobacterium*-mediated transformation of *Arabidopsis thaliana*. Plant J 16:735-43).

The biolistic method for genetic engineering of plants was developed more recently and is becoming more widely employed. In this method, very small particles (microprojectiles) of tungsten or gold coated with biologically active DNA are propelled at high-velocities into plant cells using an electrostatic pulse, air pressure, or gunpowder percussion. As the particles pass through the cell, the DNA dissolves and can then integrate into the genome of that cell and its progeny. This method can produce stable transformants (Christou, P., et al., 1988. Stable transformation of soybean callus by DNA-coated gold particles, *Plant Physiology* 87:671-674). The method can be practiced on whole plants and is particularly effective on meristematic tissue. It is also capable of delivering DNA either to the nucleus or into mitochondria (Johnston, S. A., et al., 1988. Mitochondrial transformation in yeast by bombardment with microprojectiles (Science 240, 1538-41) and chloroplasts (Svab, Z., et al., 1990, Stable transformation of plastids in higher plants, *Proc Natl Acad Sci. USA* 87, 8526-8530).

The electroporation method of plant genetic engineering has met with less success. In this technique, protoplasts in culture take up pure DNA when treated with certain membrane-active agents or with electroporation—a rapid pulse of high-voltage direct current. Once the DNA enters the protoplast, it can be integrated into the cells genome. Standard tissue culture techniques are then used to regenerate transgenic plants.

The microinjection method of plant genetic engineering is perhaps the most difficult. In this method, DNA is microinjected into target plant cells using very thin glass needles in a method similar to that used with animals. The technique is laborious, ineffective, and impractical for generating large numbers of transgenic plants.

It is within the ability of a skilled artisan to select known methods for producing genetically engineering plants, taking into account various factors such as the targeted plant species and which methods have been proven effective therein.

5.7 PREPARATION OF ANTIBODIES

In one aspect, provided herein are antibodies against the kinase and phosphatase. Antibodies which specifically recognize one of the described phosphatase polypeptides or fragments thereof can be used for detecting, screening, and isolating the polypeptide that is provided herein or fragments thereof, or similar sequences that encode similar enzymes from other organisms. For example, an antibody which immunospecifically binds a protein or protein fragments thereof can be used for various in vitro detection assays, including enzyme-linked immunosorbent assays (ELISA), radioimmunoassays, Western blot, etc., for the detection of the polypeptide that is provided herein or fragments, derivatives, homologues, or variants thereof, or similar molecules having the similar enzymatic activities as the phosphatase and/or kinase polypeptides.

Embodiments further provide antibodies that immunospecifically bind a polypeptide that is provided herein. Such antibodies include, but are not limited to, antibodies from various animals, humanized, chimeric, polyclonal, monoclonal, bi-specific, multi-specific, single chain antibodies, Fab fragments, F(ab')$_2$ fragments, disulfide-linked Fvs, fragments containing a VL or VH domain or a complementary determining region (CDR), wherein the antibody or antibody fragment immunospecifically binds to a polypeptide that is provided herein.

Antibodies specific for the described phosphatase polypeptides can be generated by any suitable method known in the art. Once an antibody molecule has been produced, it may then be purified by any method known in the art for purification of an immunoglobulin molecule, for example, by chromatography (e.g., ion exchange, affinity, particularly by affinity for the specific antigen after Protein A or Protein G purification, and sizing column chromatography), centrifugation, differential solubility, or by any other standard techniques for the purification of proteins. Further, the antibodies or fragments thereof may be fused to heterologous polypeptide sequences described herein or otherwise known in the art to facilitate purification.

Antibodies fused or conjugated to heterologous polypeptides may be used in in vitro immunoassays and in purification methods (e.g., affinity chromatography) well known in the art. See e.g., PCT publication Number WO 93/21232; EP 439,095; Naramura et al., 1994, *Immunol. Lett.* 39:91-99; U.S. Pat. No. 5,474,981; Gillies et al., 1992, PNAS 89:1428-1432; and Fell et al., 1991, *J. Immunol.* 146:2446-2452, which are incorporated herein by reference in their entireties.

Antibodies may also be attached to solid supports, which are particularly useful for immunoassays or purification of the described polypeptides or fragments, derivatives, homologues, or variants thereof, or similar molecules having the similar enzymatic activities as the polypeptide of the invention. Such solid supports include, but are not limited to, glass, cellulose, polyacrylamide, nylon, and polystyrene.

5.8 DETECTION ASSAYS

An exemplary method for detecting the presence or absence of an over-expressed phosphatase/kinase polypeptide or an inserted phosphatase/kinase-encoding nucleic acid in a biological sample involves obtaining a biological sample from various sources and contacting the sample with a compound or an agent capable of detecting a polypeptide or nucleic acid (e.g., mRNA, genomic DNA) such that the presence of a heterologous polypeptide or nucleic acid is detected in the sample.

An exemplary agent for detecting mRNA or genomic DNA encoding an inserted phosphatase polypeptide is a labeled nucleic acid probe capable of hybridizing to mRNA or genomic DNA encoding any of the described phosphatase and kinase polypeptides. The nucleic acid probe can be, for example, a full-length cDNA, such as the nucleic acid of SEQ ID NO: 1, 3, 5, 7, 9, 11, 13, 15, 17, 19, 21, 23, 25, 27, 29, 31, 33, 35, 37, 39, 41, 43, 45, 47, 49, 93, 95, 97, 99, 101 or a portion thereof, such as an oligonucleotide of at least one of at least about 15, at least about 20, at least about 25, at least about 30, at least about 50, at least about 100, at least about 250, at least about 500, or more nucleotides in length and sufficient to specifically hybridize under stringent conditions to a mRNA or genomic DNA encoding a polypeptide of the invention.

An exemplary agent for detecting an over-expressed phosphatase/kinase polypeptide is an antibody capable of binding to a phosphatase/kinase polypeptide product of an inserted gene, preferably an antibody with a detectable label. Antibodies can be polyclonal and monoclonal. An intact antibody, or a fragment thereof (e.g., Fab or F(ab')$_2$) can be used.

The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

The detection method can be used to detect mRNA, protein, or genomic DNA in a sample in vitro as well as in vivo. For example, in vitro techniques for detection of mRNA include Northern hybridizations and in situ hybridizations. In vitro techniques for detection of a heterologous polypeptide include enzyme linked immunosorbent assays (ELISAs), Western blots, immunoprecipitations and immunofluorescence. In vitro techniques for detection of genomic DNA include Southern hybridizations. Furthermore, in vivo techniques for detection of a heterologous polypeptide include introducing into a subject organism a labeled antibody directed against the polypeptide. For example, the antibody can be labeled with a radioactive marker whose presence and location in the subject organism can be detected by standard imaging techniques, including autoradiography.

In a specific embodiment, the methods further involve: 1) obtaining a control sample from a control subject, 2) contacting the control sample with a compound or agent capable of detecting an over-expressed polypeptide product, or the mRNA transcription product, or genomic DNA encoding an inserted phospatase gene, such that the presence of the polypeptide or mRNA or genomic DNA encoding the phosphatase polypeptide is detected in the sample, and 3) comparing the level of the phosphatase/kinase polypeptide or mRNA or genomic DNA encoding the polypeptide in a control sample with the level of the polypeptide or mRNA or genomic DNA encoding endogenous phosphatase polypeptides in the test sample.

5.9 APPLICATIONS OF TRANSGENIC PLANTS

The transgenic plants generated can have many useful applications, including in food, feed, biomass, biofuels (starch, cellulose, seed lipids) and wood pulp industry. The enhanced growth rate of the transgenic plants can provide additional carbon dioxide fixation per hectare of land per year, and, thus is useful for generating carbon credits.

6.0 EXAMPLES

Following are examples that illustrate embodiments for practicing the invention. These examples should not be construed as limiting. Unless otherwise noted, all percentages are by weight, all solvent mixture proportions are by volume, all temperatures are in Centigrade, and all pressure is at or near atmospheric pressure.

6.1 SCREENING OF GROW-PROMOTING NG GENES

Two independent AtPAP2 overexpression lines (OE7 and OE21, homozygous T3 plants), an AtPAP2 T-DNA mutant line that cannot express the full length AtPAP2, and the wild-type *Arabidopsis* (Col-0) were employed for microarray analysis. The AtPAP2 overexpression lines (OE7 and OE21, homozygous T3 plants), the AtPAP2 T-DNA mutant line, and the wild-type *Arabidopsis* (Col-0) line have been disclosed by the present inventor in U.S. patent application Ser. No. 12/640,674 (U.S. Patent Application Publication No. 2010/0159065), which is hereby incorporated by reference in its entirety.

Briefly, seeds were germinated on MS medium supplemented with 2% (w/v) sucrose, grew in a growth room under 12 hour-light/12 hour-dark cycle at 22° C. for 10 days, and were then transferred to soil and grew in a growth chamber under a 16-hour light (22° C.) and 8-hour dark (18° C.) cycle. Shoots of 20-day-old *Arabidopsis* (WT, T-DNA, OE7 and OE21) prior to bolting were collected in the middle of day (4 plants/line/tube, 3 biological triplicates/line, 3 tubes/line) and ground in liquid nitrogen. RNA extraction was performed with on-column DNase digestion according to the manufacturer's instruction (RNeasy Plant Mini Kit, Cat. No. 74904, Qiagen). Total RNA was dissolved in DEPC water and quantified by the Bioanalyzer 2100 (Agilent Technologies, Boblingen, Germany). Double strand DNA synthesis and Cy 3 labeling from three biological replicates were performed by NimbleGen Systems, Inc. (Madison, Wis.). Statistical analyses of normalized microarray data (RMA algorithm, quantile normalization) and drawing of scatter plots, heatmaps were performed using ArrayStar 3.0 (DNASTAR, Madison, Wis.). Identification of GO and classification were carried out using software available from TAIR database and KEGG pathway database. In all three replications, genes were considered to be significantly regulated if their fold change values were positively or negatively beyond 1.3 (p<0.05).

20-day-old plants did not show any differences in appearance so that any differences in gene expression between the lines were not due to difference in developmental stage or additional tissues (e.g. inflorescence). The transcripts levels of 30360 genes in shoots were determined using the *Arabidopsis* Genome NimbleGen chips. The average hybridization signals detected in each line were normalized from the log 2 average signal and compared with the signal strengths in the wild-type *Arabidopsis*.

Figure 1:
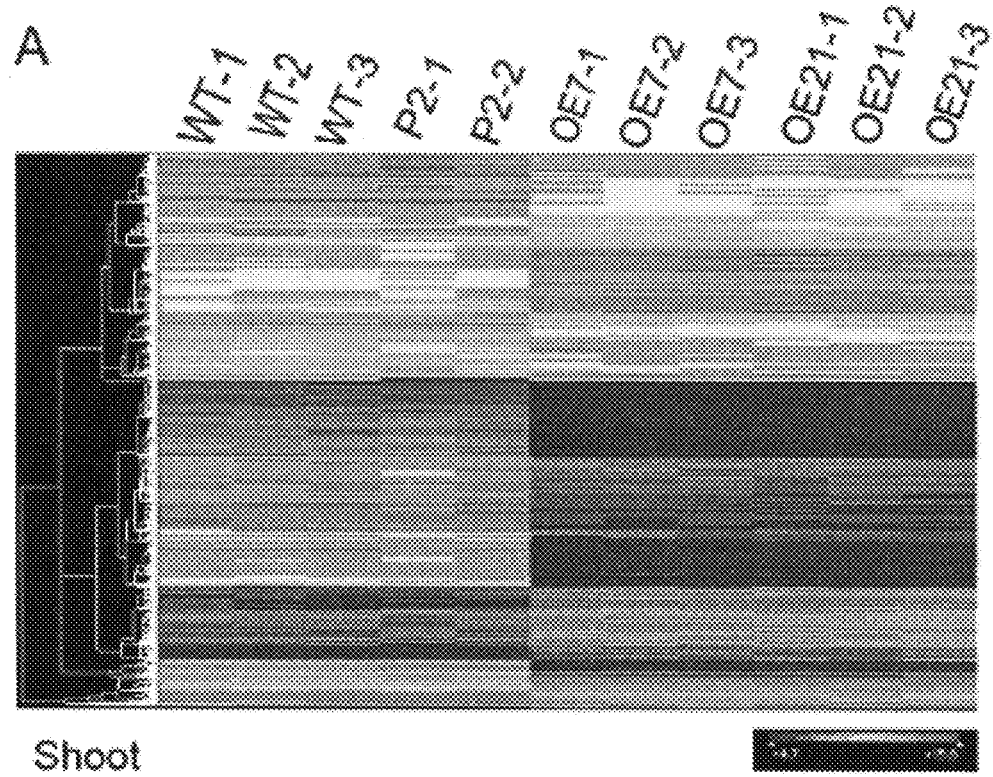
FIG. 1 shows a heat map of the microarray analysis of gene expression profile of *Arabidopsis* shoots, using three biological replicates for wild-type (WT), 2 biological replicates for AtPAP2 T-DNA line (P2), and 3 biological replicates for two independent AtPAP2 overexpression lines (OE7 and OE21).
Figure 2:
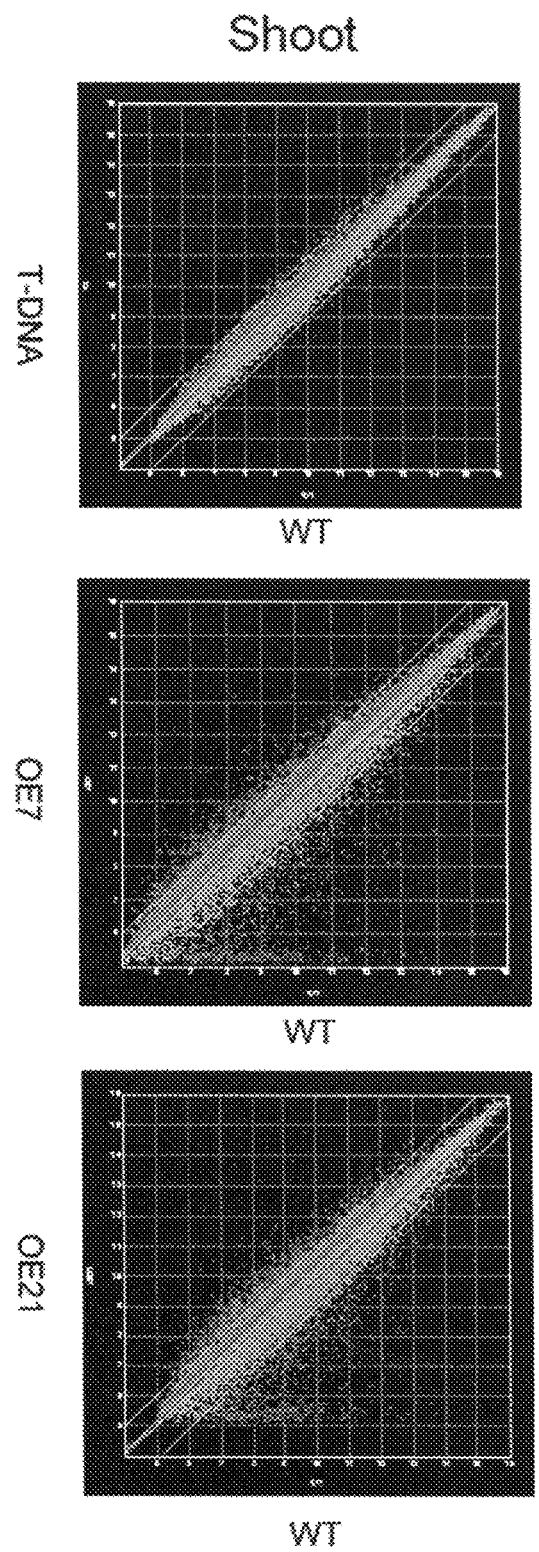
FIG. 2 shows scatter plots of the microarray analysis of gene expression profile of *Arabidopsis* shoots. The results showed that the expression profiles of the two independent AtPAP2 overexpression lines (OE7 and OE21) were significantly different from that of the wild-type (WT), whereas the expression profile of the AtPAP2 T-DNA (mutant) lines resembled closely that of the WT.

An overview of the expression data of OE7, OE21 and T-DNA plants versus wild-type control is presented as a heat map (FIG. 1) and scatter plots (FIG. 2) that show a linear bias in the graphs. Gene expression patterns in transgenic shoots are different comparative to their wild-type controls.

The data show that AtPAP2 overexpression altered expression levels of other genes, nearly half of which have not been characterized yet. AtPAP2 overexpression lines exhibit more dramatic changes in gene expression than the AtPAP2 T-DNA line.

Differentially expressed genes are identified using P-value<0.05 and fold change>1.3 as the cutoff, and the results show that the expression of about 6312, 7831, and 672 genes in the shoots of OE7, OE21 and T-DNA lines are significantly altered. An overall view of the altered genes in the heat map (FIG. 1) revealed that most genes were down-regulated in the fold change>=2.0. In addition, the fold change in expression levels is smaller in up-regulated genes than in down-regulated genes.

Based on the microarray data, 33 putative phosphatase and kinase genes were selected, and were introduced into *Arabidopsis* to produce overexpression lines. The results show that the overexpression of NG6, NG21, NG24, NG28 and NG32 in *Arabidopsis* promotes the growth of *Arabidopsis* and increases seed yield (see Example 2). The expression level of the five growth-promoting NG genes in the AtPAP2OE lines and T-DNA lines are shown in Table 1.

TABLE 1

Microarray data of the 5 growth-promoting genes in AtPAP2 overexpression lines (OE7, OE21), T-DNA line and wild type (WT) *Arabidopsis*.

| NG No. | AGI code | WT-Mean | T-DNA Mean | OE7 Mean | OE21 Mean | OE7/WT Fold | OE21/WT Fold | T-DNA/WT Fold | Gene Description |
|---|---|---|---|---|---|---|---|---|---|
| NG6 | AT1G05000 | 637 | 533 | 976 | 1131 | 1.52* | 1.78** | 0.83 | Protein phosphatase |
| NG21 | AT1G13350 | 2406 | 2151 | 3543 | 3441 | 1.47* | 1.43* | 0.89 | Protein kinase |
| NG24 | AT1G28390 | 778 | 710 | 1853 | 1915 | 2.37** | 2.42** | 0.91 | Protein kinase |
| NG28 | AT3G24660 | 2514 | 1839 | 3313 | 4422 | 1.32** | 1.74** | 0.73 | Protein kinase |
| NG32 | AT5G03320 | 1325 | 1063 | 1884 | 2053 | 1.43* | 1.56** | 0.80 | Protein kinase |

6.2 PRODUCTION OF NG OVEREXPRESSION LINES IN *ARABIDOPSIS*

To create transgenic NG gene overexpressing lines, the full length coding region of each NG gene's cDNA was amplified by PCR using the following primers (Table 2). The PCR products were inserted into the pCXSN vector with classical TA cloning method (FIG. 3).

TABLE 2

Primers used for to amplify the full CDS of the aimed NG genes

| | Gene name | Sequence(5'---3') |
|---|---|---|
| NG6 | Forward Primer | 5'-TCGAGCTAGCATGAAGCTTGTGGAGAAGAC-3' (SEQ ID NO: 51) |
| | Reverse Primer | 5'-CGACGAGCTCTTACCTGATGGAACAAGAG-3 (SEQ ID NO: 52) |

TABLE 2-continued

Primers used for to amplify the full CDS of the aimed NG genes

| Gene name | | Sequence(5'---3') |
|---|---|---|
| NG21 | Forward Primer | 5'-ATGGTGAGTGACAAGCATGTAG-3' (SEQ ID NO: 53) |
| | Reverse Primer | 5'-TCACTTGCCCGTGATGAATG-3' (SEQ ID NO: 54) |
| NG24 | Forward Primer | 5'-ATGGGTTATCTCTCTTGCAAC-3' (SEQ ID NO: 55) |
| | Reverse Primer | 5'-TCAGTATCTCTTCCGCGACG-3' (SEQ ID NO: 56) |
| NG28 | Forward Primer | 5'-ATGGGCATGGAAGCTTTGAG-3' (SEQ ID NO: 57) |
| | Reverse Primer | 5'-TCAAAATGGAGTTTCGGCGT-3' (SEQ ID NO: 58) |
| NG32 | Forward Primer | 5'-ATGAAATGCTTCTTATTCCC-3' (SEQ ID NO: 59) |
| | Reverse Primer | 5'-TCAACAAGCTCTCACATTCT-3' (SEQ ID NO: 60) |

The vector was introduced into *Agrobacterium tumefaciens* strain GV3101 and then transformed by the floral dip method (Clough and Bent, 1998) into wild-type Col-0 to generate NG-overexpressing lines. Through two generations of selection on MS agar plate with 30 mg/l hygromycin, homologous NG transgenic lines were obtained. The resistant plants were transferred to soil to grow to maturity, and their transgenic status was confirmed by qRT-PCR analysis.

6.3 CONFIRMATION OF OVEREXPRESSION OF NG GENES IN TRANSGENIC PLANTS

The transcription levels of the NG genes in the hygromycin resistant, homologous T3 overexpression lines were confirmed by quantitative Real Time-PCR. Total RNA was extracted from 10-day-old seedlings grown on Murashige and Skoog (MS) with 3% (w/v) sucrose using the TRIzol RNA isolation method with DNase I treatment. cDNAs were generated using Superscript III reverse transcriptase (Invitrogen, Carlsbad, Calif., USA) using an oligo15 dT primer. Two gene-specific primers were used to amplify the 80-150 bp coding region of each NG gene. The ACTIN primers were used for control experiment. As shown in FIG. 4, the transcript levels of each overexpression line were consistently higher than their respective expression levels in the wild-type.

6.4 GROWTH PHENOTYPES OF NG GENE OVER-EXPRESSION LINES

*Arabidopsis* seeds were soaked in water at 4° C. for 3 days. The seeds were surface sterilized and sown on MS medium supplemented with 3% (w/v) sucrose for 10 days. Seedlings with 2 rosette leaves of the same size were transferred to soil under Long Day condition (16 h light at 22° C./8 h dark at 18° C.) in a plant growth chamber. Bolting time was measured when the primary inflorescence reached 1 cm above the rosette leaves. (Liu et al., 2008; Wu et al., 2008).

The inflorescences of NG gene OE lines emerged earlier (4-5 days) than the WT at Long Day conditions (Table 4, FIG. 5 and FIG. 6). This phenotype observation was repeated at least 3 times and the results of two of the experiments are shown here.

TABLE 4

| | WT | NG6 | NG21 | NG24 | NG28 | NG32 |
|---|---|---|---|---|---|---|
| Earlier bolting time of NG OE lines (Trial 1) | | | | | | |
| Average bolting time (Day) | 24.4 | 21.2 | 20.1 | 21.4 | 20.8 | 19.8 |
| SD | 1.4 | 1.0 | 1.4 | 0.9 | 1.0 | 1.3 |
| N | 12 | 12 | 12 | 9 | 9 | 9 |
| Earlier bolting time of NG OE lines (Trial 2) | | | | | | |
| Average bolting time (Day) | 24.3 | 19.2 | 19 | 19 | 18.3 | 19 |

TABLE 3

Primers used in the quantitative RT-PCR

| NG6 | Forward Primer | 5'-TGTGCCCGGAGCCCTACC-3' (SEQ ID NO: 61) |
|---|---|---|
| | Reverse Primer | 5'-CTTTCAGTGCCATGCGGATTTT-3 (SEQ ID NO: 62) |
| NG21 | Forward Primer | 5'-GGCACAAGTCCCGTCATCACC-3' (SEQ ID NO: 63) |
| | Reverse Primer | 5'-TCCCCAATCCCTTCTTTTCCTA-3' (SEQ ID NO: 64) |
| NG24 | Forward Primer | 5'-GCCGCCGTCAAGAGAACAAC-3' (SEQ ID NO: 65) |
| | Reverse Primer | 5'-CTCCGGTGGTCAACGCAGTAA-3' (SEQ ID NO: 66) |
| NG28 | Forward Primer | 5'-TGTTGTTGTGGCCTCGTTGTTA-3' (SEQ ID NO: 67) |
| | Reverse Primer | 5'-CTTTCCTTCACCGCCTTCTTTC-3' (SEQ ID NO: 68) |
| NG32 | Forward Primer | 5'-AAGCTTTCGGATTTCGGTTTG-3' (SEQ ID NO: 69) |
| | Reverse Primer | 5'-TGGCCTTCTTCCTGTAATGAGC-3' (SEQ ID NO: 70) |
| ACTIN | Forward Primer | 5'- CCCGCTATGTATGTCGC-3' (SEQ ID NO: 71) |
| | Reverse Primer | 5'- AAGGTCAAGACGGAGGAT-3' (SEQ ID NO: 72) |

TABLE 4-continued

|    | WT  | NG6 | NG21 | NG24 | NG28 | NG32 |
|----|-----|-----|------|------|------|------|
| SD | 0.8 | 0.8 | 1.1  | 1    | 1.0  | 0.9  |
| N  | 12  | 6   | 6    | 9    | 6    | 6    |

At maturity (Long Day), the number of inflorescence and the total weight of seeds harvested from each line were recorded. The results of two separate experimental trials are shown in Tables 5A and B. The results show that the overexpression of each of the five NG genes (NG6, NG21, NG24, NG28, and NG32) resulted in increased number of inflorescences and seed yield. Compared to that of the wild-type, the seed yield of each NG over-expression line increased 30-50% (Table 5).

TABLE 5

OE lines produced more seeds (Trial 1).

| Lines    | Weight of seeds (mg)/plant | SD   |
|----------|----------------------------|------|
| WT(Col-0)| 80.4                       | 4.9  |
| NG6      | 113.6                      | 12.2 |
| NG21     | 127.8                      | 26.9 |
| NG24     | 99.6                       | 17.3 |
| NG28     | 130.6                      | 26.7 |
| NG32     | 135.9                      | 23.5 |

The plants were grown in small black trays (N = 6-9).

OE lines produced more seeds (Trial 2).

| Lines    | Weight of seeds (mg)/plant | SD   |
|----------|----------------------------|------|
| WT(Col-0)| 142.0                      | 14.6 |
| NG6      | 190.3                      | 15.7 |
| NG21     | 180.4                      | 26.3 |
| NG24     | 203.8                      | 20.0 |
| NG28     | 186.0                      | 39.5 |
| NG32     | 241.8                      | 23.8 |

The plants were grown in large white cups (N = 6-9).

The results show that, when compared to the wild-type, Arabidopsis plants transformed with NG6, NG21, NG24, NG28 and/or NG32 have the following advantageous phenotypes: (1) faster growth rate; (2) higher seed yield.

6.5 SEQUENCE ALIGNMENT AND PHYLOGENETIC ANALYSIS

All the CDS of 5 NG genes in the *Arabidopsis* Col-0 ecotype were obtained from the TAIR website. Sequence alignment of each NG gene was retrieved by tblastn program from Plant GDB database and NCBI database using the amino acid sequence of each *Arabidopsis* NG gene as the bait sequences. Partial sequences recovered were aligned and compared to produce a full length coding sequence if feasible. Sequence alignment and phylogenetic tree were conducted using MEGA4 (Kumar et al., 2004) and ClustalW program. Amino acid sequence comparisons were performed using CLC Sequence Viewer 5.1.1.

Those skilled in the art will recognize, or be able to ascertain many equivalents to the specific embodiments of the invention described herein using no more than routine experimentation. Such equivalents are intended to be encompassed by the following claims.

All publication, patents and patent applications mentioned in this specification are incorporated herein by reference in their entireties into the specification to the same extent as if each individual publication, patent or patent application was specifically and individually indicated to be incorporated by reference in its entirety.

Citation or discussion of a reference herein shall not be construed as an admission that such is prior art to the present invention.

REFERENCES

Clough, S. J. and Bent, A. F. (1998) Floral dip: a simplified method for *Agrobacterium*-mediated transformation of *Arabidopsis thaliana. Plant J,* 16, 735-743.

Klabunde, T., Strater, N., Frohlich, R., Witzel, H. and Krebs, B. (1996) Mechanism of Fe(III)-Zn(II) purple acid phosphatase based on crystal structures. *J. mol. biol.,* 259, 737-748.

Klabunde, T. and Krebs, B. (1997) The dimetal center in purple acid phosphatases. *Metal Sites in Proteins and Models,* 89, 177-198.

Li, D., Zhu, H., Liu, K., Liu, X., Leggewie, G., Udvardi, M. and Wang, D. (2002) Purple acid phosphatases of *Arabidopsis thaliana.* Comparative analysis and differential regulation by phosphate deprivation. *J. Biol. Chem.,* 277, 27772-27781.

Schenk, G., Ge, Y., Carrington, L. E., Wynne, C. J., Searle, I. R., Carroll, B. J., Hamilton, S. and de-Jersey, J. (1999) Binuclear metal centers in plant purple acid phosphatases: Fe—Mn in sweet potato and Fe—Zn in soybean. *Arch. Biochem Biophys,* 370, 183-189.

United States Patent Application Publication No. 2010/0159065

---

What is claimed is:

1. A method to make a transgenic plant having increased rate of plant growth and/or elevated plant yields comprising:
   a) introducing a gene expression construct into a plant or plant cell, wherein the construct comprises a nucleic acid molecule encoding a kinase and the nucleic acid molecule comprises:
      i) a sequence having at least 95% identity with SEQ ID NO:43 or
      ii) a sequence encoding a polypeptide having at least 95% identity with SEQ ID NO:44;
   wherein the sequence is operatively linked to upstream and downstream regulatory components comprising a heterologous promoter; and
   b) overexpressing the nucleic acid molecule in the plant or plant cell, wherein the promoter drives the overexpression of the nucleic acid molecule.

2. The method of claim 1, wherein the nucleic acid molecule comprises:
   i) the sequence of SEQ ID NO:43; or
   ii) a sequence encoding the polypeptide of SEQ ID NO:44.

3. The method of claim 1, further comprising regenerating, from said transformed plant or plant cell, a plant having enhanced growth and/or yield.

4. The method of claim 1, wherein plant growth rate is increased.

5. The method of claim 1, wherein plant yield is increased.

6. The method of claim 1, wherein the plant is of a genus selected from the group consisting of: *Asparagus, Bromus, Hemerocallis, Hordeum, Lolium, Panicum, Pennisetum, Saccharum, Sorghum, Trigonella, Triticum, Zea, Antirrhinum, Arabidopsis, Arachis, Atropa, Brassica, Browallia, Capsicum, Carthamus, Cichorium, Citrus, Chrysanthemum, Cucumis, Datura, Daucus, Digitalis, Fragaria, Geranium, Glycine, Helianthus, Hyscyamus, Ipomoea, Latuca, Linum, Lotus, Majorana, Malva, Gossypium, Manihot, Medicago, Nemesia, Nicotiana, Onobrychis, Pelargonium, Petunia, Ranunculus, Raphanus, Salpiglossis, Senecio, Sinapis, Solanum, Trifolium, Vigna*, and *Vitis*.

7. The method of claim 1, wherein the plant is of a species of the genus *Brassica*.

8. The method of claim 1, wherein the plant is of a species selected from the group consisting of: *Glycine max, Zea mays, Solanum tuberosum, Panicum virgatum, Medicago sativa*, and *Brassica napus*.

9. The method of claim 1, wherein the plant cell is a seed, stem, shoot, or root cell.

10. The method of claim 1, wherein, total number of inflorescence and seed yield per plant are increased, and bolting time is earlier when compared to a wild-type plant of the same species cultivated under the same conditions.

11. A transgenic plant cell, comprising:
    a gene expression construct, wherein the construct comprises:
    i) a nucleic acid molecule comprising a sequence having at least 95% identity with SEQ ID NO:43 wherein said nucleic acid molecule is overexpressed in the transgenic plant cell when compared to plant cells of the same type in a wild-type plant of the same species; or
    ii) a nucleic acid molecule that encodes a protein comprising a sequence having at least 95% identity with SEQ ID NO:44, wherein said nucleic acid molecule is overexpressed in the transgenic plant cell when compared to plant cells of the same type in a wild-type plant of the same species;
    wherein the sequence is operatively linked to upstream and downstream regulatory components comprising a heterologous promoter that drives the overexpression of the nucleic acid molecule in the plant cell.

12. The transgenic plant cell of claim 11, comprising:
    i) a nucleic acid molecule comprising the sequence of SEQ ID NO: 43; or
    ii) a nucleic acid molecule that encodes a polypeptide comprising the sequence of SEQ ID NO:44.

13. The transgenic plant cell of claim 11, wherein said plant cell is of a monocotyledonous species.

14. The transgenic plant cell of claim 11, wherein said plant cell is of a dicotyledonous species.

15. The transgenic plant cell of claim 11, wherein the plant cell is of a genus selected from the group consisting of: *Asparagus, Bromus, Hemerocallis, Hordeum, Lolium, Panicum, Pennisetum, Saccharum, Sorghum, Trigonella, Triticum, Zea, Antirrhinum, Arabidopsis, Arachis, Atropa, Brassica, Browallia, Capsicum, Carthamus, Cichorium, Citrus, Chrysanthemum, Cucumis, Datura, Daucus, Digitalis, Fragaria, Geranium, Glycine, Helianthus, Hyscyamus, Ipomoea, Latuca, Linum, Lotus, Majorana, Malva, Gossypium, Manihot, Medicago, Nemesia, Nicotiana, Onobrychis, Pelargonium, Petunia, Ranunculus, Raphanus, Salpiglossis, Senecio, Sinapis, Solanum, Trifolium, Vigna*, and *Vitis*.

16. The transgenic plant cell of claim 11, wherein the plant cell is of a species of the genus *Brassica*.

17. A transgenic plant, comprising a transgenic plant cell of claim 15.

18. The transgenic plant of claim 17, wherein, total number of inflorescence and seed yield per plant are increased, and bolting time is earlier when compared to a wild-type plant of the same species cultivated under the same conditions.

19. The method of claim 10, wherein the seed yield per plant is increased by approximately 30%-50% as compared with a wild-type plant of the same species.

20. The method of claim 10, wherein the bolting time per plant is earlier by approximately 19% as compared with a wild-type plant of the same species.

21. The transgenic plant of claim 18, wherein the seed yield is increased by approximately 30%-50% as compared with a wild-type plant of the same species.

22. The transgenic plant of claim 18, wherein the boiling time is earlier by approximately 19% as compared with a wild-type plant of the same species.

* * * * *